(12) United States Patent
Hurt et al.

(10) Patent No.: US 7,026,131 B2
(45) Date of Patent: Apr. 11, 2006

(54) METHODS AND APPARATUS FOR BLOOD TYPING WITH OPTICAL BIO-DISCS

(75) Inventors: Susan Newcomb Hurt, Irvine, CA (US); John Francis Gordon, Irvine, CA (US); Kevin Robert McIntyre, Irvine, CA (US)

(73) Assignees: Nagaoka & Co., Ltd., Hyogo (JP); Burstein Technologies, Inc., Irvine, CA (US)

(*) Notice: Subject to any disclaimer, the term of this patent is extended or adjusted under 35 U.S.C. 154(b) by 7 days.

(21) Appl. No.: 10/298,263

(22) Filed: Nov. 15, 2002

(65) Prior Publication Data
US 2003/0224457 A1 Dec. 4, 2003

Related U.S. Application Data

(63) Continuation-in-part of application No. 09/988,850, filed on Nov. 19, 2001.
(60) Provisional application No. 60/379,045, filed on May 9, 2002, provisional application No. 60/375,568, filed on Apr. 25, 2002, provisional application No. 60/353,773, filed on Jan. 31, 2002, provisional application No. 60/353,014, filed on Jan. 29, 2002, provisional application No. 60/252,726, filed on Nov. 22, 2000, and provisional application No. 60/249,477, filed on Nov. 17, 2000.

(51) Int. Cl.
*G01N 33/567* (2006.01)

(52) U.S. Cl. .................. 435/7.25; 435/269; 435/291.8; 435/372; 436/521; 436/16; 422/72; 494/10

(58) Field of Classification Search ................ 210/255, 210/374, 518, 781, 782, 787; 422/63, 72, 422/99, 100, 101; 436/177, 520; 435/2, 4, 435/7.25
See application file for complete search history.

(56) References Cited

U.S. PATENT DOCUMENTS

| | | | |
|---|---|---|---|
| 3,798,459 | A | 3/1974 | Anderson et al. |
| 3,799,742 | A | 3/1974 | Coleman |

(Continued)

FOREIGN PATENT DOCUMENTS

| | | |
|---|---|---|
| EP | 0 297 394 A2 | 1/1989 |
| EP | 0 417 305 A1 | 3/1991 |

(Continued)

OTHER PUBLICATIONS

US 6,200,755, 10/2000, Virtanen (withdrawn)
Schembri et al. "Centrifugation and cappilarity integrated into a multiple analyte whole blood analyser," *Journal of Automatic Chemistry*, 17(3):99–104 (1995).

(Continued)

*Primary Examiner*—Long V. Le
*Assistant Examiner*—Nelson Yang
(74) *Attorney, Agent, or Firm*—Knobbe, Martens, Olson & Bear, LLP

(57) ABSTRACT

This invention relates to clinical diagnostic assays, related optical bio-discs, and a disc-reading apparatus. The invention is directed to methods and apparatuses for performing immunohematology assays using an optical bio-disc analysis system. The invention is further directed to an optical bio-disc for performing an immunohematologic assay including a substrate having encoded information associated therewith. The encoded information may be readable by a disc drive assembly to control rotation of the disc. The disc may also include at least one target zone or capture zone associated with the substrate. The target zone is disposed at a predetermined location relative to a center of the substrate. The disc further includes a plurality of capture antibodies immobilized within the target zone, a flow channel, fluidic circuit, or analysis chamber associated with the target zone, and an input site in fluid communication with the analysis chamber.

15 Claims, 35 Drawing Sheets

U.S. PATENT DOCUMENTS

| | | | |
|---|---|---|---|
| 3,890,101 A | | 6/1975 | Tiffany et al. |
| 3,901,658 A | | 8/1975 | Burtis et al. |
| 3,979,509 A | | 9/1976 | Giaever |
| 4,284,602 A | | 8/1981 | Kelton et al. |
| 4,469,793 A | | 9/1984 | Guigan |
| 4,608,344 A | | 8/1986 | Carter et al. |
| 4,650,662 A | * | 3/1987 | Goldfinger et al. ........ 435/7.25 |
| 4,683,120 A | | 7/1987 | Meserol et al. |
| 4,847,205 A | | 7/1989 | Burtis et al. |
| 4,877,745 A | | 10/1989 | Hayes et al. |
| 4,917,865 A | | 4/1990 | Romanauskas |
| 5,061,381 A | | 10/1991 | Burd |
| 5,122,284 A | | 6/1992 | Braynin et al. |
| 5,160,702 A | | 11/1992 | Kopf-Sill et al. |
| 5,173,193 A | | 12/1992 | Schembri |
| 5,173,262 A | | 12/1992 | Burtis et al. |
| 5,186,844 A | * | 2/1993 | Burd et al. .................. 210/782 |
| 5,191,068 A | | 3/1993 | Thomson et al. |
| 5,242,606 A | | 9/1993 | Braynin et al. |
| 5,256,376 A | | 10/1993 | Callan et al. |
| 5,281,540 A | | 1/1994 | Merkh et al. |
| 5,310,523 A | | 5/1994 | Smethers et al. |
| 5,384,261 A | | 1/1995 | Winkler |
| 5,407,554 A | | 4/1995 | Saurer |
| 5,409,665 A | | 4/1995 | Burd |
| 5,413,939 A | | 5/1995 | Gustafson et al. |
| 5,457,582 A | | 10/1995 | Victora et al. |
| 5,462,839 A | | 10/1995 | de Rooij et al. |
| 5,472,603 A | | 12/1995 | Schembri |
| 5,486,335 A | | 1/1996 | Wilding et al. |
| 5,510,270 A | | 4/1996 | Fodor et al. |
| 5,518,930 A | | 5/1996 | Burd |
| 5,552,064 A | * | 9/1996 | Chachowski et al. ....... 210/787 |
| 5,585,069 A | | 12/1996 | Zanzucchi et al. |
| 5,591,643 A | | 1/1997 | Schembri |
| 5,627,041 A | | 5/1997 | Shartle |
| 5,631,166 A | * | 5/1997 | Jewell .......................... 436/45 |
| 5,637,469 A | | 6/1997 | Wilding et al. |
| 5,783,446 A | | 7/1998 | Saul et al. |
| 5,807,522 A | | 9/1998 | Brown et al. |
| 5,837,832 A | | 11/1998 | Chee et al. |
| 5,882,903 A | | 3/1999 | Andrevski et al. |
| 5,900,481 A | | 5/1999 | Lough et al. |
| 5,932,799 A | | 8/1999 | Moles |
| 6,002,474 A | * | 12/1999 | Thomas et al. ............. 356/244 |
| 6,013,513 A | | 1/2000 | Reber et al. |
| 6,024,883 A | | 2/2000 | Jewell |
| 6,063,589 A | | 5/2000 | Kellogg et al. |
| 6,110,748 A | | 8/2000 | Reber et al. |
| 6,121,048 A | | 9/2000 | Zaffaroni et al. |
| 6,126,765 A | | 10/2000 | Ohman |
| 6,140,135 A | | 10/2000 | Landegren et al. |
| 6,143,247 A | * | 11/2000 | Sheppard et al. .............. 422/63 |
| 6,143,248 A | | 11/2000 | Kellogg et al. |
| 6,143,510 A | | 11/2000 | Hoshino et al. |
| 6,167,910 B1 | | 1/2001 | Chow |
| 6,176,962 B1 | | 1/2001 | Soane et al. |
| 6,221,315 B1 | | 4/2001 | Giesler et al. |
| 6,287,517 B1 | | 9/2001 | Ackley et al. |
| 6,302,134 B1 | | 10/2001 | Kellogg et al. |
| 6,319,468 B1 | | 11/2001 | Sheppard, Jr. et al. |
| 6,327,031 B1 | | 12/2001 | Gordon |
| 6,399,361 B1 | | 6/2002 | Brotherston et al. |
| 6,582,662 B1 | * | 6/2003 | Kellogg et al. .............. 422/72 |
| 6,632,399 B1 | * | 10/2003 | Kellogg et al. .............. 422/72 |
| 2001/0001060 A1 | | 5/2001 | Kellogg et al. |
| 2001/0055812 A1 | | 12/2001 | Mian et al. |
| 2002/0047003 A1 | | 4/2002 | Bedingham et al. |
| 2002/0071362 A1 | | 6/2002 | Worthington |
| 2002/0076354 A1 | | 6/2002 | Cohen |
| 2002/0098528 A1 | | 7/2002 | Gordon et al. |
| 2002/0106786 A1 | | 8/2002 | Carvalho et al. |
| 2002/0145960 A1 | | 10/2002 | Worthington et al. |
| 2002/0163642 A1 | | 11/2002 | Zoval et al. |
| 2002/0171838 A1 | | 11/2002 | Pal et al. |
| 2002/0172980 A1 | | 11/2002 | Phan et al. |
| 2002/0196435 A1 | | 12/2002 | Cohen et al. |
| 2003/0003464 A1 | | 1/2003 | Phan et al. |
| 2003/0054376 A1 | | 3/2003 | Mullis et al. |
| 2003/0064507 A1 | | 4/2003 | Gallagher et al. |

FOREIGN PATENT DOCUMENTS

| | | |
|---|---|---|
| EP | 0 521 421 A2 | 1/1993 |
| EP | 0 693 560 A2 | 1/1996 |
| WO | WO 96/04547 | 2/1996 |
| WO | WO 96/32841 | 10/1996 |
| WO | WO 97/21090 | 6/1997 |
| WO | WO 98/38510 | 9/1998 |
| WO | WO 00/05582 | 2/2000 |
| WO | WO 01/02737 | 1/2001 |
| WO | WO 01/46465 | 6/2001 |
| WO | WO 01/47638 | 7/2001 |
| WO | WO 01/87486 | 11/2001 |
| WO | WO 01/87487 | 11/2001 |
| WO | WO 02/42498 | 5/2002 |

OTHER PUBLICATIONS

Duffy et al. "Microfabricated Centrifugal Microfluidic Systems: Characterization and Multiple Enzymatic Assays," *Anal. Chem*, 71:4669–4678 (1999).

* cited by examiner

CELL CAPTURE ZONES MAY NOT UTILIZE STREPTAVIDIN/BIOTIN
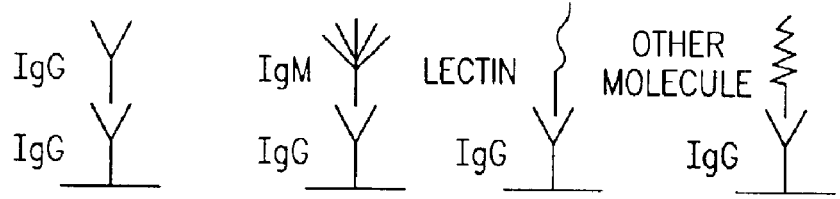
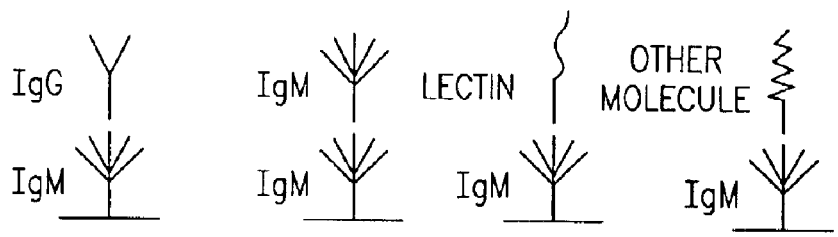
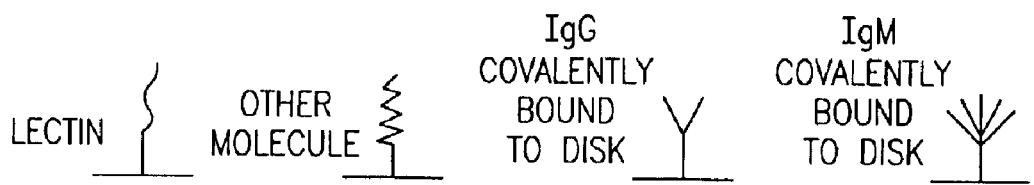
OR ANY OTHER COMBINATION
FIG.18

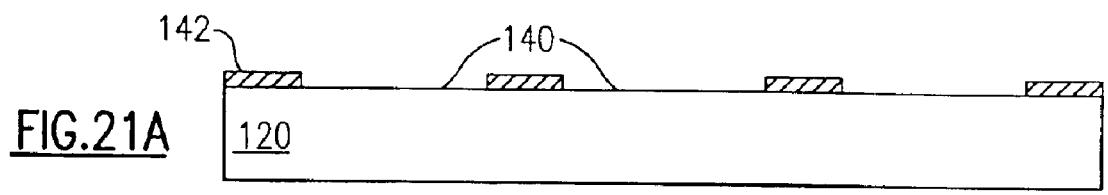
FIG. 21A
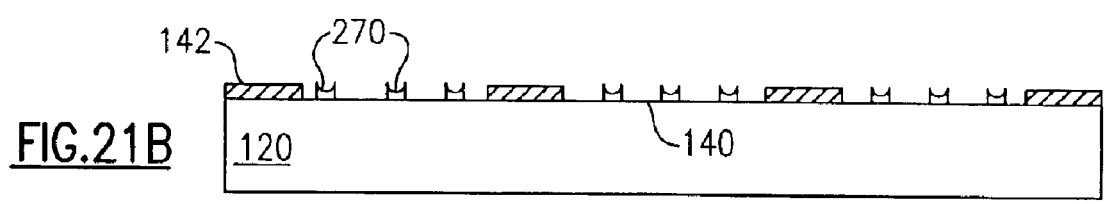
FIG. 21B
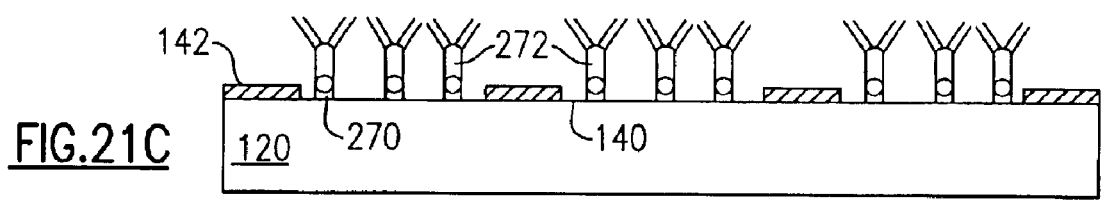
FIG. 21C
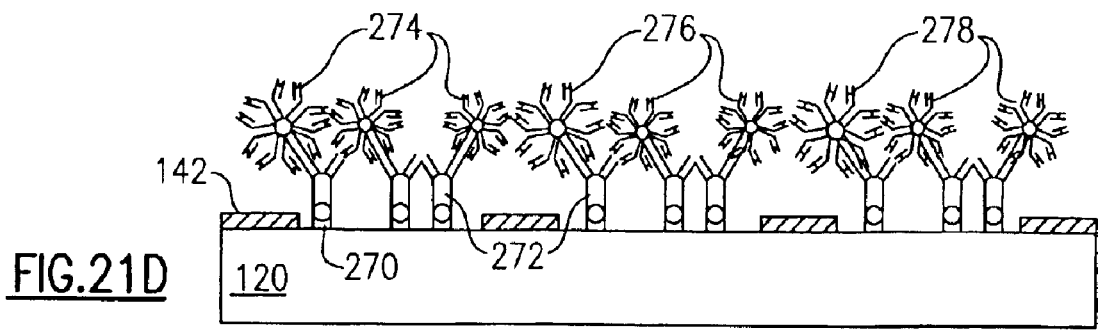
FIG. 21D
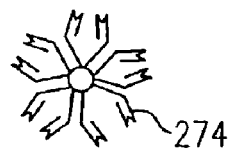
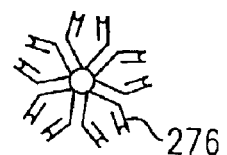
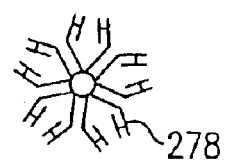

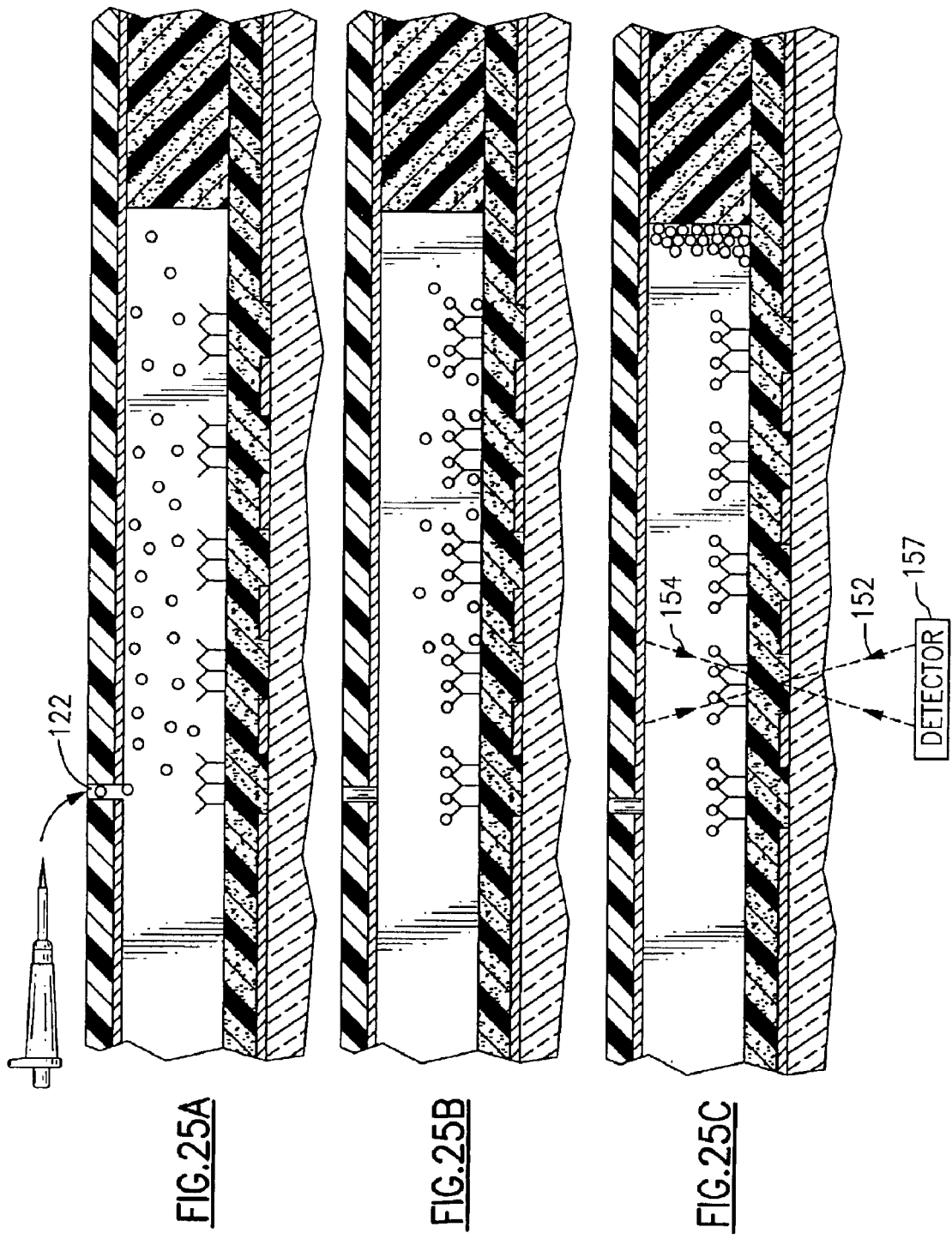

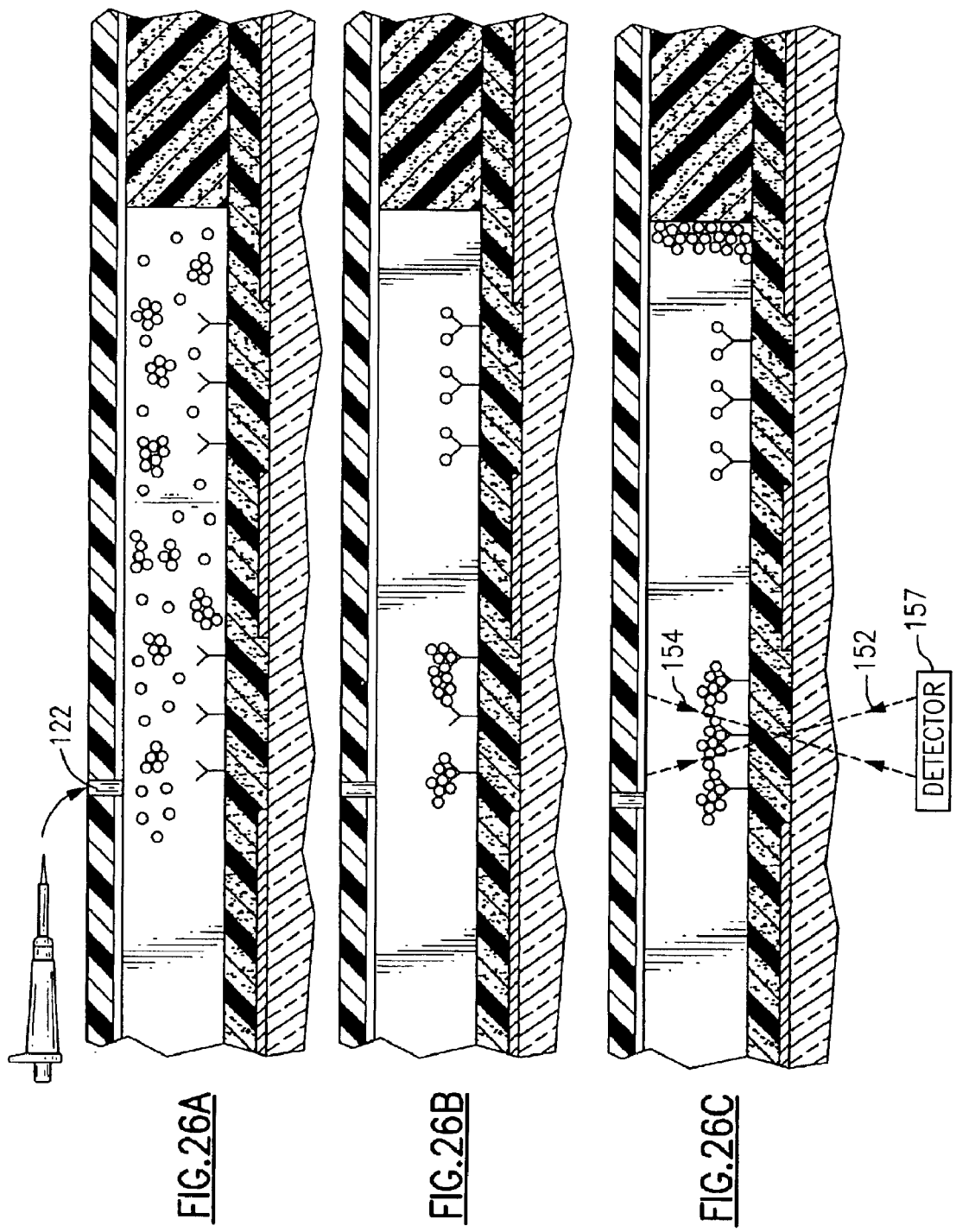

FIG.33

METHODS AND APPARATUS FOR BLOOD TYPING WITH OPTICAL BIO-DISCS

CROSS-REFERENCE TO RELATED APPLICATIONS

This application is a continuation-in-part of U.S. patent application Ser. No. 09/988,850 filed Nov. 19, 2001, which claims the benefit of priority from U.S. Provisional Application No. 60/249,477 filed Nov. 17, 2000 and U.S. Provisional Application No. 60/252,726 filed Nov. 22, 2000.

The present application also claims the benefit of priority from U.S. Provisional Application No. 60/353,014 filed Jan. 29, 2002; U.S. Provisional Application No. 60/353,773 filed Jan. 31, 2002; U.S. Provisional Application No. 60/375,568 filed Apr. 25, 2002; and U.S. Provisional Application No. 60/379,045 filed May 9, 2002. All of the above applications are hereby incorporated herein by reference in their entireties.

FIELD OF THE INVENTION

The present invention relates to the field of diagnostic assays and biological analysis and to identification of cell types and antibodies present in a biological sample and analyses related thereto. The invention is further related to the manufacture and use of optically readable discs for biological analysis.

BACKGROUND OF THE INVENTION

Medical diagnostic assays are critical to the diagnosis and treatment of disease, as well as the general maintenance of good health. Particularly useful are the biological and chemical assays performed on whole blood or its components. One early area of development in the field is related to blood typing for the purposes of transfusion. In 1901 Karl Landsteiner discovered that when the blood of one human being was transfused with that of another human being, differences in their blood might well be the cause of shock, jaundice, and the blood disorder hemoglobinuria that had resulted through earlier blood transfusions. Landsteiner classified human blood into A, B, and O groups and demonstrated that transfusions between humans of the same blood group did not result in the destruction of new blood cells and that this catastrophe occurred only when a person was transfused with the blood of a person belonging to a different group. A fourth main blood type, AB was found in 1902 by A. Decastrello and A. Sturli.

From that time, differing blood typing systems have been devised. Historically the naming of blood grouping systems has been disorganized. The common conventions stipulating that dominant traits are given capital letters and recessive traits are designated with lower case letters have not been followed. Also by tradition, red cell antigens were given alphabetical designations or were named after the family of the antibody producer.

The International Society of Blood Transfusion (ISBT) (National Blood Service/Lancaster, PO Box 111, Royal Lancaster Infirmary, Ashton Road, Lancaster LA1 4GT, England) has instituted a numerical system of nomenclature to help standardize red cell blood group terminology. This convention mandates that each system and collection has been given a number and letter designation, and each antigen within the system is numbered sequentially in order of discovery. As of this writing, over 20 blood group systems and seven antigen collections have been defined.

The structure of the antigen determinants for the ABO blood typing system was established in the 1950s by Watkins and Morgan (Nature 180:1038–1040, 1957), and Kabat et al. (Blood Group Substrates: Their Chemistry and Immuno-Chemistry, 1956, Academics Press, New York). Numerous sera and isolated antibodies have been used for ABO blood typing purposes. For example, U.S. Pat. No. 4,764,465 to Foung et al. (1988) entitled "Human Monoclonal Antibody Against Group A Red Blood Cells" is directed to a human monoclonal antibody that directly agglutinates type A human red blood cells. The exemplified antibody is an IgM and is produced by hybrid cells lines S-H22 and HHA1.

More recently, genes encoding the antigenic determinants have also been identified. See for example U.S. Pat. No. 5,326,857 to Yamamoto et al. (1994) entitled "ABO Genotyping" which discloses genes defining the ABO histo-blood groups and methods for the identification of histo-blood group ABO status. The methods described include the use of DNA probes or size separation of DNA fragments unique to a blood group status, DNA constructs, recombinant methods for providing histo-blood glycosyltransferases, methods for tumor suppression, purified histo-blood group glycosyltransferases, and antibodies produced therefrom which bind to protein epitopes.

A variety of apparatuses have been utilized to perform ABO blood typing analysis. For example, U.S. Pat. No. 4,650,662 to Goldfinger et al. (1987) entitled "Portable Blood Typing Apparatus and Method" discloses a portable apparatus to enable rapid determination of an individual's ABO blood group and Rh blood type and a method of using such apparatus. The apparatus has a plurality of microtubes joined together that contain blood taken from an individual. The assembly of microtubes is connected during use to an assembly of reaction chambers containing blood typing reagents. The apparatus enables rapid visualization of the test reactions within the reaction chambers, and may be used in locations removed from a laboratory to determine the ABO blood group and Rh blood type of an individual.

U.S. Pat. No. 5,324,479 to Naldoni et al. (1994) entitled "Analyzer for the Determination of the Phenotype and the ABO Blood Group" discloses an analyzer for the determination of the ABO blood type of a patient. The analyzer comprises a rotatable plate carrying sample-bearing test-tubes and dilution test-tubes arranged along concentric circumferences; a dispensing needle which is movable by mechanical means between a washing position, a position for drawing a sample, a position for diluting the sample and a position for introducing the sample into a reading well; a station for washing said needle; a conveyor unit for conveying carrier members which are provided with twelve reaction wells to a position for receiving diluted or the undiluted samples from the dispensing needle; an automatic feeder that feeds small balls into each of the wells during the forward motion along the conveyor unit; mechanical means for transferring the carrier member to a reading zone; a unit that meters the specific antiserum or red cells into each one of the wells; and an optical reading device that horizontally reads the transmittance of each one of the wells, starting from the moment when antiserum or red cells are introduced; and a processor for functionally controlling the analyzer and for issuing an estimate of the results of the analyses.

U.S. Pat. No. 6,030,581 entitled "Laboratory In A Disc" describes an apparatus that includes an optical disc, having a substantially self-contained assay means for binding an analyte suspected of being in a sample. U.S. Pat. No. 5,892,577 entitled "Apparatus and Method for Carrying Out Analysis of Samples" describes systems and methods for conducting an optical inspection of a biological, chemical or biochemical sample supported by an optical transparent disc.

U.S. Pat. No. 6,143,510, entitled "Measuring Method Using Whole Blood Sample" describes methods for quantitatively measuring analytes in an undiluted whole blood sample by contacting the sample with magnetic particles coated with a binding partner, which binds to an analyte in the sample. There is no description of this assay being carried out on an optical bio-disc. In addition, U.S. Pat. No. 5,993,665, entitled "Quantitative Cell Analysis Methods Employing Magnetic Separation" describes immobilization of microscopic entities into a defined region in a collection chamber such that analysis by automated means is possible. The '665 patent describes quantitative collection of magnetically labeled target entities.

There remains a need in the art of medical diagnostics for more efficient and less expensive diagnostic techniques. As compared to prior methods and systems, we have developed a simple, miniaturized, ultra-sensitive, inexpensive system for imaging and analyzing cells and their components. This system uses optical bio-discs, related detection assemblies, as well as information and signal processing methods and software.

SUMMARY OF THE INVENTION

In a first aspect, the invention provides a method for determining a blood group type of an individual by direct typing on an optical bio-disc comprising applying red blood cells to at least one chamber, channel, microfluidic channel, or micro-channel in an optical bio-disc, the chamber surface including at least one capture field including a capture antibody, at least one positive control field, and at least one negative control field; incubating the samples in the disc to promote antigen-antibody interaction; placing the disc into an optical reader that supports it on a first side; rotating the disc about an axis substantially perpendicular to the first side to separate non-captured cells from captured cells located on the chamber surface; obtaining a measurement for the test field, the positive control field, and the negative control field analyzing the measurement of the test field, the positive control field and the negative control field to determine blood group type of the individual. In certain embodiments of the first aspect, the capture antibody is an IgG antibody or the capture antibody is an IgM antibody.

In certain embodiments of the first aspect, the capture antibody is an antibody specific for a red blood cell antigen. In certain embodiments of this embodiment, the red blood cell antigen is an ABO system blood group antigen, the red blood cell antigen is an Rh system blood group antigen, the red blood cell antigen is an MNSs system blood group antigen, the red blood cell antigen is a P system blood group antigen, the red blood cell antigen is a Lutheran system blood group antigen, the red blood cell antigen is a Kell system blood group antigen, the red blood cell antigen is a Lewis system blood group antigen, the red blood cell antigen is a Duffy system blood group antigen, the red blood cell antigen is a Kidd system blood group antigen, the red blood cell antigen is a Fisher system blood group antigen, or the red blood cell antigen is a blood group antigen from any other blood group.

In other certain embodiments, the optical bio-disc is a reflective disc or the optical bio-disc is a transmissive disc. In other embodiments of the first aspect, the optical bio-disc comprises a CD, CD-R, DVD, or a DVD-R.

In certain embodiments of this aspect, the optical bio-disc has software embedded therein and the analysis of the measurement profile is controlled by the software, resulting in a bar code displaying the blood group type of the individual.

In certain embodiments of the first aspect, the capture antibody is biotinylated and is bound to the test field by streptavidin bound thereto, or the capture antibody is bound to the test field by a second antibody bound to the test field, or the capture antibody is bound to a second antibody which is biotinylated and is bound to the test field by streptavidin bound thereto.

In other embodiments of the first aspect, the positive control field has a molecule on its surface that binds all cells. In embodiments thereof, the molecule is a lectin. In another embodiment thereof, the molecule is gold.

In a second aspect, the invention provides, a method for determining the presence of antibodies to an ABO blood group in individual's blood sample by reverse-typing on an optical bio-disc including purifying serum from a blood sample; creating at least one sample by mixing serum with cells of a known ABO blood group; injecting at least one sample into at least one channel in the optical bio-disc, thereby delivering the sample onto a capture field including a cell binding molecule; incubating the sample on the capture field to allow the cells to bind to the cell binding molecule; placing the disc into an optical reader that supports it on a first side; rotating the disc about an axis substantially perpendicular to the first side; scanning the chamber with an incident beam of electromagnetic radiation by rotating the disc about an axis substantially perpendicular to the first side by moving the incident beam in a direction radial to the axis; detecting a return beam of electromagnetic radiation formed by at least a part of the incident beam after interacting with the disc; converting the return beam into an output signal; analyzing the output signal to determine the presence of agglutinated or non-agglutinated cells bound on the capture field; and determining the presence of antibodies in the sample.

In certain embodiments of the second aspect, the creating step includes the creation of two samples, a first sample utilizing Type A1 cells and a second sample utilizing Type B cells. In certain embodiments of the second aspect, step (b) further comprises the creation of a sample with Type AB cells. In certain embodiments of the second aspect, the cell-binding molecule is an anti-human immunoglobulin. In certain embodiments of the second aspect, the cell-binding molecule is a lectin or the cell-binding molecule is gold.

In another embodiment of the second aspect of the present invention, the creating step includes mixing Type A and Type B reagent cells together to produce a cell mixture. A blood serum or plasma sample is then added to the cell mixture. The resulting serum-cell mixture is added to a chamber in an optical bio-disc and incubated at a pre-determined temperature for a pre-determined time to allow ample interaction between the antibodies in the serum and the reagent cells so that agglutination of any of the typed reagent cells takes place if the appropriate antibody is present in the serum sample. The chamber in an optical bio-disc includes capture fields which contain antibodies specific for the "A" antigen and one for the "B" antigen. These specific antibodies or cell binding proteins may be IgG or IgM. The Type A reagent cells will bind to the anti-A antigen capture field and the Type B reagent cells will bind to the anti-B antigen capture field. After spinning off the unbound cells in the solution the capture fields are analyzed and software may then be used to determine weather the captured cells are agglutinated or single and thus determine the presence or absence of antibody to A and/or B antigen.

In certain embodiments of the second aspect, the optical bio-disc is a reflective disc or the optical bio-disc is a transmissive disc. In certain embodiments of the second aspect, the optical bio-disc comprises a CD, CD-R, DVD-R, or a DVD.

In a third aspect, the invention provides method for determining the presence of antibodies to an ABO blood group in an individual's blood sample by reverse-typing on an optical bio-disc comprising applying a blood sample to at least one microfluidic channel or circuit in the optical bio-disc including a separation chamber with at least one microfilter, at least one mixing chamber, and at least one capture chamber or analysis chamber; spinning the optical bio-disc for a first time at a first speed to effect separation of the blood sample into cells and serum in the separation chamber; spinning the optical bio-disc for a second time at a second speed higher than the first, the second speed effecting movement of the serum through the microfluidic channel or circuit into a mixing chamber; adding typed reagent cells of a known ABO blood group into the mixing chamber containing serum; spinning the optical bio-disc for a third time in one direction and alternately in another direction at least once to effect mixing of the serum and the cells; incubating the cells in the serum for a sufficient period of time to allow antibody-antigen binding; spinning the optical bio-disc for a fourth time at a third speed higher than the second, the third speed effecting movement of the cells into a capture chamber, the capture chamber including surface with a molecule that binds cells; incubating the sample in the capture chamber to promote cell binding to the chamber surface; spinning the disc for a fifth time to remove non-bound cells from the capture field; scanning the chamber with an incident beam of electromagnetic radiation by rotating the disc about an axis substantially perpendicular to the first side by moving the incident beam in a direction radial to the axis; detecting a return beam of electromagnetic radiation formed by at least a part of the incident beam after interacting with the disc; converting the return beam into an output signal; analyzing the output signal to determine the presence of agglutinated cells; and determining the presence of antibodies to a blood group in the sample.

In certain embodiments of the third aspect, there is a first mixing chamber connected to a first capture chamber and a second mixing chamber connected to a second capture chamber. In certain embodiments of the third aspect, Type A1 cells are placed in the first mixing chamber and Type B cells are placed in the second mixing chamber. In certain embodiments of this embodiment, the method further comprising a third mixing chamber connected to a third capture chamber and AB cells are added to the third mixing chamber in which AB cells are added.

In another embodiment of the third aspect of the present invention, the Type A1 and Type B cells are mixed together to produce a cell mixture. The cell mixture is then added to the mixing chamber containing the blood serum or plasma and incubated to allow agglutination of any of the typed reagent cells if their respective antibodies are present in the serum sample. The mixing chamber in the optical bio-disc is in fluid communication with an analysis chamber which includes capture fields that contain antibodies specific for the A antigen and for the B antigen. These specific antibodies or cell binding proteins may be IgG or IgM. When the disc is rotated the cells in the mixing chamber will move into the anaylsis chamber where the cells are captured in their respective capture fields. After spinning off the unbound cells in the solution the capture fields are analyzed and software may then be used to determine weather the captured cells are agglutinated or single and thus determine the presence or absence of antibody to A and/or B antigen.

In certain embodiments of the third aspect, the cell-binding molecule is an anti-human immunoglobulin, the cell-binding molecule is a lectin, or the cell-binding molecule is gold. In certain embodiments of the third aspect, the optical bio-disc is a reflective disc or the optical bio-disc is a transmissive disc. In certain embodiments of the third aspect, the optical bio-disc comprises a CD, DVD, CD-R, or DVD-R. In certain embodiments of the third aspect, the first speed is from about 1× to about 3×, the second speed is greater than 3× but less than about 5×, and the third speed is greater than about 5×. (1× refers to the audio standard for speed).

In a fourth aspect of the current invention, there is provided a method of performing immunohematology assays including direct and indirect blood typing and serum or plasma antibody detection using a bio-matrix. The bio-matrix may be formed from, but not limited to, cross-linked molecular structures including polyacrylamide gels, agarose, polydextran, and microspheres such as Dextran acrylamide spheres, polystyrene microspheres, and glass beads. The cross-linked molecular structures or microspheres may be packed or formed in a micro-channel in an optical bio-disc to form the bio-matrix such that the pore size of the bio-matrix is sufficiently large to allow passage of single cells and sufficiently small to a retard and retain agglutinated cells. The channel may also be filled with an assay solution necessary to carry out the desired reaction including buffer, specific antibodies, and/or anti human globulin. The creation of the bio-matrix and preparation of the assay solution in an optical bio-disc may be prepared and used, for example, as described in U.S. Pat. No. 5,512,432 to Lapierre, et al. issued on Apr. 30, 1996 and entitled "Method Detecting Antigens and/or Antibodies" which is herein incorporated by reference in its entirety. The fourth aspect of the current invention provides an improved platform for the currently used gel test methods, including those described in U.S. Pat. No. 5,512,432. The gel test method predominantly in current use was developed by Lapierre and associates in the early 1980s (Lapierre, Y., et al., *The Gel Test: A New Way to Detect Red Cell Antigen-Antibody Reactions,* Transfusion (1990); 30:109).

One distinguishing aspect of the blood typing methods of the present invention, is the ability to quantify the degree of agglutination between cells within a small chamber. Upon centrifugation, single cells pass through the matrix material pelleting at the bottom of the fluidic circuit or analysis chamber whilst agglutinated cells are retarded either entirely above the matrix material (strong reaction) or distributed through it (weak reaction) as shown below in FIGS. 37A, 37B, and 37C.

Quantification of the degree of agglutination is carried out on individual optical disc chambers either by visual examination or by a laser scanning mechanism. This quantification supports both forward and reverse blood typing assays, and serum or plasma antibody detection and testing. The major advantages of implementing this method in an optical bio-disc is that it removes the previous need for time consuming washing steps and it enables the automation of the analysis of the assay using an optical disc reader and its accompanying software.

One advantage of the fourth aspect of the current invention is that by transposing the matrix based methodology to a multi-chambered optical bio-disc, forward and reverse blood typing, serum or plasma antibody detection and testing, and other immunohematology assays can be achieved in one convenient multi-chambered bio-disc. This in itself will increase the efficiency of screening multiple samples and serum antibody panel testing, for example, in the blood banking and transfusion fields of use. Moreover by exploiting the imaging capabilities of the optical bio-disc drive the degree of agglutination can be determined with a much greater degree of accuracy. This capability is of great value in detecting very weak positive reactions. Such an optical bio-disc drive is described, for example, in U.S. patent application Ser. No. 10/043,688 entitled "Optical Disc Analysis System Including Related Methods for Biological and Medical Imaging" filed Jan. 10, 2002 which is herein incorporated by reference in its entirety.

In a fifth aspect, the invention provides a method for determining the presence of antibodies to a blood group type in an individual by antibody typing on an optical bio-disc comprising purifying serum from a blood sample; creating at least one sample by mixing serum with cells of a known blood group phenotype or typed reagent cells; injecting at least one sample into at least one channel in the optical bio-disc, thereby delivering the sample onto a capture field including a incubating the sample on the capture field to allow the cells to bind to the cell binding molecule; placing the disc into an optical reader that supports it on a first side; rotating the disc about an axis substantially perpendicular to the first side; scanning the chamber with an incident beam of electromagnetic radiation by rotating the disc about an axis substantially perpendicular to the first side by moving the incident beam in a direction radial to the axis; detecting a return beam of electromagnetic radiation formed by at least a part of the incident beam after interacting with the disc; converting the return beam into an output signal; analyzing the output signal to determine the presence of cells bound to the capture field; and determining the presence of blood group antibodies.

In certain embodiments of the fifth aspect, the cell-binding molecule is an anti-human immunoglobulin. In other embodiments of this aspect, the optical bio-disc is a reflective and/or transmissive disc. In certain embodiments of this aspect, the optical bio-disc comprises a CD, DVD, CD-R, or DVD-R.

In certain embodiments of the fifth aspect, the cells added are characterized as having at least one of the following: an ABO system blood group cell phenotype, an Rh system blood group cell phenotype, an MNSs system blood group cell phenotype, a P system blood group cell phenotype, a Lutheran system blood group cell phenotype, a Kell system blood group cell phenotype, a Lewis system blood group cell phenotype, a Duffy system blood group cell phenotype, a Kidd system blood group cell phenotype, a Fisher system blood group antigen, or a red blood cell group antigen from any other group.

In a sixth aspect, the invention provides a method for determining the presence of antibodies to a blood group type in an individual's blood sample by antibody-typing on an optical bio-disc comprising applying a blood sample to at least one microfluidic channel in the optical bio-disc including a separation chamber with at least one microfilter, at least one mixing chamber, and at least one capture chamber; spinning the optical bio-disc for a first time at a first speed to effect separation of the blood sample into cells and serum in the separation chamber; spinning the optical bio-disc for a second time at a second speed higher than the first, the second speed effecting movement of the serum through the microfluidic channel into a mixing chamber; adding cells of a known blood group cell phenotype into the mixing chamber containing serum; spinning the optical bio-disc for a third time in one direction and alternately in another direction at least once to effect mixing of the serum and the cells; incubating the cells in the serum for a sufficient period of time to allow antibody-antigen binding; spinning the optical bio-disc for a fourth time at a third speed higher than the second, the third speed effecting movement of the cells into a capture chamber, the capture chamber including a surface with an anti-human immunoglobulin molecule; incubating the sample in the capture chamber to promote cell binding to the chamber surface; spinning the optical bio-disc for a fifth time to remove non-bound cells; scanning the chamber with an incident beam of electromagnetic radiation by rotating the disc about an axis substantially perpendicular to the first side by moving the incident beam in a direction radial to the axis; detecting a return beam of electromagnetic radiation formed by at least a part of the incident beam after interacting with the disc; converting the return beam into an output signal; analyzing the output signal to determine if the cells are bound; and determining the presence of blood group antibodies in the sample.

In certain embodiments of this aspect, the cell-binding molecule is a lectin or wherein the cell-binding molecule is gold. In other certain embodiments of the fifth aspect, the optical bio-disc is a reflective disc or the optical bio-disc is a transmissive disc. In certain embodiments of this embodiment, the optical bio-disc comprises a CD, CD-R, DVD, or DVD-R. In certain embodiments of this embodiment, the first speed is from about 1× to about 3×, the second speed is greater than 3× but less than about 5×, and the third speed is greater than about 5×.

In certain embodiments of the sixth aspect, the cells added are characterized as having at least one of the following: an ABO system blood group cell phenotype, an Rh system blood group cell phenotype, an MNSs system blood group cell phenotype, a P system blood group cell phenotype, a Lutheran system blood group cell phenotype, a Kell system blood group cell phenotype, a Lewis system blood group cell phenotype, a Duffy system blood group cell phenotype, a Kidd system blood group cell phenotype, a Fisher system blood group antigen, or a red blood cell group antigen from any other blood group.

In a seventh aspect, the invention provides an apparatus for determining a blood group type of an individual. The apparatus includes an optical bio-disc including at least one capture chamber including a layer including a first capture antibody, and a layer including a second capture antibody bound by the first capture antibody, the second capture antibody being specific for a blood group antigen; a disc drive assembly; an optical reader; and software for blood group analysis.

In certain embodiments of the seventh aspect, the capture antibody is an anti-IgG antibody or the capture antibody is an anti-IgM antibody. In certain embodiments of the sixth aspect, the capture antibody is an antibody specific for a red blood cell antigen. In certain embodiments of the latter embodiment, red blood cell antigen is an ABO system blood group antigen, the red blood cell antigen is an Rh system blood group antigen, the red blood cell antigen is an MNSs system blood group antigen, the red blood cell antigen is a P system blood group antigen, the red blood cell antigen is a Lutheran system blood group antigen, the red blood cell antigen is a Kell system blood group antigen, the red blood cell antigen is a Lewis system blood group antigen or the red blood cell antigen is a Duffy system blood group antigen, the red blood cell antigen is a Kidd system blood group antigen, the red blood cell antigen is a Fisher system blood group antigen, or a red blood cell group antigen from any other group. In certain embodiments of the sixth aspect, the optical bio-disc is a reflective disc or the optical bio-disc is a transmissive disc or the optical bio-disc comprises a CD or a DVD.

In an eighth aspect, the invention provides an optical-bio disc for performing immunohematology assays. The bio-disc includes a substrate; a separation chamber associated with the substrate, the separation chamber including first inlet port; filter means associated with the separation chamber; a first mixing chamber in fluid communication with the separation chamber, the first mixing chamber including a second inlet port; a second mixing chamber in fluid communication with the separation chamber, the second mixing chamber including a third inlet port; a first analysis or detection chamber in fluid communication with the first mixing chamber, the first analysis or detection chamber including a capture field; and a second analysis or detection chamber in fluid communication with the second mixing chamber, the second analysis or detection chamber including a capture field. In certain embodiments of the eighth aspect, the optical bio-disc does not contain a second inlet port leading to the mixing chamber (e.g., if the material that would otherwise be delivered via the second inlet port is supplied ahead of time in the mixing chamber, in freeze-dried or other form).

In certain embodiments of the eighth aspect, when a sample of blood is directed into the separation chamber through the inlet port and the disc is rotated at a first speed, the filter means separates white blood cells, red blood cells, and platelets from the blood sample to provide a sample of serum. In a further embodiment, when the disc is rotated at a second speed, the sample of serum is directed into the first and second mixing chambers. In another embodiment, the inlet port of the first mixing chamber is employed to direct cells of a first type into the first mixing chamber, and the inlet port of the second mixing chamber is employed to direct cells of a second type into the second mixing chamber. In other certain embodiments, when the disc is rotated at a third speed, a mixture of serum and cells of the first type is directed into the first analysis or detection chamber, and a mixture of serum and cells of the second type is directed into the second analysis or detection chamber.

Certain embodiments of the eighth aspect provide for disc rotation in a predetermined manner to mix the cells of the first type with serum in the first mixing chamber, and mix the cells of the second type with serum in the second mixing chamber. In certain embodiments, the predetermined manner of rotating the disc includes alternately rotating the disc in one direction and then an opposite direction to thereby create an agitation action to promote mixing of serum and cells.

In certain embodiments of the eighth aspect, the capture field in the first analysis or detection chamber includes a first type of capture agent implemented to capture specific cells having any affinity therefor. In other certain embodiments, the capture field in the second analysis or detection chamber includes a second type of capture agent implemented to capture specific cells having any affinity therefor.

In certain embodiments of the eighth aspect, an incident beam of radiant energy is directed into the first analysis or detection chamber to determine whether any cells were captured by the first type of capture agent. In other embodiments, an incident beam of radiant energy is directed into the second analysis or detection chamber to determine whether any cells were captured by the second type of capture agent.

In certain embodiments of the eighth aspect, the first type of capture agent is an anti-human immunoglobulin having an affinity for an antibody bound to the cells or a non-cell specific molecule that binds a molecule on the surface of all red blood cells. In certain embodiments of the eighth aspect, the second type of capture agent is an anti-human immunoglobulin having an affinity for an antibody bound to the cells or a non-cell specific molecule that binds a molecule on the surface of all red blood cells.

In certain embodiments of the eighth aspect, the separation chamber, the first and second mixing chambers, and the first and second analysis or detection chambers are formed in the substrate. In other certain embodiments of the seventh aspect, the separation chamber, the first and second mixing chambers, and the first and second analysis or detection chambers are formed in a cap bonded to the substrate. In yet other certain embodiments of the eighth aspect, the separation chamber, the first and second mixing chambers, and the first and second analysis or detection chambers are formed in a channel layer bonded between a cap portion and the substrate. In certain embodiments of the seventh aspect, the separation chamber, the first and second mixing chambers, and the first and second analysis or detection chambers are partially formed in a cap portion and partially formed in the substrate, the cap portion and the substrate being bonded together in register to thereby fully form the chambers.

In certain embodiments of the eighth aspect, the optical bio-disc further includes information encoded in an information layer readable by a disc drive. In certain embodiments thereof, the encoded information is used to rotate the disc in a prescribed manner. In certain embodiments of the eighth aspect, the information layer is reflective. In yet other embodiments of this aspect, the information layer is semi-reflective.

In a ninth aspect, the invention provides an optical-bio disc for performing immunohematology assays. The bio-disc includes a substrate; a separation chamber associated with the substrate, the separation chamber including first inlet port; filter means associated with the separation chamber; a first mixing chamber in fluid communication with the separation chamber, the first mixing chamber including a second inlet port; a second mixing chamber in fluid communication with the separation chamber, the second mixing chamber including a third inlet port; a first analysis or detection chamber in fluid communication with the first mixing chamber, the first analysis or detection chamber including a bio-matrix; and a second analysis or detection chamber in fluid communication with the second mixing chamber, the second analysis or detection chamber including a bio-matrix. In certain embodiments of the ninth aspect, the optical bio-disc does not contain a second inlet port leading to the mixing chamber (e.g., if the material that would otherwise be delivered via the second inlet port is supplied ahead of time in the mixing chamber, in freeze-dried or other form).

In certain embodiments of the ninth aspect, when a sample of blood is directed into the separation chamber through the inlet port and the disc is rotated at a first speed, the filter means separates white blood cells, red blood cells, and platelets from the blood sample to provide a sample of serum. In a further embodiment, when the disc is rotated at a second speed, the sample of serum is directed into the first and second mixing chambers. In another embodiment, the inlet port of the first mixing chamber is employed to direct cells of a first type into the first mixing chamber, and the inlet port of the second mixing chamber is employed to direct cells of a second type into the second mixing chamber.

In other certain embodiments, when the disc is rotated at a third speed, a mixture of serum and cells of the first type is directed into the first analysis or detection chamber, and a mixture of serum and cells of the second type is directed into the second analysis or detection chamber.

Certain embodiments of the ninth aspect provide for disc rotation in a predetermined manner to mix the cells of the first type with serum in the first mixing chamber, and mix the cells of the second type with serum in the second mixing chamber. In certain embodiments, the predetermined manner of rotating the disc includes alternately rotating the disc in one direction and then an opposite direction to thereby create an agitation action to promote mixing of serum and cells.

In certain embodiments of the ninth aspect, an incident beam of radiant energy is directed into the first analysis or detection chamber to determine the location of cells and amount of agglutination within the first analysis or detection chamber. In other embodiments, an incident beam of radiant energy is directed into the second analysis or detection chamber to determine the location of cells and amount of agglutination within the second analysis or detection chamber.

In certain embodiments of the ninth aspect, the first and second analysis or detection chambers may include anti-human immunoglobulin having an affinity for an antibody bound to the cells or a non-cell specific molecule that binds a molecule on the surface of all red blood cells.

In certain embodiments of the ninth aspect, the separation chamber, the first and second mixing chambers, and the first and second analysis or detection chambers are formed in the substrate. In other certain embodiments of the seventh aspect, the separation chamber, the first and second mixing chambers, and the first and second analysis or detection chambers are formed in a cap bonded to the substrate. In yet other certain embodiments of the ninth aspect, the separation chamber, the first and second mixing chambers, and the first and second analysis or detection chambers are formed in a channel layer bonded between a cap portion and the substrate. In certain embodiments of the ninth aspect, the separation chamber, the first and second mixing chambers, and the first and second analysis or detection chambers are partially formed in a cap portion and partially formed in the substrate, the cap portion and the substrate being bonded together in register to thereby fully form the chambers.

In certain embodiments of the ninth aspect, the optical bio-disc further includes information encoded in an information layer readable by a disc drive. In certain embodiments thereof, the encoded information is used to rotate the disc in a prescribed manner. In certain embodiments of the ninth aspect, the information layer is reflective. In yet other embodiments of this aspect, the information layer is semi-reflective.

In an tenth aspect, the invention provides a method for manufacturing a disc comprising: providing over a substrate of the disc an encoded informational layer; forming target areas; providing a capture layer in the target areas; attaching at least one capture agent. In certain embodiments, the encoded informational layer is a reflective layer, and the target areas are regions etched from the reflective layer. In certain embodiments, the encoded informational layer is a partially reflective and partially transmissive layer, and the target areas are regions adjacent to the informational layer.

In an eleventh aspect, the invention provides a method for manufacturing a disc comprising: providing over a substrate of the disc an encoded informational layer; providing a cover disc; forming fluidic circuits between the cover disc and the substrate; and forming a bio-matrix with a predetermined pore size within said fluidic circuits. In certain embodiments, the encoded informational layer is a reflective layer, and the target areas are regions etched from the reflective layer. In certain embodiments, the encoded informational layer is a partially reflective and partially transmissive layer, and the target areas are regions adjacent to the informational layer.

The above described and many other features and attendant advantages of the present invention will become better understood by reference to the following detailed description when taken in conjunction with the accompanying drawing figures and experimental examples.

BRIEF DESCRIPTION OF THE DRAWING FIGURES

Further objects of the present invention together with additional features contributing thereto and advantages accruing therefrom will be apparent from the following description of the preferred embodiments of the invention which are shown in the accompanying drawing with like reference numerals indicating like components throughout, wherein:

FIG. 18 is a pictorial presenting a general schematic of the cell capture technologies of the invention;

FIGS. 21A to 21F is a schematic presenting a series of cross sections demonstrating the preparation of one example of a bio-disc of the invention;

FIGS. 25A to 25C are cross-sectional side views of an optical bio-disc showing cell binding during the reverse typing test when no antibodies to an ABO/Rh blood group antigen are present;

FIGS. 26A to 26C are cross sectional side views of an optical bio-disc showing differential cell binding during the reverse typing test where Type A and Type B cells are mixed together and specific anti-A and anti-B capture fields are present;

FIG. 33 is a pictorial of a computer monitor screen shot presenting an output of an ABO blood typing test;

Figure 37A:
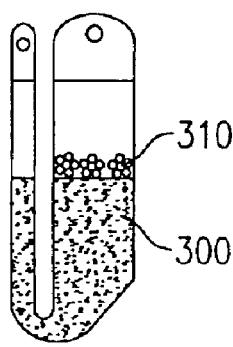
Figure 37B:
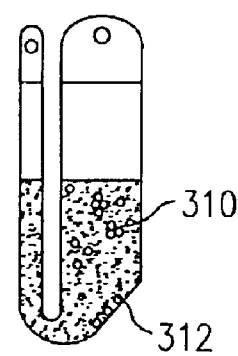
Figure 37C:
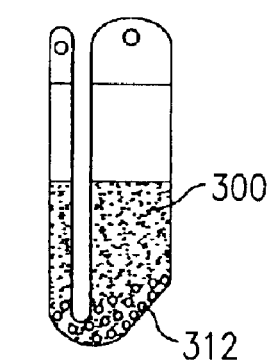
Figure 38:
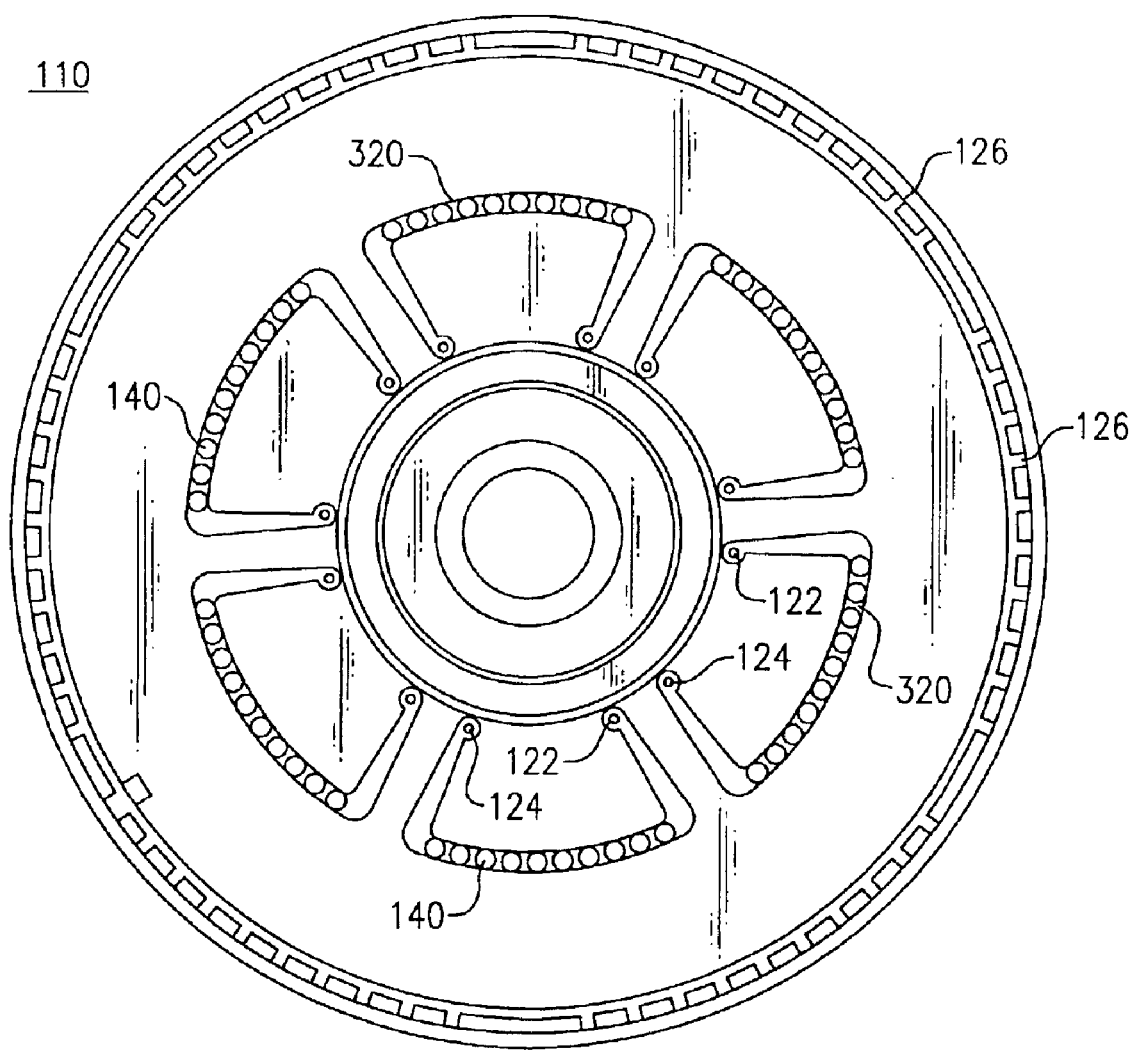
Figure 39:
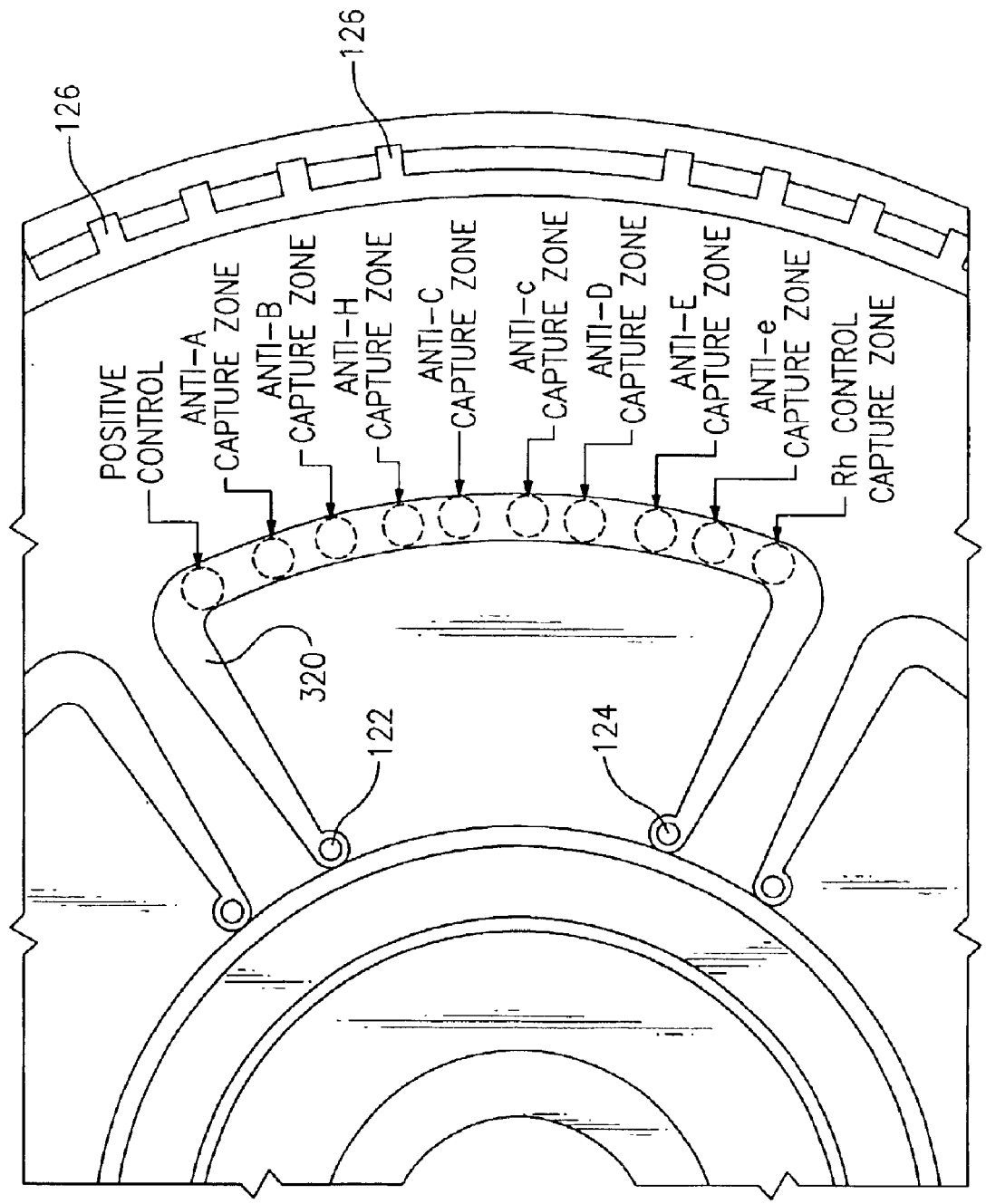
Figure 40:
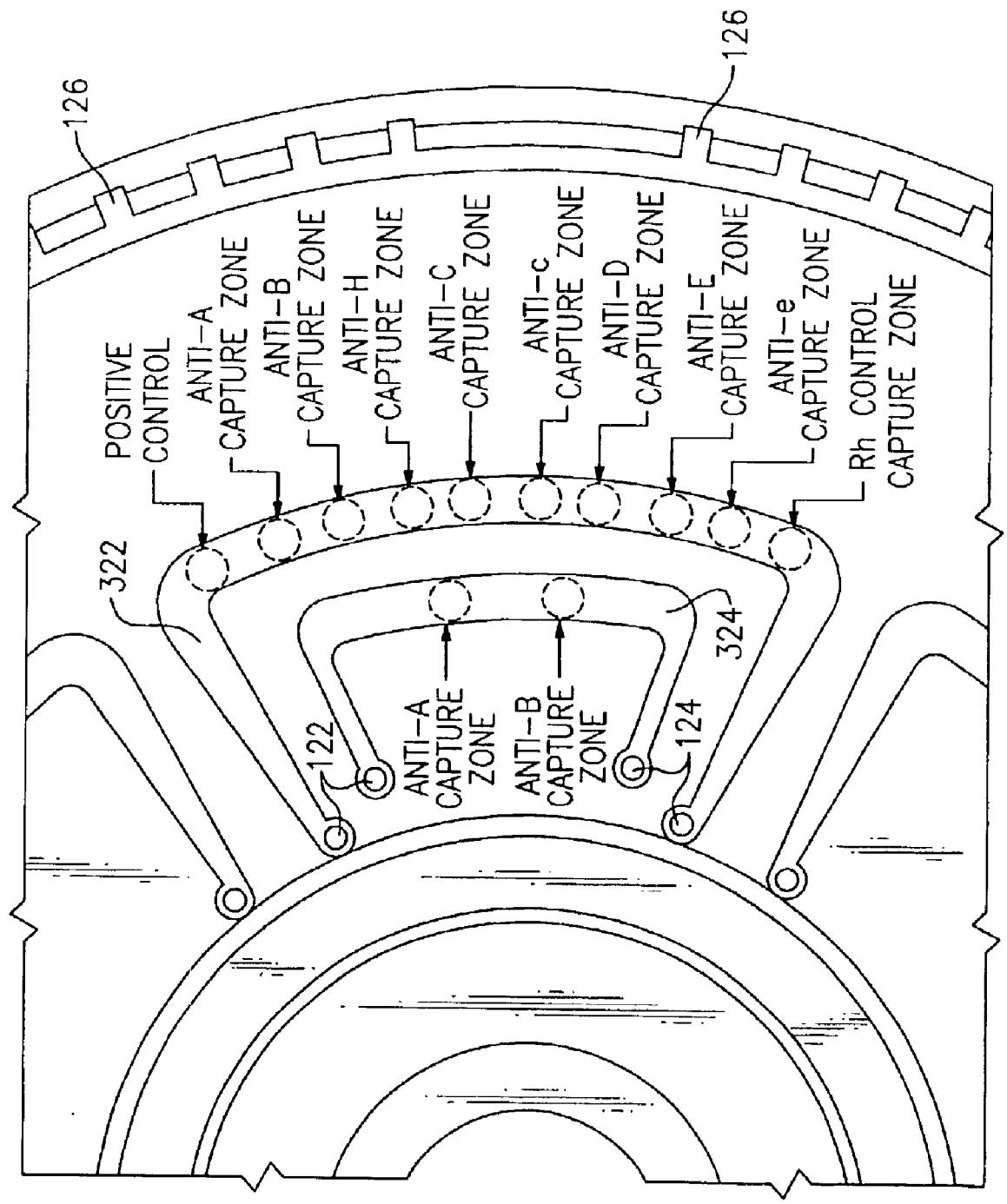

FIGS. 37A, 37B, and 37C show three different patterns of particle separation using a bio-matrix respectively depicting strong, weak, and negative reactions;

FIG. 38 is a top plan view of another embodiment of a transmissive optical bio-disc showing semi-circular, equi-radial fluidic circuits;

FIG. 39 is an enlarged detailed view of a portion of the equi-radial fluidic circuit of the disc shown in FIG. 38; and FIG. 40 is an enlarged detailed view of a portion of yet another embodiment of the transmissive disc with proximal and distal equi-radial fluidic circuits.

DETAILED DESCRIPTION OF THE INVENTION

The patents and publications cited herein reflect the level of knowledge in the art and are hereby incorporated by reference in their entirety. Any conflict between any teaching of such references and this specification shall be resolved in favor of the latter.

The invention described herein provides diagnostic assays based on cell-capture and/or cell separation technologies adapted to an optical bio-disc and methods and compositions related thereto.

Drive System and Related Discs

Figure 1:
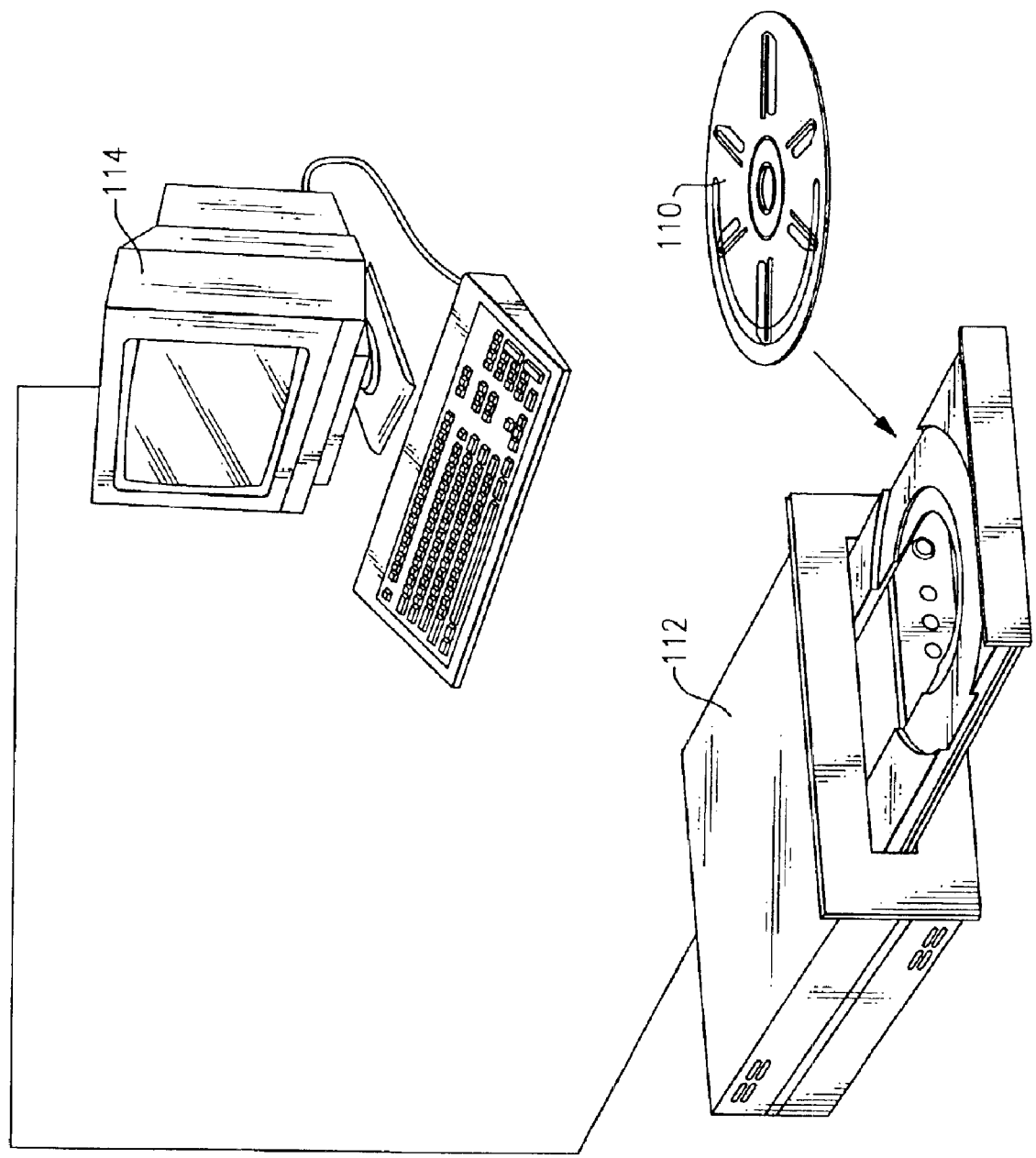
FIG. 1 is a pictorial representation of a bio-disc system according to the present invention.

FIG. 1 is a perspective view of an optical bio-disc 110 according to the present invention as implemented to conduct the cell counts and differential cell counts disclosed herein. The present optical bio-disc 110 is shown in conjunction with an optical disc drive 112 and a display monitor 114. Further details relating to this type of disc drive and disc analysis system are disclosed in commonly assigned and copending U.S. patent application Ser. No. 10/008,156 entitled "Disc Drive System and Methods for Use with Bio-discs" filed Nov. 9, 2001 and U.S. patent application Ser. No. 10/043,688 entitled "Optical Disc Analysis System Including Related Methods For Biological and Medical Imaging" filed Jan. 10, 2002, both of which are herein incorporated by reference.

Figure 2:
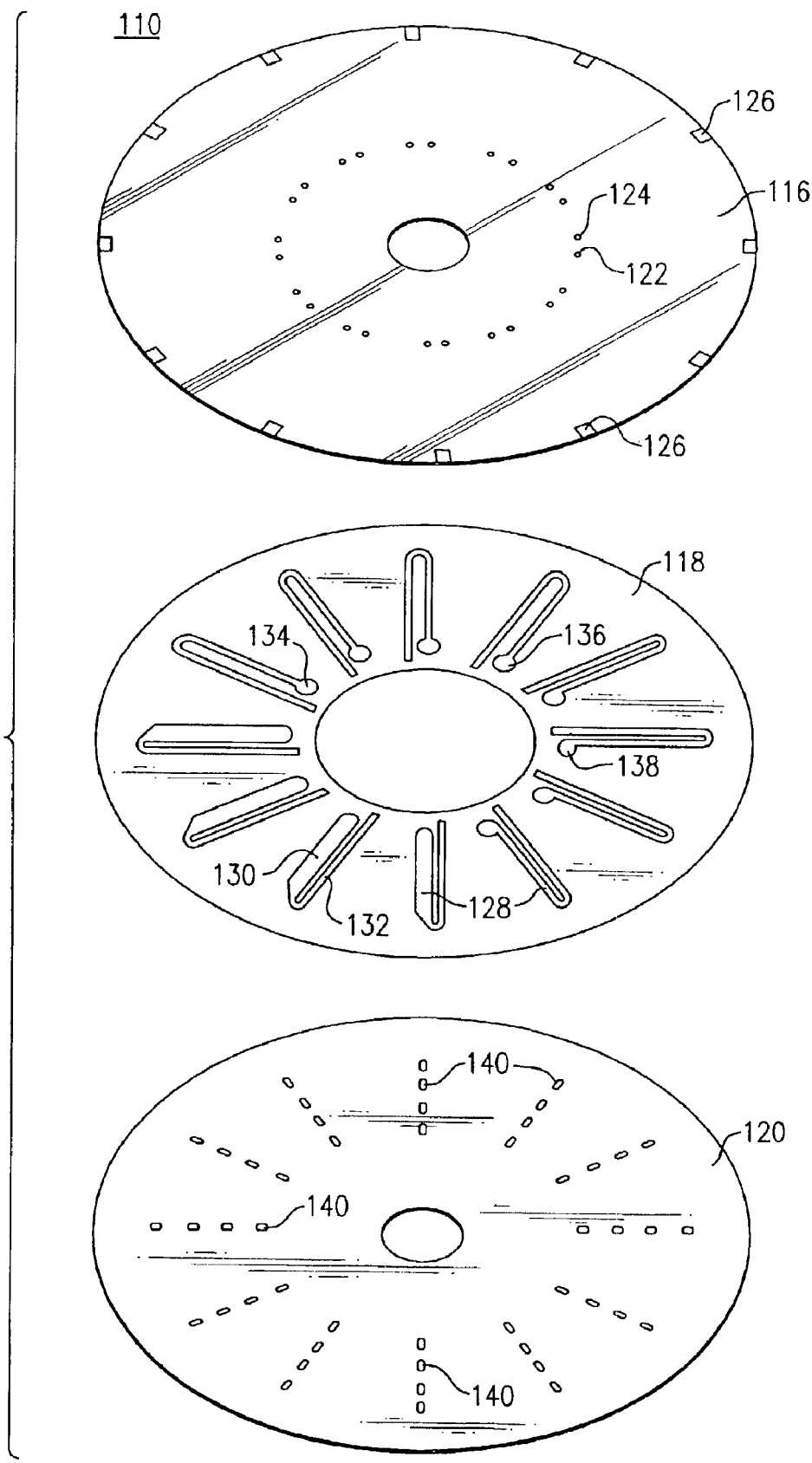
FIG. 2 is an exploded perspective view of a reflective bio-disc as utilized in conjunction with the present invention.
Figure 4:
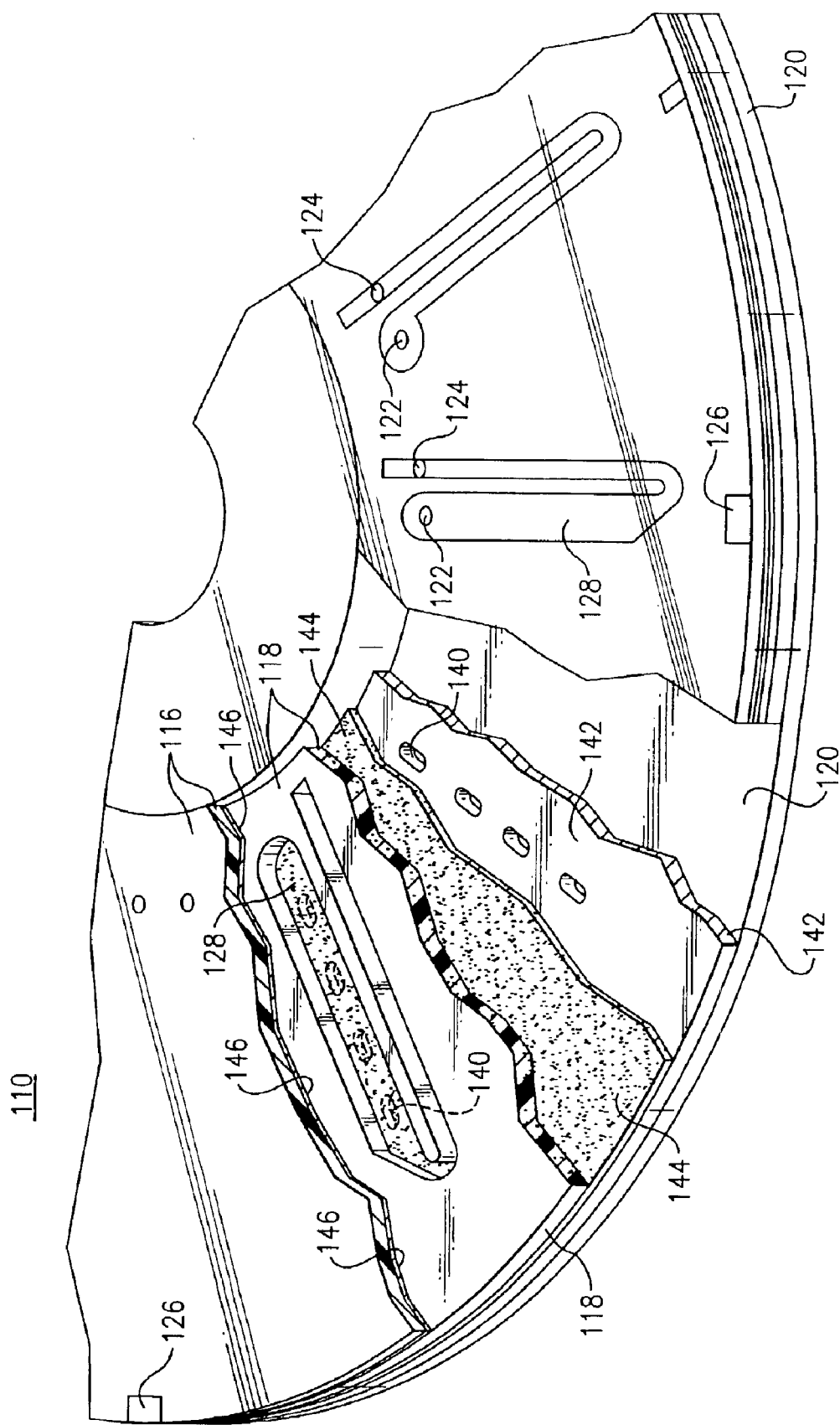
FIG. 4 is a perspective view of the disc illustrated in FIG. 2 with cut-away sections showing the different layers of the disc.

FIG. 2 is an exploded perspective view of the principal structural elements of one embodiment of the optical bio-disc 110. FIG. 2 is an example of a reflective zone optical bio-disc 110 (hereinafter "reflective disc") that may be used in the present invention. The principal structural elements include a cap portion 116, an adhesive member or channel layer 118, and a substrate 120. The cap portion 116 includes one or more inlet ports 122 and one or more vent ports 124. The cap portion 116 may be formed from polycarbonate and is preferably coated with a reflective surface 146 (FIG. 4) on the bottom thereof as viewed from the perspective of FIG. 2. In the preferred embodiment, trigger marks or markings 126 are included on the surface of the reflective layer 142 (FIG. 4). Trigger markings 126 may include a clear window in all three layers of the bio-disc, an opaque area, or a reflective or semi-reflective area encoded with information that sends data to a processor 166, as shown FIG. 10, that in turn interacts with the operative functions of the interrogation or incident beam 152, FIGS. 6 and 10.

The second element shown in FIG. 2 is an adhesive member or channel layer 118 having fluidic circuits 128 or U-channels formed therein. The fluidic circuits 128 are formed by stamping or cutting the membrane to remove plastic film and form the shapes as indicated. Each of the fluidic circuits 128 includes a flow channel 130 and a return channel 132. Some of the fluidic circuits 128 illustrated in FIG. 2 include a mixing chamber 134. Two different types of mixing chambers 134 are illustrated. The first is a symmetric mixing chamber 136 that is symmetrically formed relative to the flow channel 130. The second is an off-set mixing chamber 138. The off-set mixing chamber 138 is formed to one side of the flow channel 130 as indicated.

The third element illustrated in FIG. 2 is a substrate 120 including target or capture fields 140. The substrate 120 is preferably made of polycarbonate and has a reflective layer 142 deposited on the top thereof, FIG. 4. The target zones 140 are formed by removing the reflective layer 142 in the indicated shape or alternatively in any desired shape. Alternatively, the target zone 140 may be formed by a masking technique that includes masking the target zone 140 area before applying the reflective layer 142. The reflective layer 142 may be formed from a metal such as aluminum or gold.

Figure 3:
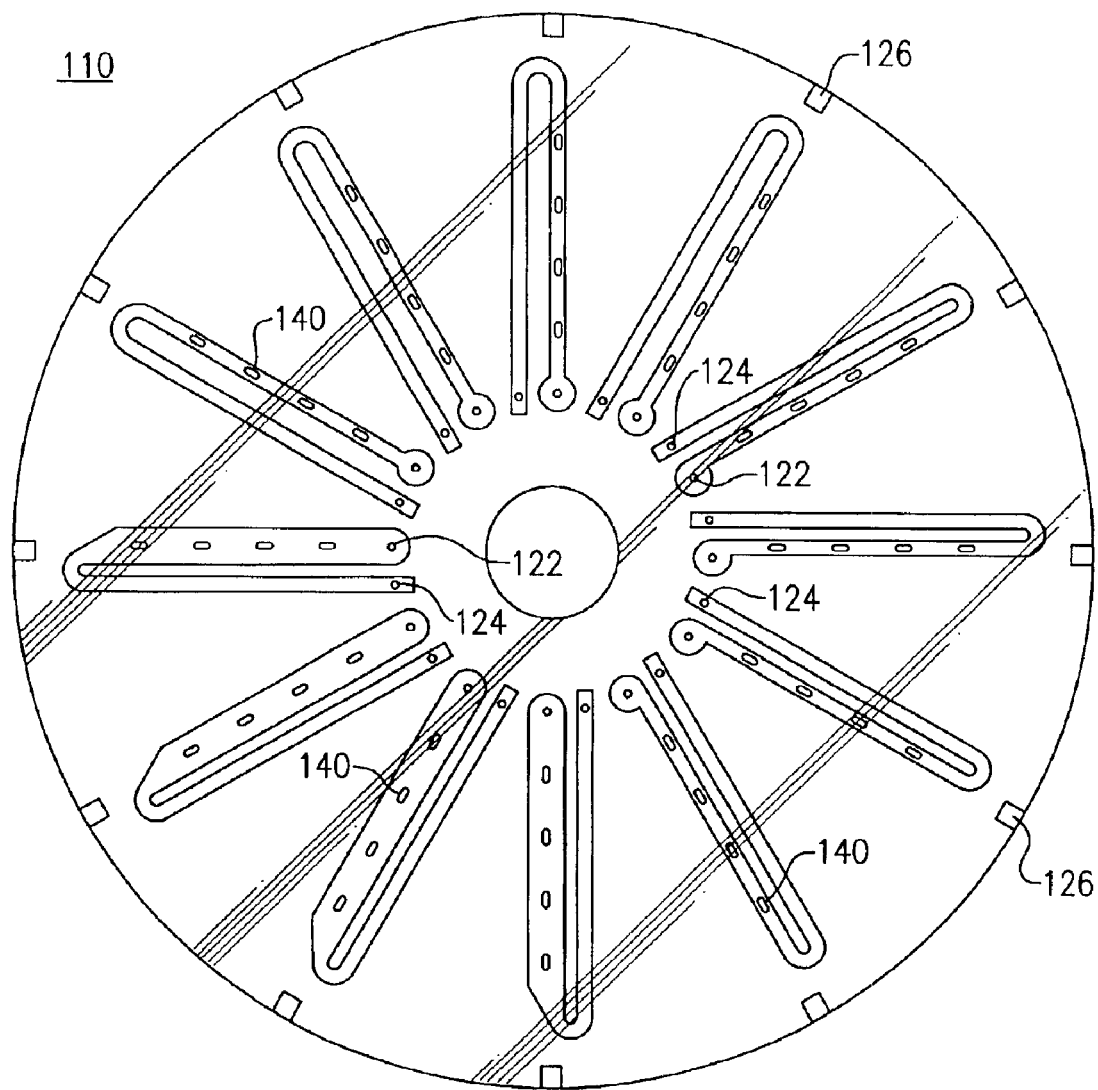
FIG. 3 is a top plan view of the disc shown in FIG. 2.

FIG. 3 is a top plan view of the optical bio-disc 110 illustrated in FIG. 2 with the reflective layer 142 on the cap portion 116 shown as transparent to reveal the fluidic circuits, the target zones 140, and trigger markings 126 situated within the disc.

FIG. 4 is an enlarged perspective view of the reflective zone type optical bio-disc 110 according to one embodiment of the present invention. This view includes a portion of the various layers thereof, cut away to illustrate a partial sectional view of each principal layer, substrate, coating, or membrane. FIG. 4 shows the substrate 120 that is coated with the reflective layer 142. An active layer 144 is applied over the reflective layer 142. In the preferred embodiment, the active layer 144 may be formed from polystyrene. Alternatively, polycarbonate, gold, activated glass, modified glass, or modified polystyrene, for example, polystyrene-co-maleic anhydride, may be used. In addition, hydrogels can be used. Alternatively as illustrated in this embodiment, the plastic adhesive member 118 is applied over the active layer 144. The exposed section of the plastic adhesive member 118 illustrates the cut out or stamped U-shaped form that creates the fluidic circuits 128. The final principal structural layer in this reflective zone embodiment of the present bio-disc is the cap portion 116. The cap portion 116 includes the reflective surface 146 on the bottom thereof. The reflective surface 146 may be made from a metal such as aluminum or gold.

Figure 5:
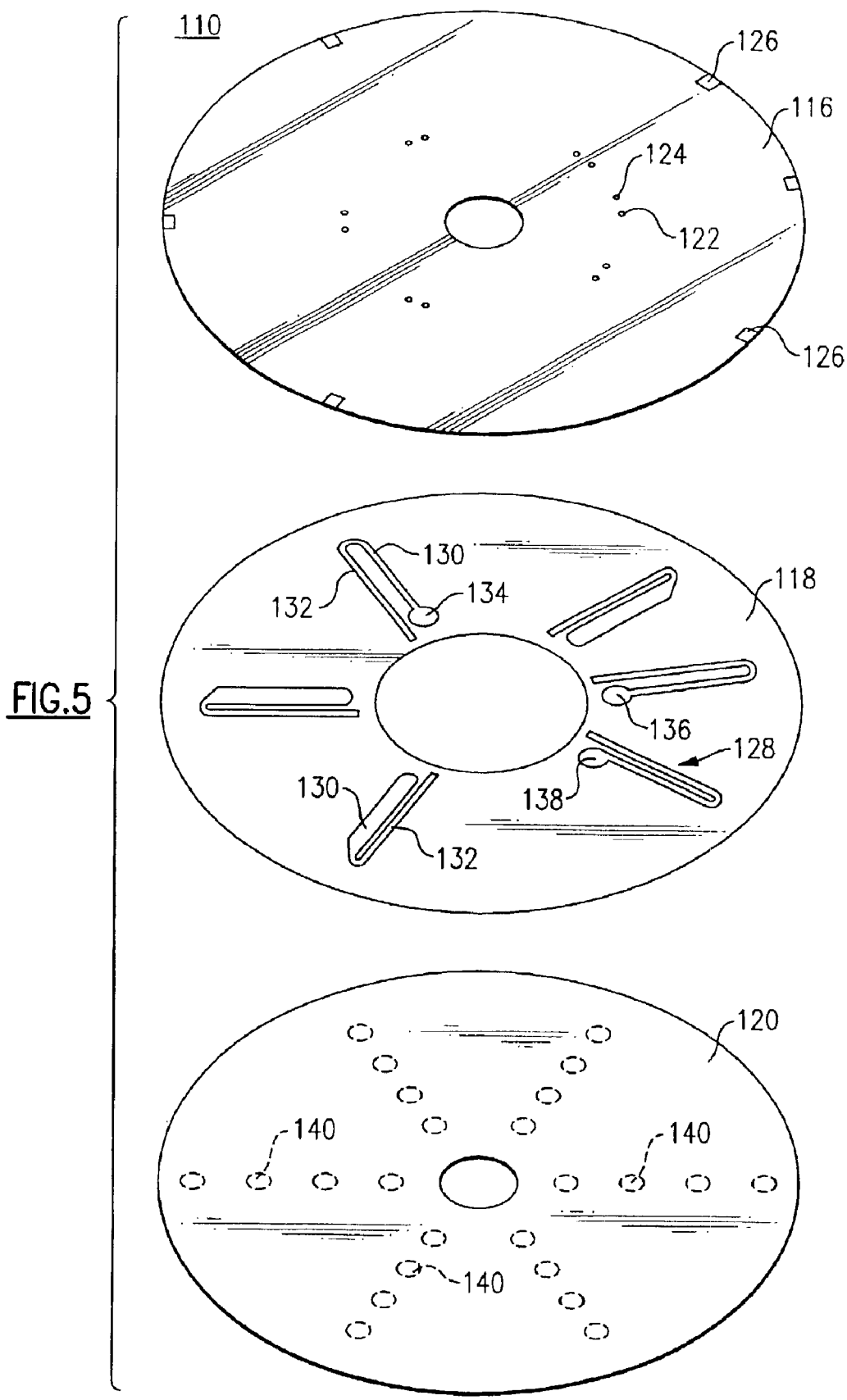
FIG. 5 is an exploded perspective view of one embodiment of a transmissive bio-disc as employed in conjunction with the present invention.
Figure 6:
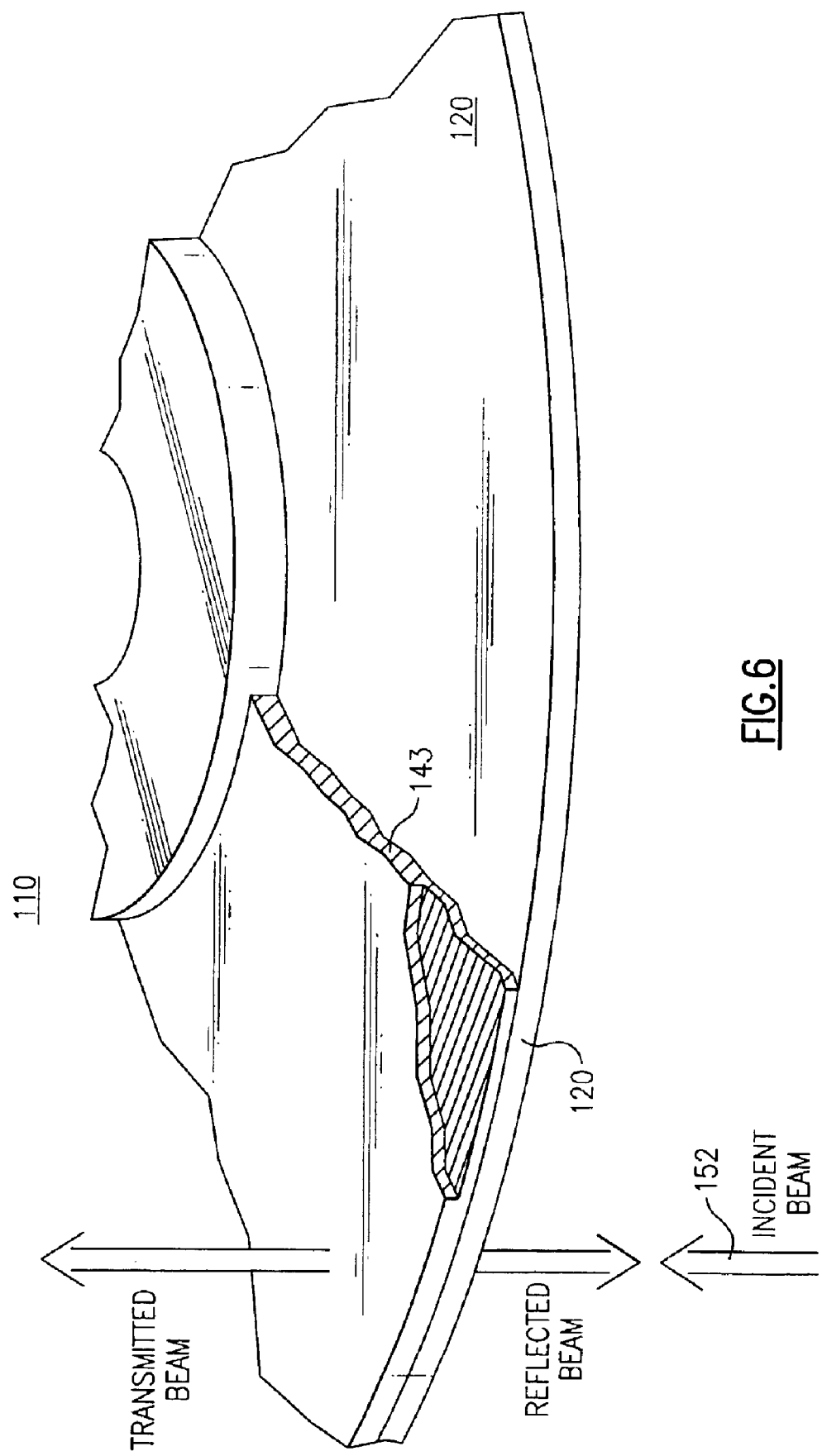
FIG. 6 is a perspective view representing the disc shown in FIG. 5 with a cut-away section illustrating the functional aspects of a semi-reflective layer of the disc.
Figure 9:
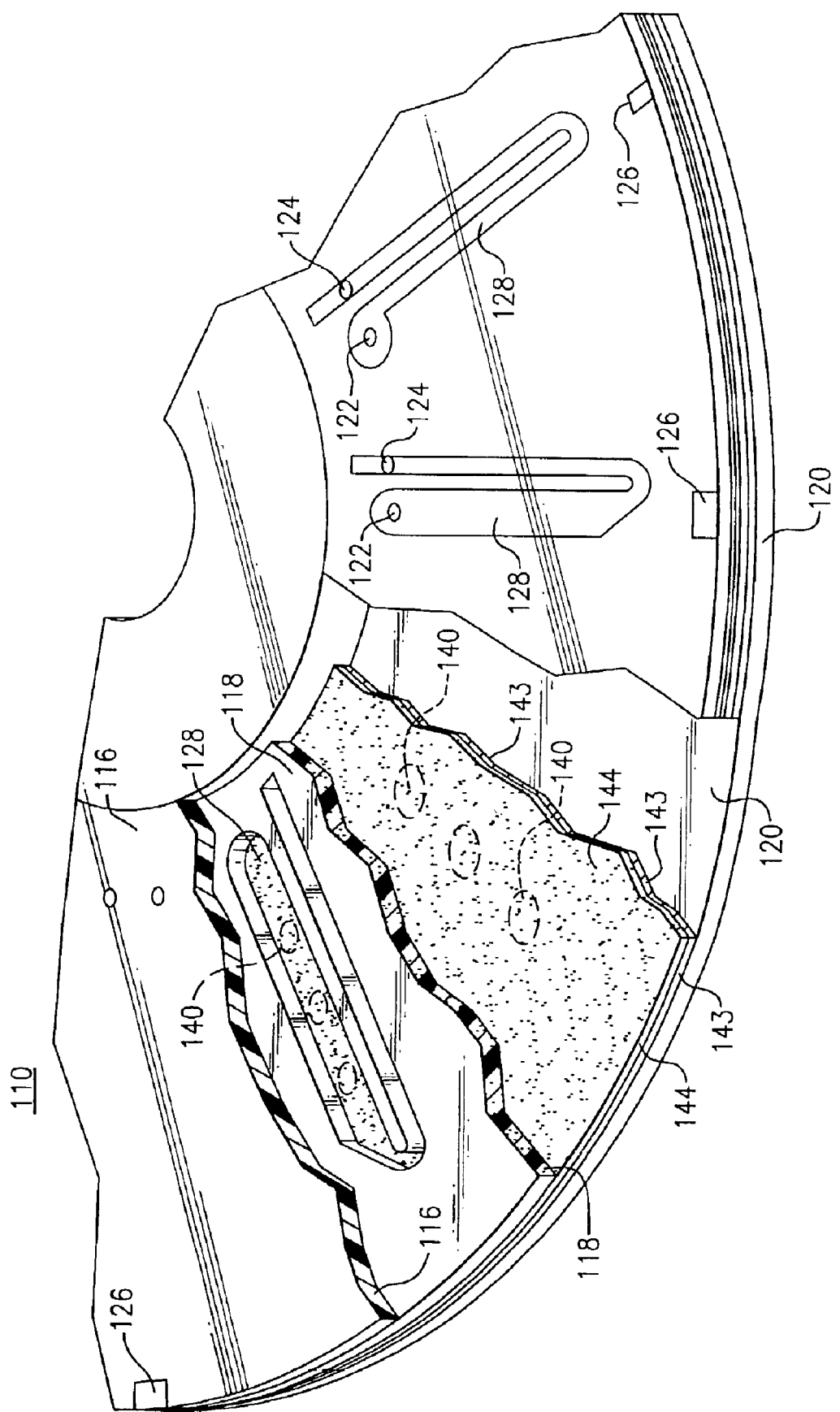
FIG. 9 is a perspective view of the disc illustrated in FIG. 5 with cut-away sections showing the different layers of the disc including the type of semi-reflective layer shown in FIG. 6.

Referring now to FIG. 5, there is shown an exploded perspective view of the principal structural elements of a transmissive type of optical bio-disc 110 according to the present invention. The principal structural elements of the transmissive type of optical bio-disc 110 similarly include the cap portion 116, the adhesive or channel member 118, and the substrate 120 layer. The cap portion 116 includes one or more inlet ports 122 and one or more vent ports 124. The cap portion 116 may be formed from a polycarbonate layer. Optional trigger markings 126 may be included on the surface of a thin semi-reflective layer 143, as best illustrated in FIGS. 6 and 9. Trigger markings 126 may include a clear window in all three layers of the bio-disc, an opaque area, or a reflective or semi-reflective area encoded with information that sends data to the processor 166, FIG. 10, which in turn interacts with the operative functions of the interrogation beam 152, FIGS. 6 and 10.

The second element shown in FIG. 5 is the adhesive member or channel layer 118 having fluidic circuits 128 or U-channels formed therein. The fluidic circuits 128 are formed by stamping or cutting the membrane to remove plastic film and form the shapes as indicated. Each of the fluidic circuits 128 includes the flow channel 130 and the return channel 132. Some of the fluidic circuits 128 illustrated in FIG. 5 include the mixing chamber 134. Two different types of mixing chambers 134 are illustrated. The first is the symmetric mixing chamber 136 that is symmetrically formed relative to the flow channel 130. The second is the off-set mixing chamber 138. The off-set mixing chamber 138 is formed to one side of the flow channel 130 as indicated.

Figure 12:
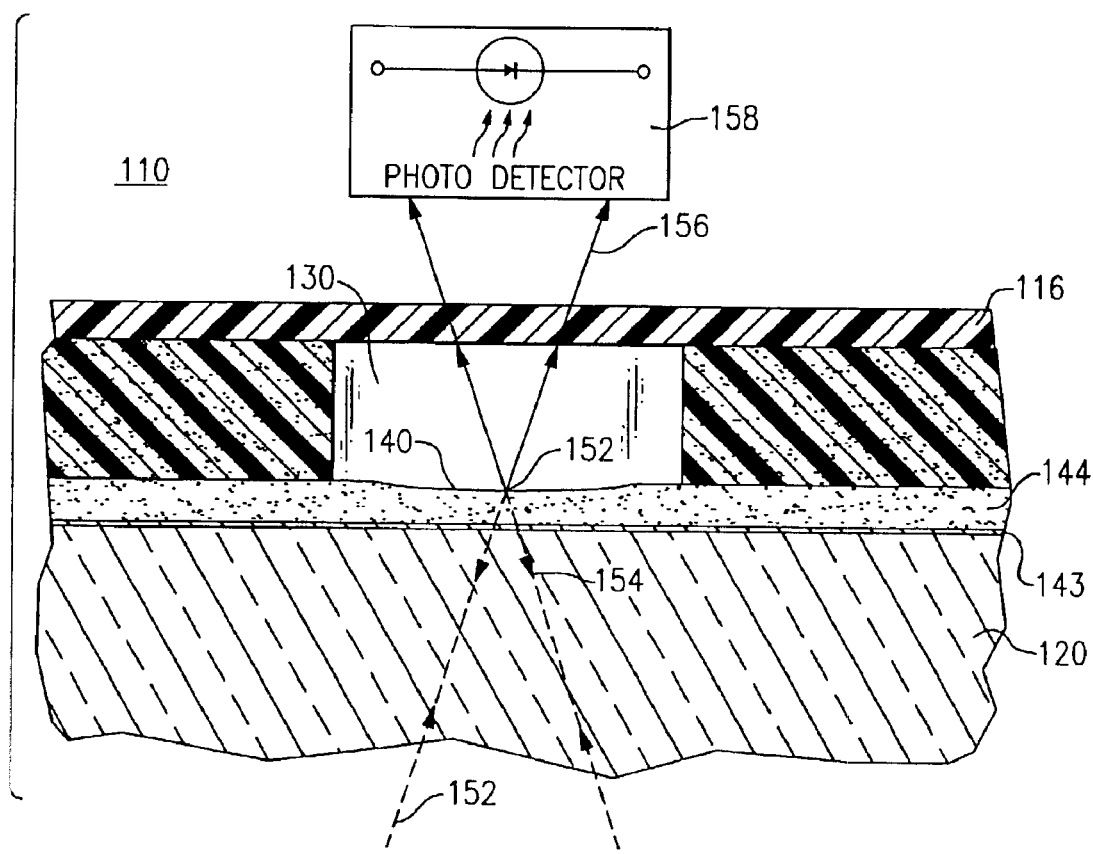
FIG. 12 is a partial cross sectional view taken perpendicular to a radius of the transmissive optical bio-disc illustrated in FIGS. 5, 8, and 9 showing a flow channel formed therein and a top detector.

The third element illustrated in FIG. 5 is the substrate 120 which may include the target or capture fields 140. The substrate 120 is preferably made of polycarbonate and has the thin semi-reflective layer 143 deposited on the top thereof, FIG. 6. The semi-reflective layer 143 associated with the substrate 120 of the disc 110 illustrated in FIGS. 5 and 6 is significantly thinner than the reflective layer 142 on the substrate 120 of the reflective disc 110 illustrated in FIGS. 2, 3 and 4. The thinner semi-reflective layer 143 allows for some transmission of the interrogation beam 152 through the structural layers of the transmissive disc as shown in FIGS. 6 and 12. The thin semi-reflective layer 143 may be formed from a metal such as aluminum or gold.

FIG. 6 is an enlarged perspective view of the substrate 120 and semi-reflective layer 143 of the transmissive embodiment of the optical bio-disc 110 illustrated in FIG. 5. The thin semi-reflective layer 143 may be made from a metal such as aluminum or gold. In the preferred embodiment, the thin semi-reflective layer 143 of the transmissive disc illustrated in FIGS. 5 and 6 is approximately 10–300 Å thick and does not exceed 400 Å. This thinner semi-reflective layer 143 allows a portion of the incident or interrogation beam 152 to penetrate and pass through the semi-reflective layer 143 to be detected by a top detector 158, FIGS. 10 and 12, while some of the light is reflected or returned back along the incident path. As indicated below, Table 1 presents the reflective and transmissive characteristics of a gold film relative to the thickness of the film. The gold film layer is fully reflective at a thickness greater than 800 Å. While the threshold density for transmission of light through the gold film is approximately 400 Å.

Figure 7:
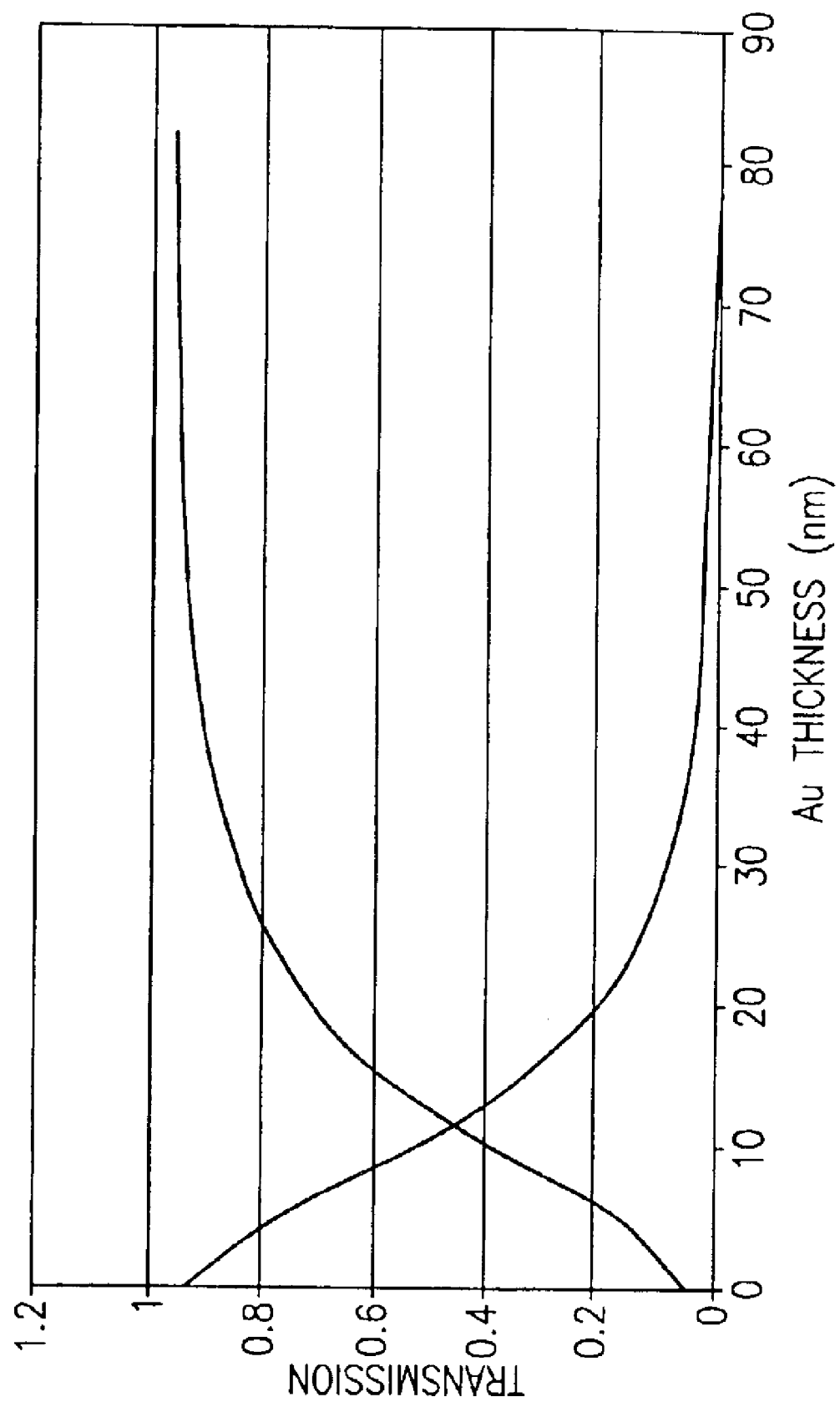
FIG. 7 is a graphical representation showing the relationship between thickness and transmission of a thin gold film.

In addition to Table 1, FIG. 7 provides a graphical representation of the inverse relationship of the reflective and transmissive nature of the thin semi-reflective layer 143 based upon the thickness of the gold. Reflective and transmissive values used in the graph illustrated in FIG. 7 are absolute values.

TABLE 1

Au film Reflection and Transmission (Absolute Values)

| Thickness (Angstroms) | Thickness (nm) | Reflectance | Transmittance |
| --- | --- | --- | --- |
| 0 | 0 | 0.0505 | 0.9495 |
| 50 | 5 | 0.1683 | 0.7709 |
| 100 | 10 | 0.3981 | 0.5169 |
| 150 | 15 | 0.5873 | 0.3264 |
| 200 | 20 | 0.7142 | 0.2057 |
| 250 | 25 | 0.7959 | 0.1314 |
| 300 | 30 | 0.8488 | 0.0851 |
| 350 | 35 | 0.8836 | 0.0557 |
| 400 | 40 | 0.9067 | 0.0368 |
| 450 | 45 | 0.9222 | 0.0244 |
| 500 | 50 | 0.9328 | 0.0163 |
| 550 | 55 | 0.9399 | 0.0109 |
| 600 | 60 | 0.9448 | 0.0073 |
| 650 | 65 | 0.9482 | 0.0049 |
| 700 | 70 | 0.9505 | 0.0033 |
| 750 | 75 | 0.9520 | 0.0022 |
| 800 | 80 | 0.9531 | 0.0015 |

Figure 8:
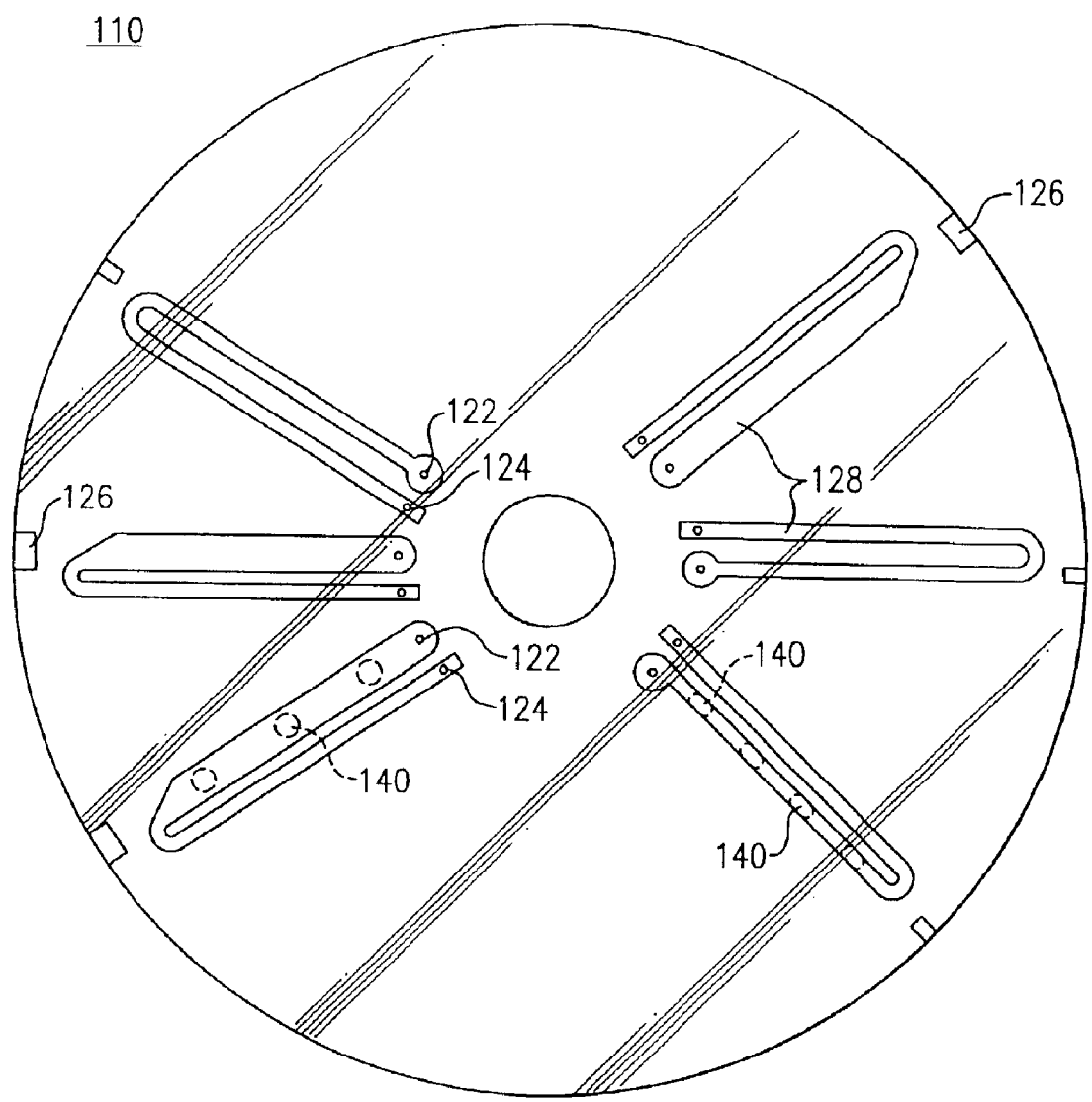
FIG. 8 is a top plan view of the disc shown in FIG. 5.

With reference next to FIG. 8, there is shown a top plan view of the transmissive type optical bio-disc 110 illustrated in FIGS. 5 and 6 with the transparent cap portion 116 revealing the fluidic channels, the trigger markings 126, and the target zones 140 as situated within the disc.

FIG. 9 is an enlarged perspective view of the optical bio-disc 110 according to the transmissive disc embodiment of the present invention. The disc 110 is illustrated with a portion of the various layers thereof cut away to show a partial sectional view of each principal layer, substrate, coating, or membrane. FIG. 9 illustrates a transmissive disc format with the clear cap portion 116, the thin semi-reflective layer 143 on the substrate 120, and trigger markings 126. In this embodiment, trigger markings 126 include opaque material placed on the top portion of the cap. Alternatively the trigger marking 126 may be formed by clear, non-reflective windows etched on the thin reflective layer 143 of the disc, or any mark that absorbs or does not reflect the signal coming from the trigger detector 160, FIG. 10. FIG. 9 also shows, the target zones 140 formed by marking the designated area in the indicated shape or alternatively in any desired shape. Markings to indicate target zone 140 may be made on the thin semi-reflective layer 143 on the substrate 120 or on the bottom portion of the substrate 120 (under the disc). Alternatively, the target zones 140 may be formed by a masking technique that includes masking the entire thin semi-reflective layer 143 except the target zones 140. In this embodiment, target zones 140 may be created by silk screening ink onto the thin semi-reflective layer 143. In the transmissive disc format illustrated in FIGS. 5, 8, and 9, the target zones 140 may alternatively be defined by address information encoded on the disc. In this embodiment, target zones 140 do not include a physically discernable edge boundary.

The substrate layer may be impressed with a spiral track that starts at an innermost readable portion of the disc and then spirals out to an outermost readable portion of the disc. In a non-recordable CD, this track is made up of a series of embossed pits with varying length, each typically having a depth of approximately one-quarter the wavelength of the light that is used to read the disc. The varying lengths and spacing between the pits encode the operational data. The spiral groove of a recordable CD-like disc has a detectable dye rather than pits. This is where the operation information, such as the rotation rate, is recorded. Depending on the test, assay, or investigational protocol, the rotation rate may be variable with intervening or consecutive periods of acceleration, constant speed, and deceleration. These periods may be closely controlled both as to speed and time of rotation to provide, for example, mixing, agitation, or separation of fluids and suspensions with agents, reagents, antibodies, or other materials.

With continuing reference to FIG. 9, an active layer 144 is illustrated as applied over the thin semi-reflective layer 143. In the preferred embodiment, the active layer 144 is a 40 to 200 µm thick layer of 2% polystyrene. Alternatively, polycarbonate, gold, activated glass, modified glass, or modified polystyrene, for example, polystyrene-co-maleic anhydride, may be used. In addition, hydrogels can be used. As illustrated in this embodiment, the plastic adhesive member 118 is applied over the active layer 144. The exposed section of the plastic adhesive member 118 illustrates the cut out or stamped U-shaped form that creates the fluidic circuits 128.

The final principal structural layer in this transmissive embodiment of the present bio-disc 110 is the clear, non-reflective cap portion 116 that includes inlet ports 122 and vent ports 124.

Figure 10:
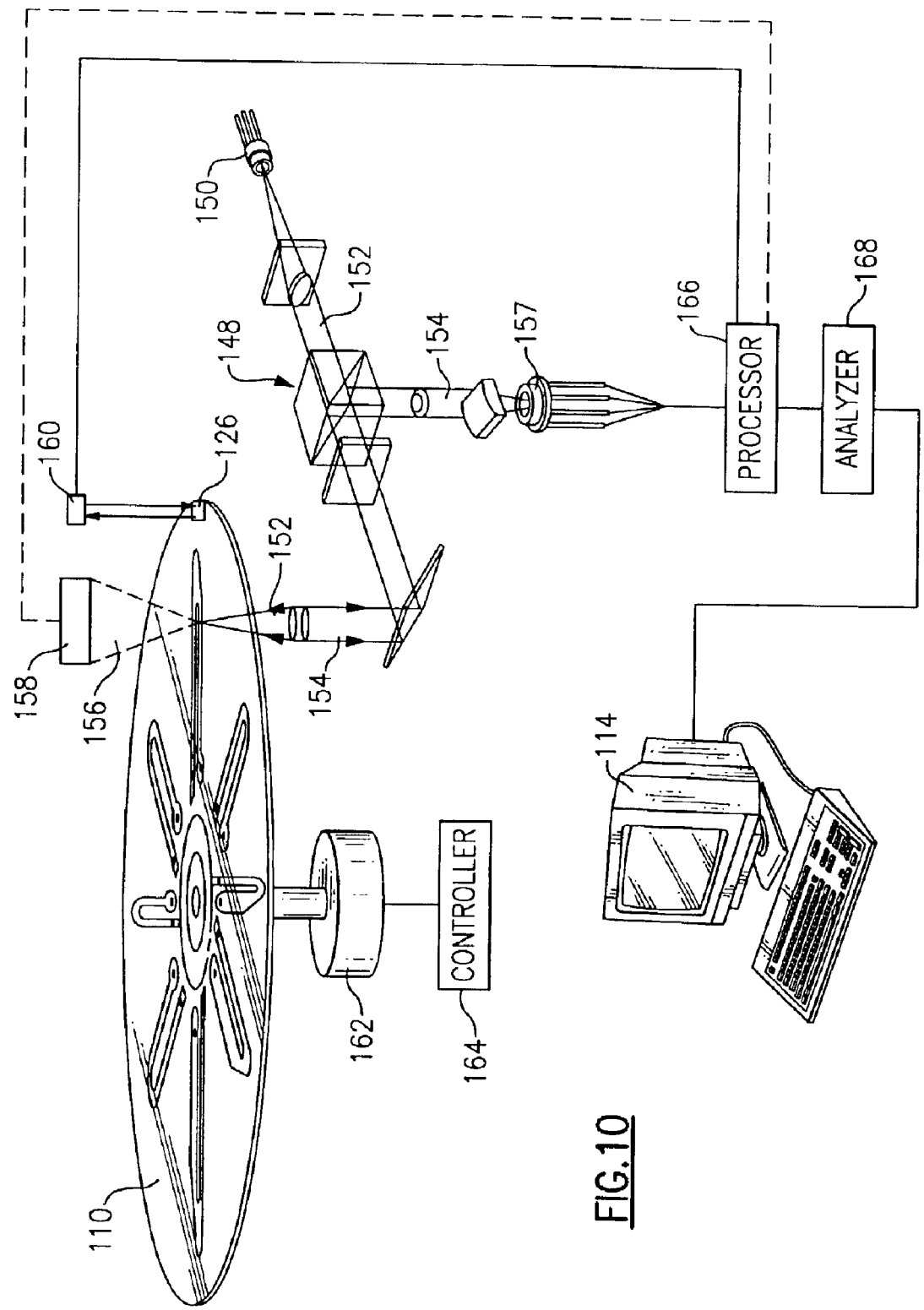
FIG. 10 is a perspective and block diagram representation illustrating the system of FIG. 1 in more detail.

Referring next to FIG. 10, there is shown an optical disc reader system. This system may be a conventional reader for CD, CD-R, DVD, DVD-R or other known comparable optical disc format, a modified version of such a drive, or a completely distinct dedicated device. The basic components are a motor for rotating the disc, a light system for providing light, and a detection system for detecting light.

FIG. 10 is a perspective block diagram of an optical disc reader illustrating optical components 148, a light source 150 that produces the incident or interrogation beam 152, a return beam 154, and a transmitted beam 156. In the case of the reflective bio-disc illustrated in FIG. 4, the return beam 154 is reflected from the reflective surface 146 of the cap portion 116 of the optical bio-disc 110. In this reflective embodiment of the present optical bio-disc 110, the return beam 154 is detected and analyzed for the presence of signal elements by a bottom detector 157. In the transmissive bio-disc format, on the other hand, the transmitted beam 156 is detected, by a top detector 158, and is also analyzed for the presence of signal elements. In the transmissive embodiment, a photo detector may be used as a top detector 158.

FIG. 10 also shows a hardware trigger mechanism that includes the trigger markings 126 on the disc and a trigger detector 160. The hardware triggering mechanism is used in both reflective bio-discs (FIG. 4) and transmissive bio-discs (FIG. 9). The triggering mechanism allows the processor 166 to collect data only when the interrogation beam 152 is on a respective target zone 140. Furthermore, in the transmissive bio-disc system, a software trigger may also be used. The software trigger uses the bottom detector to signal the processor 166 to collect data as soon as the interrogation beam 152 hits the edge of a respective target zone 140. FIG. 10 further illustrates a drive motor 162 and a controller 164 for controlling the rotation of the optical bio-disc 110. FIG. 10 also shows the processor 166 and analyzer 168 implemented in the alternative for processing the return beam 154 and transmitted beam 156 associated the transmissive optical bio-disc.

Numerous designs and configurations of an optical pickup and associated electronics may be used in the context of the embodiments of the present invention. Further details and alternative designs for compact discs and readers are described in Compact Disc Technology, by Nakajima and Ogawa, IOS Press, Inc. (1992); The Compact Disc Handbook, Digital Audio and Compact Disc Technology, by Baert et al. (eds.), Books Britain (1995); and CD-ROM Professional's CD-Recordable Handbook: The Complete Guide to Practical Desktop CD, Starrett et al. (eds.), ISBN:0910965188 (1996); all of which are incorporated herein in their entirety by reference.

The disc drive assembly is thus employed to rotate the disc, read and process any encoded operational information stored on the disc, analyze the liquid, chemical, biological, or biochemical investigational features in an assay region of the disc, to write information to the disc either before or after the material in the assay zone is analyzed by the read beam of the drive or deliver the information via various possible interfaces, such as Ethernet to a user, database, or anywhere the information could be utilized.

Figure 11:
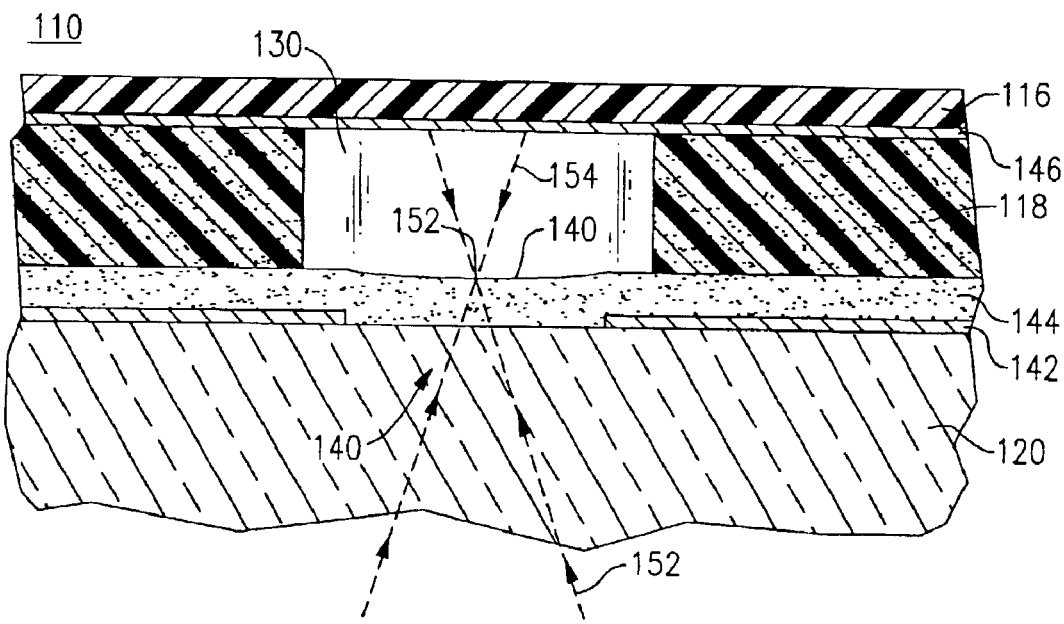
FIG. 11 is a partial cross sectional view taken perpendicular to a radius of the reflective optical bio-disc illustrated in FIGS. 2, 3, and 4 showing a flow channel formed therein.

As shown in FIG. 11, there is presented a partial cross sectional view of the reflective disc embodiment of the optical bio-disc 110 according to the present invention. FIG. 11 illustrates the substrate 120 and the reflective layer 142. As indicated above, the reflective layer 142 may be made from a material such as aluminum, gold or other suitable reflective material. In this embodiment, the top surface of the substrate 120 is smooth. FIG. 11 also shows the active layer 144 applied over the reflective layer 142. As also shown in FIG. 11, the target zone 140 is formed by removing an area or portion of the reflective layer 142 at a desired location or, alternatively, by masking the desired area prior to applying the reflective layer 142. As further illustrated in FIG. 11, the plastic adhesive member 118 is applied over the active layer 144. FIG. 11 also shows the cap portion 116 and the reflective surface 146 associated therewith. Thus when the cap portion 116 is applied to the plastic adhesive member 118 including the desired cutout shapes, flow channel 130 is thereby formed. As indicated by the arrowheads shown in FIG. 11, the path of the incident beam 152 is initially directed toward the substrate 120 from below the disc 110. The incident beam then focuses at a point proximate the reflective layer 142. Since this focusing takes place in the target zone 140 where a portion of the reflective layer 142 is absent, the incident continues along a path through the active layer 144 and into the flow channel 130. The incident beam 152 then continues upwardly traversing through the flow channel to eventually fall incident onto the reflective surface 146. At this point, the incident beam 152 is returned or reflected back along the incident path and thereby forms the return beam 154.

FIG. 12 is a partial cross sectional view of the transmissive embodiment of the bio-disc 110 according to the present invention. FIG. 12 illustrates a transmissive disc format with the clear cap portion 116 and the thin semi-reflective layer 143 on the substrate 120. FIG. 12 also shows the active layer 144 applied over the thin semi-reflective layer 143. In the preferred embodiment, the transmissive disc has the thin semi-reflective layer 143 made from a metal such as aluminum or gold approximately 100–300 Angstroms thick and does not exceed 400 Angstroms. This thin semi-reflective layer 143 allows a portion of the incident or interrogation beam 152, from the light source 150, FIG. 10, to penetrate and pass upwardly through the disc to be detected by a top detector 158, while some of the light is reflected back along the same path as the incident beam but in the opposite direction. In this arrangement, the return or reflected beam 154 is reflected from the semi-reflective layer 143. Thus in this manner, the return beam 154 does not enter into the flow channel 130. The reflected light or return beam 154 may be used for tracking the incident beam 152 on pre-recorded information tracks formed in or on the semi-reflective layer 143 as described in more detail in conjunction with FIGS. 13 and 14. In the disc embodiment illustrated in FIG. 12, a physically defined target zone 140 may or may not be present. Target zone 140 may be created by direct markings made on the thin semi-reflective layer 143 on the substrate 120. These marking may be formed using silk screening or any equivalent method. In the alternative embodiment where no physical indicia are employed to define a target zone (such as, for example, when encoded software addressing is utilized) the flow channel 130 in effect may be employed as a confined target area in which inspection of an investigational feature is conducted.

Figure 13:
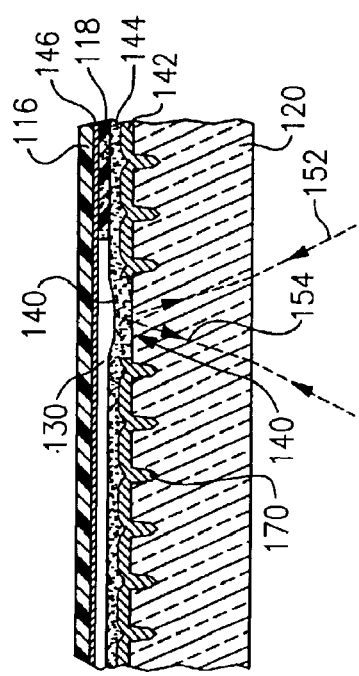
FIG. 13 is a partial longitudinal cross sectional view of the reflective optical bio-disc shown in FIGS. 2, 3, and 4 illustrating a wobble groove formed therein.

FIG. 13 is a cross sectional view taken across the tracks of the reflective disc embodiment of the bio-disc 110 according to the present invention. This view is taken longitudinally along a radius and flow channel of the disc. FIG. 13 includes the substrate 120 and the reflective layer 142. In this embodiment, the substrate 120 includes a series of grooves 170. The grooves 170 are in the form of a spiral extending from near the center of the disc toward the outer edge. The grooves 170 are implemented so that the interrogation beam 152 may track along the spiral grooves 170 on the disc. This type of groove 170 is known as a "wobble groove". A bottom portion having undulating or wavy sidewalls forms the groove 170, while a raised or elevated portion separates adjacent grooves 170 in the spiral. The reflective layer 142 applied over the grooves 170 in this embodiment is, as illustrated, conformal in nature. FIG. 13 also shows the active layer 144 applied over the reflective layer 142. As shown in FIG. 13, the target zone 140 is formed by removing an area or portion of the reflective layer 142 at a desired location or, alternatively, by masking the desired area prior to applying the reflective layer 142. As further illustrated in FIG. 13, the plastic adhesive member 118 is applied over the active layer 144. FIG. 13 also shows the cap portion 116 and the reflective surface 146 associated therewith. Thus, when the cap portion 116 is applied to the plastic adhesive member 118 including the desired cutout shapes, the flow channel 130 is thereby formed.

Figure 14:
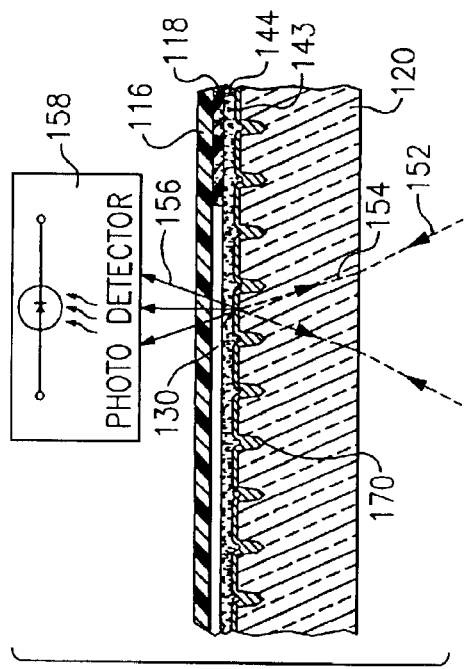
FIG. 14 is a partial longitudinal cross sectional view of the transmissive optical bio-disc illustrated in FIGS. 5, 8, and 9 showing a wobble groove formed therein and a top detector.

FIG. 14 is a cross sectional view taken across the tracks of the transmissive disc embodiment of the bio-disc 110 according to the present invention as described in FIG. 12, for example. This view is taken longitudinally along a radius and flow channel of the disc. FIG. 14 illustrates the substrate 120 and the thin semi-reflective layer 143. This thin semi-reflective layer 143 allows the incident or interrogation beam 152, from the light source 150, to penetrate and pass through the disc to be detected by the top detector 158, while some of the light is reflected back in the form of the return beam 154. The thickness of the thin semi-reflective layer 143 is determined by the minimum amount of reflected light required by the disc reader to maintain its tracking ability. The substrate 120 in this embodiment, like that discussed in FIG. 13, includes the series of grooves 170. The grooves 170 in this embodiment are also preferably in the form of a spiral extending from near the center of the disc toward the outer edge. The grooves 170 are implemented so that the interrogation beam 152 may track along the spiral. FIG. 14 also shows the active layer 144 applied over the thin semi-reflective layer 143. As further illustrated in FIG. 14, the plastic adhesive member or channel layer 118 is applied over the active layer 144. FIG. 14 also shows the cap portion 116 without a reflective surface 146. Thus, when the cap is applied to the plastic adhesive member 118 including the desired cutout shapes, the flow channel 130 is thereby formed and a part of the incident beam 152 is allowed to pass therethrough substantially unreflected.

Figure 16:
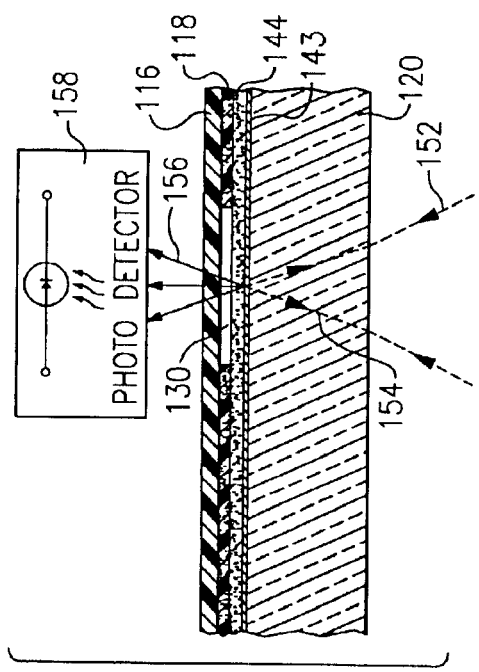
FIG. 16 is a view similar to FIG. 12 showing the entire thickness of the transmissive disc and the initial refractive property thereof.
Figure 15:
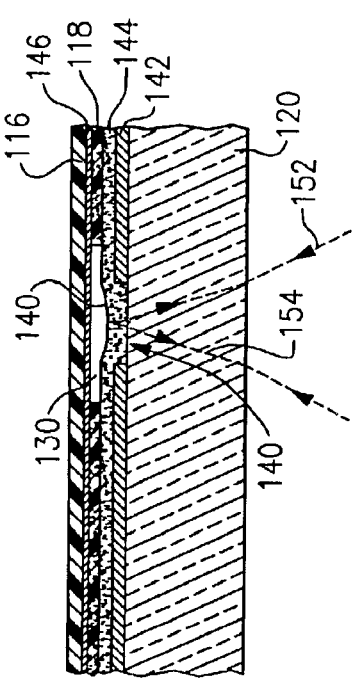
FIG. 15 is a view similar to FIG. 11 showing the entire thickness of the reflective disc and the initial refractive property thereof.

FIG. 15 is a view similar to FIG. 11 showing the entire thickness of the reflective disc and the initial refractive property thereof. FIG. 16 is a view similar to FIG. 12 showing the entire thickness of the transmissive disc and the initial refractive property thereof. Grooves 170 are not seen in FIGS. 15 and 16 since the sections are cut along the grooves 170. FIGS. 15 and 16 show the presence of the narrow flow channel 130 that is situated perpendicular to the grooves 170 in these embodiments. FIGS. 13, 14, 15, and 16 show the entire thickness of the respective reflective and transmissive discs. In these figures, the incident beam 152 is illustrated initially interacting with the substrate 120 which has refractive properties that change the path of the incident beam as illustrated to provide focusing of the beam 152 on the reflective layer 142 or the thin semi-reflective layer 143.

The invention is described below as it relates to clinical diagnostic assays based on cell-capture and/or cell separation technologies as employed on an optical bio-disc described herein. Various embodiments of this aspect of the invention are directed to blood-typing and antibody typing diagnostic assays.

Blood Typing Assays

Figure 17:
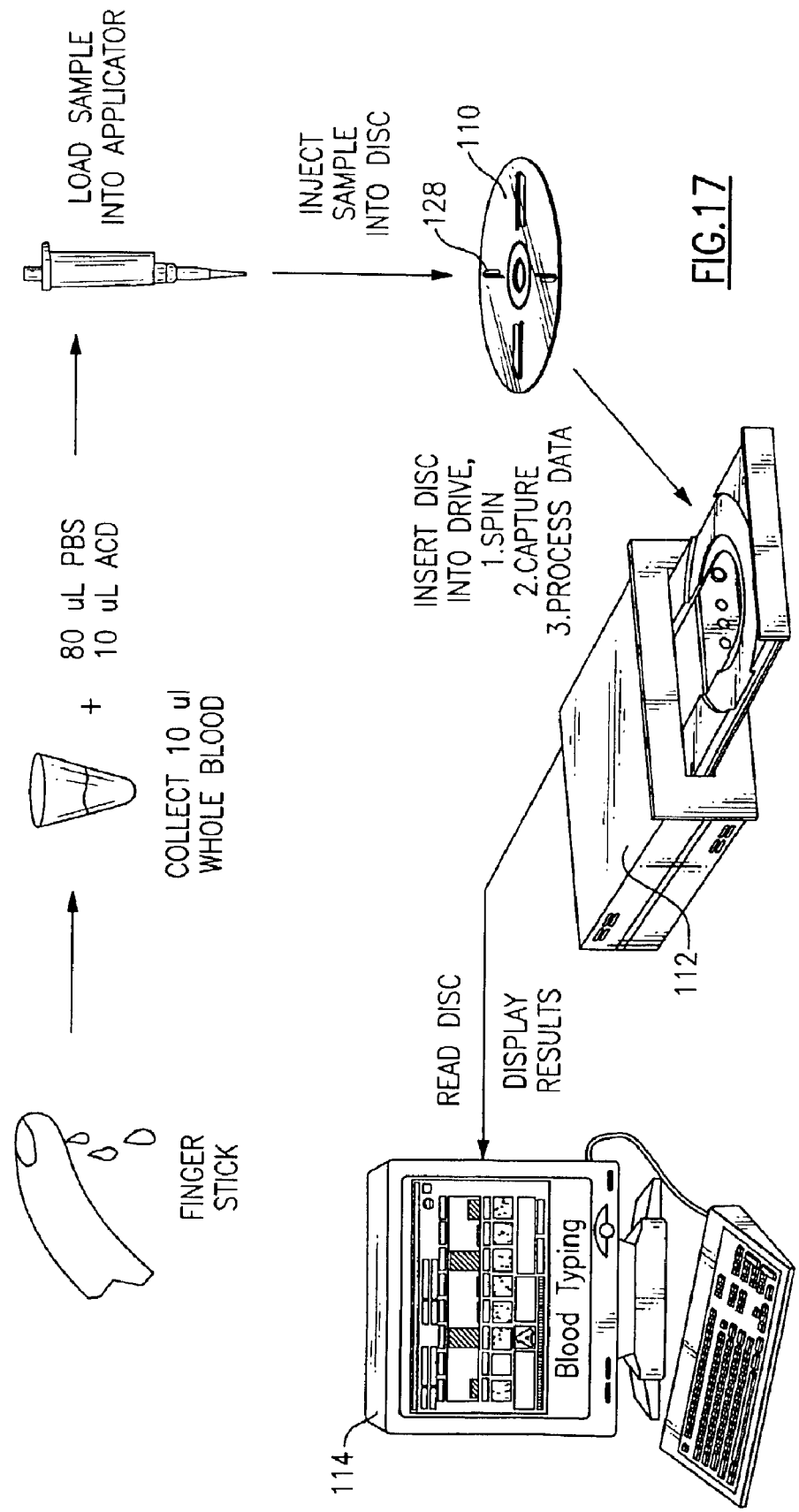
FIG. 17 is a pictorial flow diagram presenting one example of a forward ABO/Rh blood typing method of the invention.

Referring to FIG. 17, there is illustrated a system for blood typing or the detection of antibodies directed against a particular blood type. The system includes methods for the collection and processing of blood for diagnostic purposes. In the embodiment presented, whole blood may be collected by standard finger stick. Ten microliters of this sample is then diluted with 80 microliters of phosphate buffered saline (PBS) and 10 microliters of an anticoagulent (e.g., heparin or ACD). The diluted sample is then introduced through the inlet port 122 into the optical bio-disc 110. The optical bio-disc can be a reflective disc (FIG. 4) or transmissive disc (FIG. 9). The optical bio-disc has at least one chamber with a target zone 140 and capture fields contained therein. After a sufficient incubation period, e.g. 5 minutes, the optical bio-disc is loaded onto an optical disc reader 112 and the disc is spun for approximately 5 minutes. At the end of the spin, the disc is then analyzed and the information is collected and transferred to a system for the data processing. After processing the collected data, results of the diagnostic assay are transferred to a monitor 114 to display output results. Additional details are provided in Example 2. An advantage of the system of the present invention, for example, is that the optical bio-disc and disc reader assembly allows a person to carry out blood typing analysis in the field (that is, not in a clinical setting) expeditiously.

In various aspects of the invention, a sample is loaded into a chamber within the optical bio-disc, having a capture field with one or more bioactive capture agents affixed thereto. The bio-disc is then subjected to conditions suitable for cell binding. Then, the bio-disc is placed into a CD drive assembly and is spun radially at a speed sufficient to separate unbound cells from bound cells, e.g., about 1000 rpm to about 4000 rpm for about one to five minutes. This spinning causes the cells that are not bound by the capture agent to be removed from the capture fields and collected in a separate part of the chamber (e.g., in a waste receptacle in the chamber).

As used herein, the term "capture field" encompasses target zone or capture zone 140 of an optical bio-disc, which has attached thereto, either directly or indirectly, a capture agent. The capture field is a discrete location on the surface having defined limits, metes and bounds.

As used herein, the term "capture agent" refers to any molecule A located on the surface of the capture field that recognizes any molecule B, and binds with specificity thereto. The phrase "binds with specificity" is meant herein to refer to the binding of molecule A to molecule B by at least two fold, at least five fold, at least 10 fold, at least one hundred fold, at least 1000 fold, at least 10,000 fold or more when compared to other molecules that may be present in a biological sample. By way of non-limiting example, molecules that specifically recognize and bind to other molecules include antibodies, ligands, receptors, enzymes, substrates, biotin, avidin, and lectins. The bioactive agent of the invention may be obtained from any source, including but not limited to viral, bacterial, fungal, plant, animal, in vitro or synthetically produced materials.

In certain embodiments of the invention, the capture agent is a capture antibody and the capture field has at least one capture antibody bound thereto. As used herein, the term "antibody" includes polyclonal, monoclonal, and recombinantly created antibodies. Antibodies of the invention can be produced in vivo or in vitro. Methods for the production of antibodies are well known to those skilled in the art. For example, see *Antibody Production: Essential Techniques*, Peter Delves (Ed.), John Wiley & Son Ltd, ISBN: 0471970107 (1997). Alternatively, antibodies may be obtained from commercial sources, e.g., Research Diagnostics Inc., Pleasant Hill Road, Flanders, N.J. 07836 and Ortho Diagnostic Systems)

The selection of a capture agent to be bound to a capture field is within the skill of those in the art. By way of non-limiting example, a receptor-specific ligand may be bound to a capture field for the purpose of binding cells expressing the receptor recognized by the ligand or a capture field may be bound by a lectin that binds specifically a sugar moiety expressed on the surface of a select population of cells for the purpose of binding those cells. Alternatively, the capture field may be bound by a capture antibody specific for a receptor on the surface of a cell. Thus, the invention provided herein is easily adapted to any number of biological assays. Related aspects regarding binding capture agents onto solid support, such as an optical disc substrate, is disclosed in, for example, commonly assigned U.S. patent application Ser. No. 10/194,396 entitled "Multi-Purpose Optical Analysis Disc For Conducting Assays And Various Reporting Agents For Use Therewith" filed Jul. 12, 2002, which is herein incorporated by reference in its entirety.

The term "antibody" is not meant to be limited to antibodies of any one particular species, e.g., human, mouse, rat, goat, etc., are all contemplated by the invention. The term "antibody" is also inclusive of any class or subclass of antibodies, as all antibody types may be used to bring about an agglutination reaction. By way of non-limiting example, the IgG antibody class may be used for agglutination purposes or, if higher antibody polyvalency is desired, the IgM class of antibodies may be utilized for the same purpose. Other types of immunoglobulins that bind specifically to cells are also included within the scope of the invention. Antibody fragments can also be utilized as a capture agent of the invention. The use of antibodies in the art of medical diagnostics is well known to those skilled in the art. For example, see Diagnostic and Therapeutic Antibodies (Methods in Molecular Medicine), Andrew J. T. George and Catherine E. Urch (Eds.), Humana Press; ISBN: 0896037983 (2000) and Antibodies in Diagnosis and Therapy: Technologies, Mechanisms and Clinical Data (Studies in Chemistry Series), Siegfried Matzku and Rolf A. Stahel (Eds.), Harwood Academic Pub.; ISBN: 9057023105 (1999), which are incorporated herein in their entirely by reference.

The capture field with the capture agent bound thereto can be structured in any way suitable to bind cells. In certain embodiments of the invention, one or more capture agents can be directly linked to the capture field. Thus, capture fields may be uniformly bound with multiple copies of a single capture agent or, alternatively, capture fields may be bound with multiple copies of two or more capture agents to increase the specificity of the binding reaction. In other embodiments, the capture agent can be indirectly linked to the capture field. By way of non-limiting example, a capture field may be coated with a protein such as streptavidin and a capture agent such as an antibody can be linked to the streptavidin by way of a biotin moiety attached to the antibody.

In certain embodiments of the invention, the capture field of the invention has a first capture agent bound thereto and the first capture agent binds a second capture agent. By way of non-limiting example, an anti-IgM IgG antibody can serve as a first capture agent bound to a capture field, which itself binds an IgM antibody, the second capture agent. Thus, the capture agent bound to a capture field can in certain embodiments comprise more than one capture agent linked to one another in tandem.

In various aspects of the invention, the capture agents may be attached to the capture field in different ways. By way of non-limiting example, various constructions are presented in Table 2. Table 2 also demonstrates that different target zones or fields (i.e., windows) can be constructed with different capture agents on the same or different optical bio-discs. In one embodiment, a capture antibody can be attached directly to the bio-disc. In other embodiments, one or more additional agents are utilized as intermediate binding agents between the optical bio-disc and the capture agent located most distally thereto. This latter design reduces steric hindrance, thereby improving the likelihood that the capture agent will function sufficiently.

Some embodiments depicted in Table 2 take advantage of the known strong molecular interaction between streptavidin, or variants thereof, and biotin. By way of non-limiting example, streptavidin can be utilized as an initial layer in the capture field. By utilizing a biotinylated capture antibody, specific attachment to the streptavidin layer can be achieved by way of the molecular recognition between streptavidin and biotin and the strong binding resulting therefrom. If it is advantageous to further limit steric hindrance, a biotinylated first capture antibody can be bound to the streptavidin layer, and a second capture antibody that is specifically recognized and bound by the biotinylated first antibody can be applied.

("*Bioconjugate Techniques,*" Greg T. Hermanson, Academic Press, San Diego, Calif., (1996)).

Cross-linking agents include, but are not limited to homobifunctional linkers, heterobifunctional linkers, and zero-length cross-linkers. Homobifunctional linkers are linkers with two reactive sites of the same functionality, such as glutaraldehyde. These reagents could tie one protein to another by covalently reacting with the same common groups on both molecules. Heterobifunctional conjugation reagents contain two different reactive groups that can couple to two different functional targets on proteins and other macromolecules. For example, one part of a cross-linker may contain an amine-reactive group, while another portion may consist of a sulfhydryl-reactive group. The result is the ability to direct the cross-linking reaction to selected parts of target molecules, thus garnering better control over the conjugation process. Zero-length cross-linkers mediate the conjugation of two molecules by forming a bond containing no additional atoms. Thus, one atom

TABLE 2

Capture Layer Assembly and Variations

| | Window | | | | | | | |
|---|---|---|---|---|---|---|---|---|
| | 1 | 2 | 3 | 4 | 5 | 6 | 7 | 8 |
| Optional Initial Layer | Strep-tavidin | Strep-tavidin | Strep-tavidin | Strep-tavidin | Strep-tavidin | Strep-tavidin | Strep-tavidin | Strep-tavidin |
| Optional 1$^{st}$ Capture Antibody* | Anti-IgX Antibody | Anti-IgX Antibody | Anti-IgX Antibody | Anti-IgX Antibody | Anti-IgX Antibody | Anti-IgX Antibody | Anti-IgX Antibody | Anti-IgX Antibody |
| 2$^{nd}$ Capture Antibody | Anti-A Antibody | Anti-B Antibody | Anti-D Antibody | Anti-C Antibody | Anti-c Antibody | Anti-E Antibody | Anti-e Antibody | Anti-C$^w$ Antibody |

*Indicates that the capture antibody directly interacting with streptavidin is biotinylated.
IgX refers to any antibody immunoglobulin, e.g., IgG, IgM, etc.

Referring now to FIG. 18, there is presented alternative capture technologies of the invention that are not reliant upon streptavidin/biotin interaction. As shown in the bottom row of FIG. 18, in the simplest embodiment a capture agent is attached directly to the optical bio-disc capture field. Capture agents include, but are not limited to, molecules such as IgG, IgM, a lectin, or other molecules. Because steric hindrance may prevent a capture agent linked directly to an optical bio-disc from functioning optimally, an alternative embodiment is to attach the capture agent to the bio-disc by way of an intermediate linker molecule (or cross-linker). Such cross-linkers are known in the art. By way of non-limiting example, any carbon compound having a sufficient number of carbon atoms to provide the requisite length to minimize or eliminate problems associated with steric hindrance will suffice.

It should be understood that a cross-linking system involves one or more cross-linking agents, or conjugates, to cross-link one or more macromolecular moieties to another. A cross-link may be a covalent or non-covalent interaction between two macromolecular moieties, usually formed when two macromolecular free radicals combine. Chemical modifications or conjugation processes to achieve cross-links involve the reaction of one functional group with another, resulting in the formation of a bond. The creation of bioconjugate reagents with reactive or selectively reactive functional groups forms the basis for simple and reproducible cross-linking or tagging of target molecules of a molecule is covalently attached to an atom of a second molecule with no intervening linker or spacer. One of ordinary skill in the art would refer to "*Bioconjugate Techniques,*" Greg T. Hermanson, Academic Press, San Diego, Calif., (1996), for a detailed description of cross-linking agents.

In the present invention, cross-linking agents are bound to the surface of a bio-disc to immobilize capture agents within the target zones. A preferred cross-linking system is the heterobifunctional group consisting of biotin-streptavidin, i.e. biotinylated capture agents bound to an avidin-coupled substrate.

Other embodiments of the capture technology designed to reduce or eliminate steric hindrance are presented in the middle and top row of FIG. 18. These methodologies utilize either IgM or IgG as an intermediate binding molecule between the optical bio-disc and the capture agent. Capture agents include IgG, IgM, a lectin, or any other molecule that binds cells for the purpose of capture.

Figure 19:
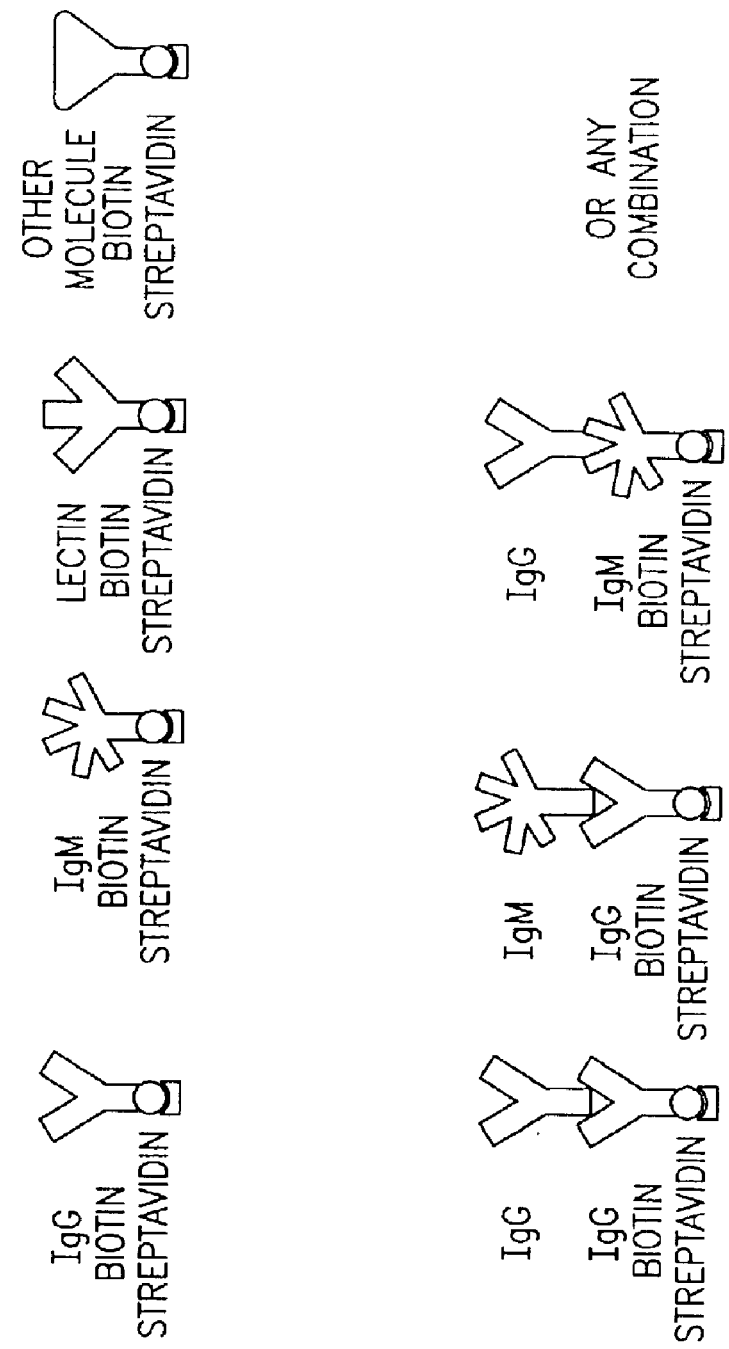
FIG. 19 is a pictorial schematic presenting the biotin/streptavidin-based cell capture technologies of the invention.

Referring to FIG. 19, cell capture technology of the invention based on the strong recognition and binding of streptavidin (or variants thereof) and biotin molecules to each other is presented. As previously detailed in Table 2, the bioactive agent streptavidin can be first applied to the capture field and used to bind and hold various capture agents, e.g., biotinylated IgG or biotinylated IgM or biotinylated lectin or any other cell binding molecule that is biotinylated. Various embodiments following this design are presented pictorially by the top row of FIG. 19. Alternative embodiments are presented pictorially in the bottom row of FIG. 19, wherein molecules such as IgG or IgM are used as agents serving an intermediary function for the binding of the aforementioned capture agents to a streptavidin layer on the optical bio-disc. In these embodiments, the intermediary function served by IgG and IgM is to reduce or eliminate problems associated with steric hindrance, analogous to the function served by the linker molecule discussed in relation to capture technologies presented in FIG. 18.

An optical bio-disc of the invention can have multiple capture fields within one chamber. A grouping of several capture fields is termed a "bar code" because the data resulting from cells binding to certain capture fields resembles the dark and light striped pattern known as a bar code. In another example, also incorporated within such a bar code are defined negative control areas and positive control areas.

Figure 20:
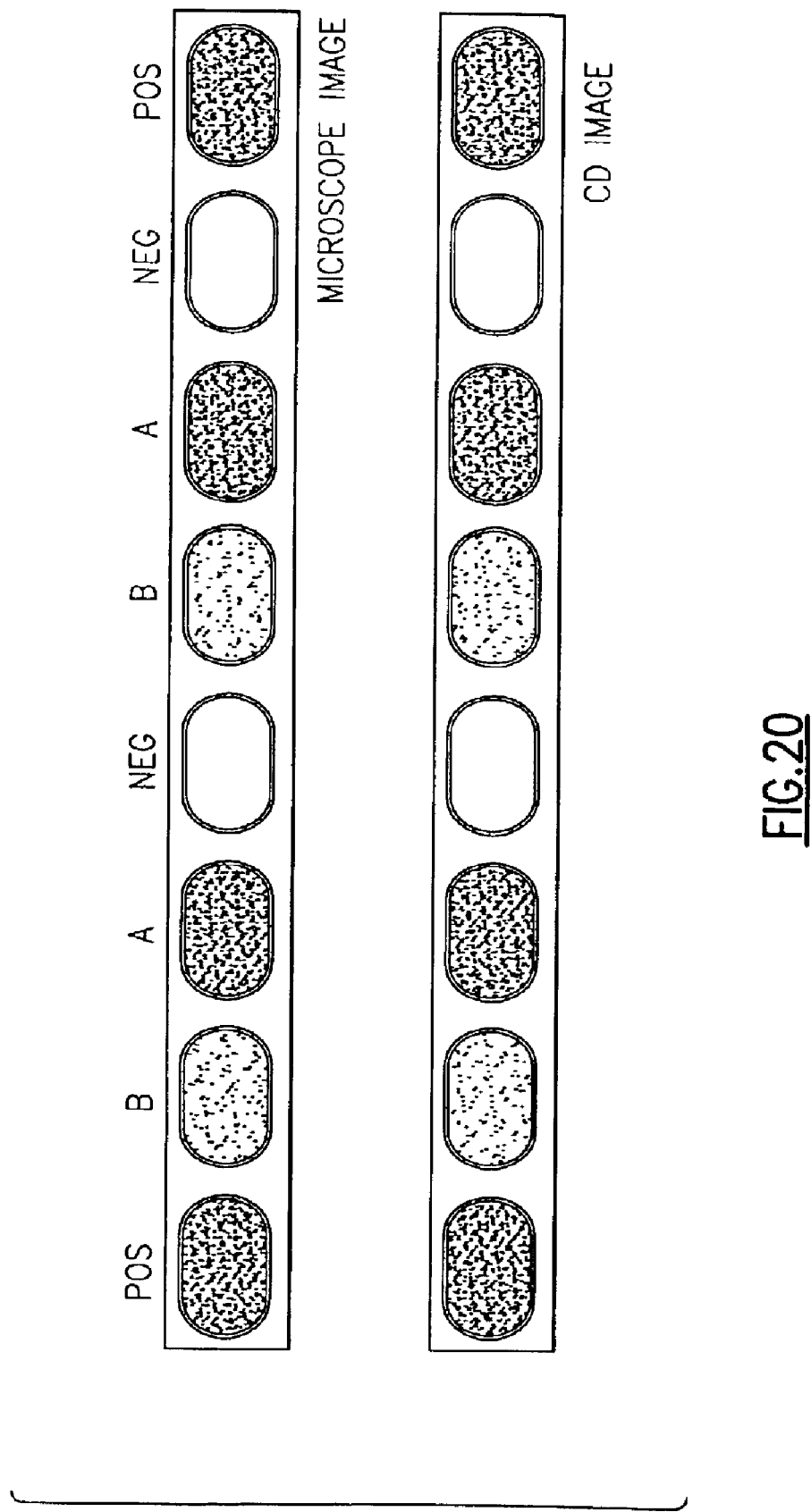
FIG. 20 is a plan view illustrating data output in the form of a bar code.

Referring now to FIG. 20, there are shown results of an exemplary assay method of the invention for forward blood typing. The method utilizes multiple capture fields that are conveniently designed into a "bar code" format for sample testing and data presentation. In the embodiment presented in FIG. 20, the optical bio-disc contains several capture fields, each of which has affixed thereto a capture agent, e.g., antibody, which is specific for a particular ABO antigenic determinant on the surface of a red blood cell (anti-A and anti-B antibodies may be obtained from Fisher Scientific, Los Angles, Calif., Catalogue Nos. 23287247 and 23287248, respectively). In addition, specific capture fields are designed as positive (POS) and negative (NEG) controls. Positive and negative controls for the test would include a positive control capture field in which the capture agent is a molecule that binds all cells, e.g., a lectin isolated from *Lycopersicon esculentum* that binds β-D-glucosamine oligomers (Sigma Aldrich Chemical, Catalog No. L-0651), and a negative control capture field having no capture agent bound thereto or a capture agent that is specific for another molecule that is not present in the sample.

Bar code results pictorially presented in FIG. 20 demonstrate that data output collected by means of standard microscopic analysis and data output collected using the CD imaging technology of the invention described herein are indistinguishable.

A direct benefit of this type of approach is that the analysis of blood samples from subjects can then be compared to a known barcode result in order to determine the blood-type of that subject immediately. In the example presented, more A-type red blood cells are bound in the A capture field than B-type red blood cells in the B capture field, indicating that the individual being tested has an A red blood cell phenotype.

Various embodiments of this method of the invention may be similarly designed for the purpose of blood typing according to any other blood typing system, e.g., for testing the Rh system blood group, the MNSs system blood group, the Lutheran system blood group, the Kell system blood group, the Lewis system blood group, the Duffy system blood group, the Kidd system blood group, the Fisher system blood group, or any other blood group. As will be understood by those in the art, one or more blood type systems may be simultaneously tested on a single bio-disc.

Antigentic Determinants

Various aspects of the present invention are drawn to methods for typing blood. The surfaces of red blood cells contain large numbers of antigenic determinants that are classified into blood groups. These antigenic determinants represent red blood cell surface markers that consist of protein and/or carbohydrate moieties. In humans there are at least 23 blood type groups (*The Blood Group Antigen Factsbook* (Factsbooks Series) by Marion E. Reid (Editor) and Christine Lomas-Francis (Editor) (January 1997) Academic Press; ISBN: 0125859651). The ABO blood grouping is perhaps the most important, serving as the basis for the determination of transfusion compatibility. Another frequently relied upon red blood cell grouping is the Rhesus (Rh) blood grouping, which is an important test during pregnancy.

A variety of other blood typing systems are amenable to the methods of the invention. The most important of these include, but are not limited to, the MNSs System, the Lutheran System, the Kell System, the Lewis System, the Duffy System, and the Kidd System, the Fisher group, or another blood group. For a detailed discussion of blood transfusion technologies and the basis for blood grouptyping, the following references are recommended: *Transfusion Medicine* by Jeffrey McCullough (December 1997), McGraw-Hill Professional Publishing; ISBN: 0070451133; *Modern Blood Banking and Transfusion Practices* by Denise Harmening (Editor) (March 1999), F. A. Davis Co; ISBN: 080360419X; *Immunohematology: Principles and Practice* by Eva D. Quinley (Editor) (January 1998), Lippincott Williams & Wilkins Publishers; ISBN: 0397554699; and *The Principles and Practice of Blood Grouping* by Addine G. Erskine, ASIN: 0801615305.

Most blood typing tests are based on hemagglutination and involve mixing a blood sample with a panel of typing reagents that react with various surface antigens and cause the cells to agglutinate. The presence or absence of agglutination is an indication of a specific blood type. The invention described herein utilizes a cell-capture technology uniquely adapted to a bio-disc format. The biological assays of the invention are designed to detect cell agglutination and/or cell binding. In certain embodiments of the invention, the subject for blood typing is a mammal, e.g., a mouse or a human. In another example, the subject is a non-human mammal or a non-human primate.

In certain embodiments of the invention, methods are provided for ABO and/or Rh typing of blood. The specific antibodies and antigens relevant for the ABO blood typing system are presented in Table 3.

Thus, individuals whose red blood cells carry the A antigen have antibody in their system directed against the B antigen, and individuals whose red blood cells carry the B antigen have antibody in their system directed against the A antigen. Individuals with both A and B antigens on their red blood cells produce no antibody directed against these antigens, and individuals with neither antigen present on their red blood cells have antibodies directed against both antigens in their system.

TABLE 3

The ABO Blood Type System

| Antigen | Antibody | Blood Group |
| --- | --- | --- |
| A | Anti-B | A |
| B | Anti-A | B |
| A and B | None | AB |
| None | anti-A, anti-B | O |

With the Rh blood typing system, there are three genes making up Rhesus antigens: C, D, and E, all found on chromosome 1. If an individual's Rh genotype contains at least one of the C, D, E antigens, they are Rhesus positive. Only individuals with the genotype cde/cde (rr) are Rhesus negative.

The remaining minor blood groups may complicate a blood typing but are not as important. In an individual, antibodies to the antigens not expressed on red blood cells are non-red-cell stimulated (or naturally occurring), due to the similarity between the blood group antigens structure and environmental agents. The antibodies may be of the IgM, IgA or IgG class. The IgM antibodies can cause direct agglutination when mixed with cells bearing the antigen to which the antibody is directed against. When an individual is exposed to red cells that are incompatible with his or her blood type, either through a transfusion or through pregnancy, the individual's immune system produces antibodies against the introduced foreign blood type; the antibodies produced by this process are predominately of the IgG class. The IgG antibodies can cross the placenta and cause hemolytic disease of the newborn in subsequent pregnancies.

As stated above, the ABO and Rh blood groups are the most important groups in transfusion medicine. Naturally occurring antibodies to the ABO and Rh antigens are of the IgM class. Antibodies to the ABO and Rh antigens are readily available and direct agglutination tests can be performed on red blood cell samples. In the system of the present invention, for forward typing assays, agglutination of the red cells is not the test; the test in this instance is cell capture based on antigen-antibody interactions. The interaction is specific and accurate and indicates which antigens are present on the red blood cell surface. For reverse typing of the ABO antibodies, agglutination of cells captured on the optical disc is looked for and analyzed by software algorithm(s).

In general, the invention described herein encompasses three types of blood cell typing. With respect to the ABO and Rh blood type systems, the assays include "forward" typing, in which antigens present on the surface of the red blood cells are detected by way of a cell capture assay, and "reverse" typing, in which antibodies directed to an ABO or Rh phenotype present in a patient's serum are detected by a cell agglutination assay. The third type of blood cell typing assay is referred to as "antibody" blood typing. It is a diagnostic assay designed to detect the presence of antibodies in a patient's serum directed to other, minor blood group phenotypes, e.g., Kell, Duffy, Kidd, etc. In addition, the Rh blood type of an individual can be determined with this type of assay. With antibody typing, the diagnostic test is based on cell capture and/or cell agglutination.

Forward Typing Assay

Figure 21E:
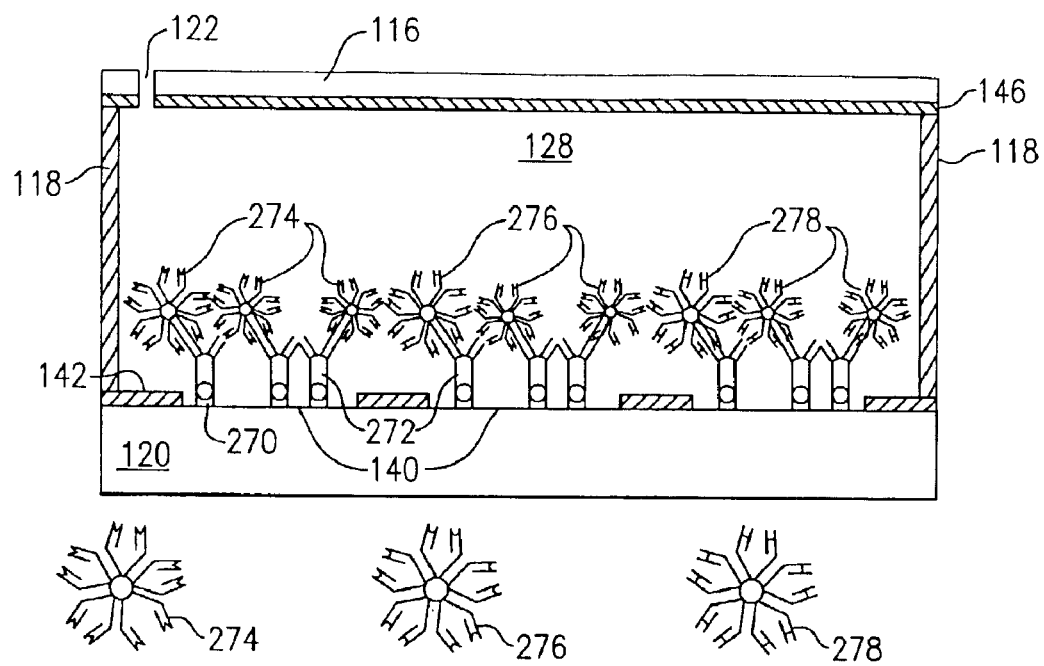
Figure 21F:
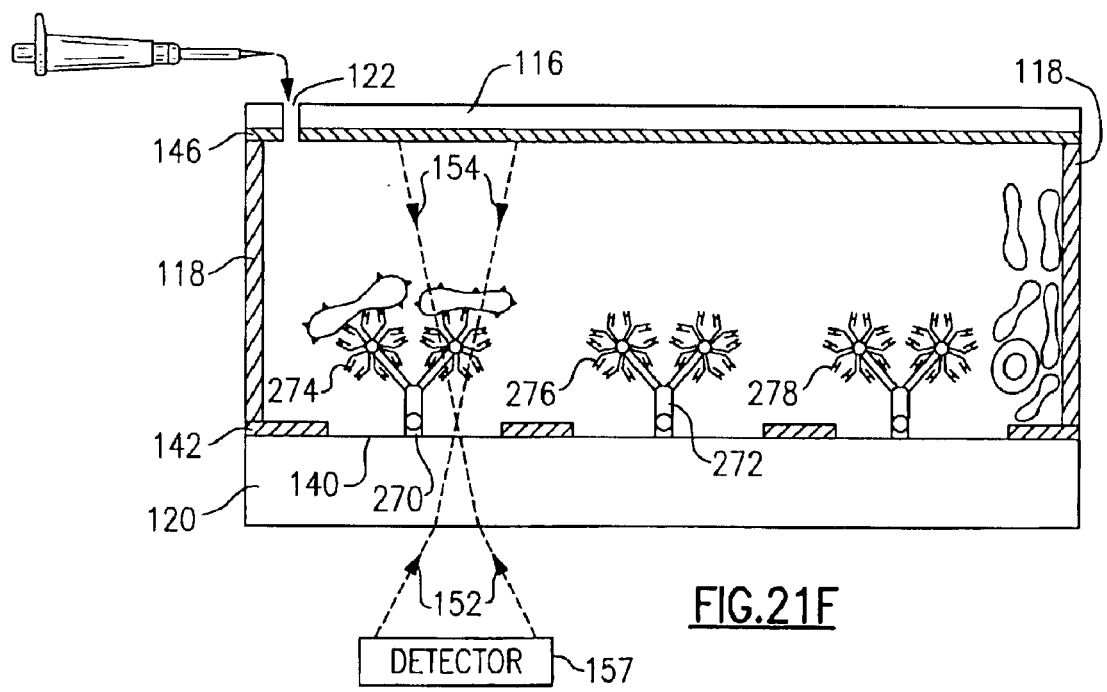

FIGS. 21A to 21F shows an example of a representation of the capture chemistry of one embodiment of the forward typing assay on a reflective zone disc. More specifically, FIG. 21A shows the substrate 120 coated with reflective layer 142 and capture zones 140 where the reflective layer has been removed. The reflective layer may be removed by lithography, for example. FIG. 21B shows a layer of streptavidin 270 passively adsorbed to the capture zones 140. FIG. 21C shows biotinylated first capture antibody 272 bound to the steptavidin 270 in the capture zone 140. FIG. 21D shows the second capture antibodies 274, 276 and 278 with different specificities bound to the biotinylated first capture antibody 272. FIG. 21E shows an assembled bio-disc with cap portion 116, reflective surface 146 and inlet port 122, adhesive member 118, channel 128 and the following capture chemistries: streptavidin 270, a first capture antibody 272, and three different second capture antibodies 274, 276 and 278 in the capture zone 140 on the substrate 120. FIG. 21F shows specific cell capture by capture antibody 274 based on antigens expressed on the surface of a cell. Capture antibodies 276 and 278 have no specificity of binding for cells being tested in the experiment presented. FIG. 21F also demonstrates the method of detection by focusing an incident beam of electromagnetic radiation 152 passing through a capture zone 140 to strike a reflective layer, thereby producing a return beam of electromagnetic radiation 154 which is delivered to a detector system 157.

As used herein, the term "chamber" encompasses any three-dimensional space defined by at least one material that is affixed to or part of an optical bio-disc. In one embodiment, the chamber is leak-proof so that a liquid sample may be loaded into the chamber and subjected to certain reaction conditions (such as antibody binding conditions) and to detection methods (such as beam interrogations). The chamber may be made of plastic, of metal, of glass or of any other material that is suitable for the biological assay for which the optical bio-disc is used. In one non-limiting example, the chamber may hold from about 4 µl to about 50 µl. In another example, the chamber is in fluid communication with a second chamber that can be utilized as a waste repository following the biological assay.

As used herein, an antibody that "specifically binds" means an antibody that binds to an epitope, which comprises a peptide sequence, or a carbohydrate moiety, or a lipid moiety, or a specific sequence of oligonucleotides, or a combination thereof. Such an antibody will not promiscuously bind to other molecules that do not have that specific epitope. Such a specifically binding antibody will not bind (or cross react) with other molecules or compounds lacking such an epitope.

The assay is performed within an optical bio-disc that includes a chamber (also, "flow chamber") having specific antibodies or other capture molecules attached to the solid phase associated with that chamber. In one non-limiting example of the invention, a method is described for the determination of the occurrence of a specific cell type (e.g., a specific type of red blood cell) expressing cell-specific surface antigens (e.g., A or B antigens) captured by specific antibodies affixed to the capture field(s).

An optical bio-disc drive assembly is employed to rotate the disc, read and process any encoded information stored on the disc, and analyze the cell capture fields in the flow chamber of the bio-disc. The bio-disc drive is provided with a motor for rotating the bio-disc, a controller for controlling the rate of rotation of the disc, a processor for processing return signals from the disc, and analyzer for analyzing the processed signals. The rotation rate is variable and may be closely controlled both as to speed and time of rotation. The bio-disc may also be utilized to write information to the bio-disc either before, during or after the assay. The test material in the flow chamber and capture fields is interrogated by the read beam of the drive and analyzed by the analyzer. The bio-disc may include encoded information for controlling the rotation of the disc, providing processing information specific to the type of immunotyping assay to be conducted and for displaying the results on a monitor associated with the bio-drive.

The methods encompass evaluation tests in CD, CD-R, DVD, or any equivalent optical disc format. Variations or alternative versions thereof according to the present invention include a robust capture chemistry that is stabilized on the optical bio-disc. Unbound non-specific cells are spun off leaving behind specific target cells from the blood sample that are specifically bound to the capture field on the bio-disc. The read or interrogation beam of the drive detects the captured cells and generates images that can be analyzed.

Reverse Typing Assay

Figure 27:
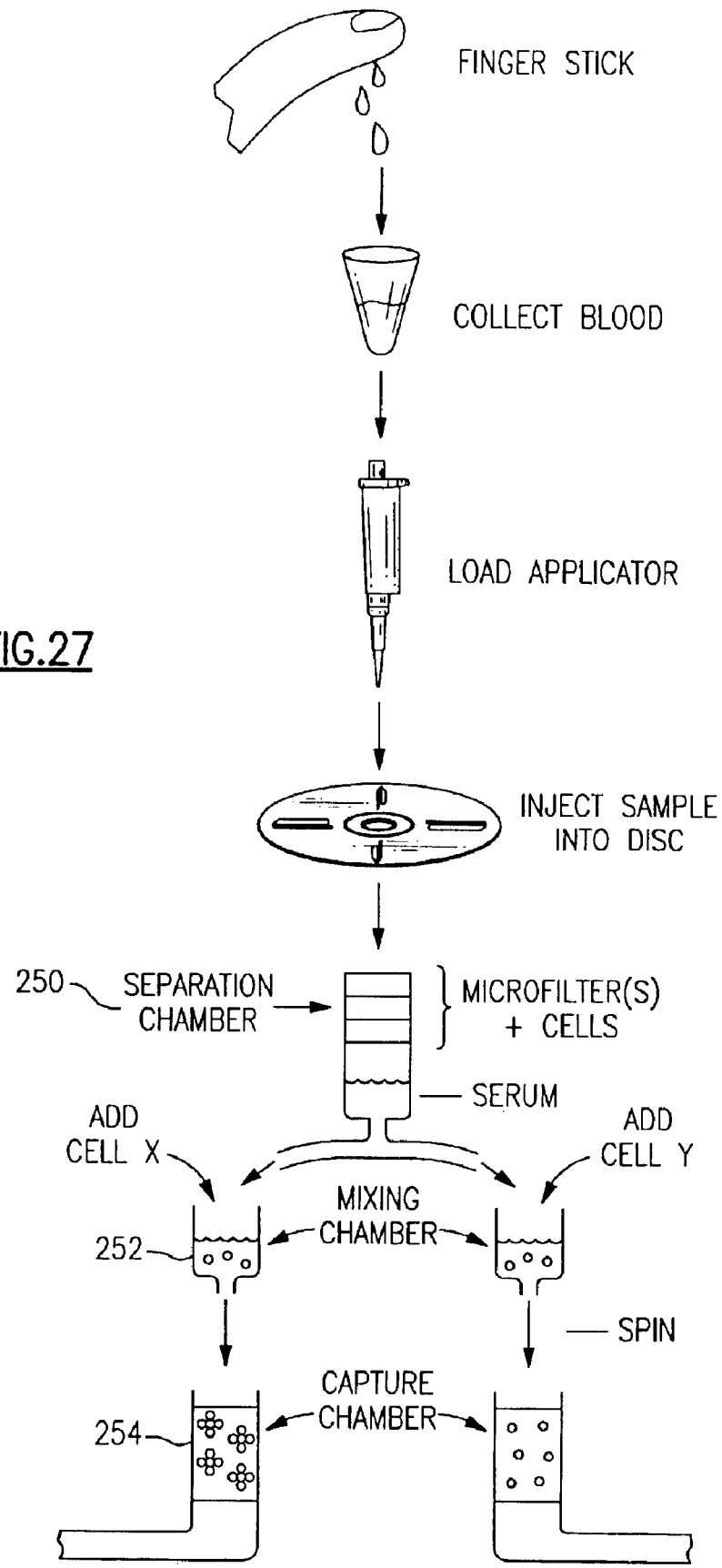
FIG. 27 is a pictorial flow diagram presenting the method of reverse ABO/Rh typing wherein sample preparation and processing are all done on the optical bio-disc.

The invention also provides a method for detecting specific antibodies to an ABO/Rh blood group antigen, e.g., assaying a patient's serum for the occurrence of anti-A or anti-B antibodies. In one embodiment, the invention provides a method for reverse typing wherein the sample undergoes processing prior to being loaded onto a bio-disc (FIGS. 22, 23, 24A, 24B, 24C, 25A, 25B, 25C, 26A, 26B, and 26C). In another embodiment, the invention provides a method for reverse typing wherein the sample is loaded onto a bio-disc without significant processing (FIG. 27).

Figure 22:
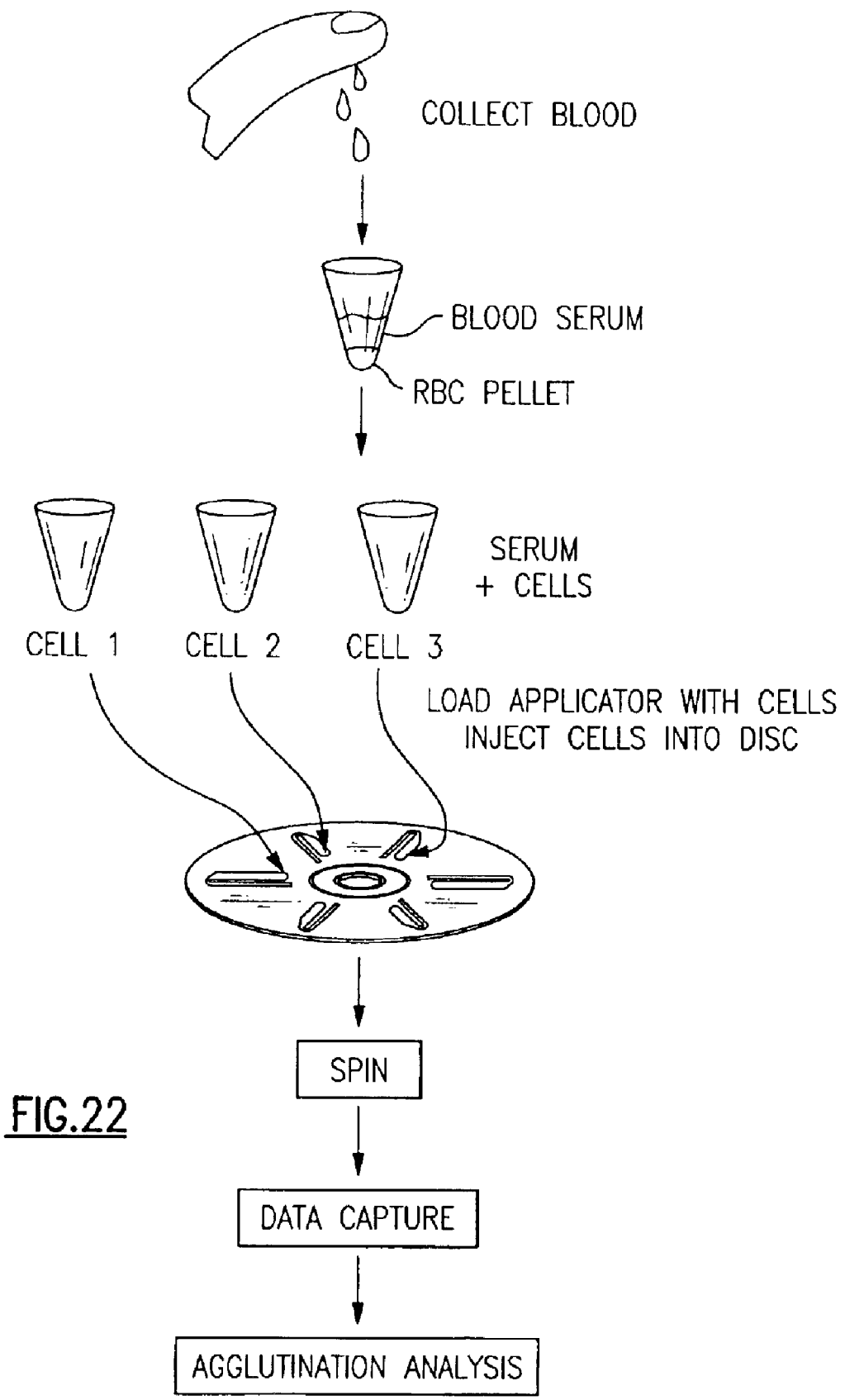
FIG. 22 is a pictorial flow diagram illustrating different methods of reverse typing for the ABO/Rh blood groups with sample preparation off-disc and sample analysis on disc.

Referring to FIG. 22, in the first embodiment of reverse typing, whole blood is first collected, e.g., by finger stick, and cells are separated from serum prior to utilizing the serum in the bio-disc blood grouping assay. Whole blood can be separated into serum and cells by light centrifugation, for example. The serum, which contains a patient's antibodies, is then mixed with one or more cell types having an ABO cell phenotype. For example, cell 1 of FIG. 22 can be an A type cell, cell 2 of FIG. 22 can be a B type cell, and cell 3 of FIG. 22 can be an AB type cell. The sample is then incubated for a period of time, e.g., about one to five minutes, at room temperature to allow the patient's antibodies to interact with these cells. After incubation, if an anti-human antibody is used as the capture agent, the cells are washed several times and loaded into one or more chambers in the bio-disc; if a lectin capture agent is used, washing is unnecessary.

If antibodies of the appropriate specificity are found in the patient's serum, the red blood cells will be agglutinated as a result of the antibodies bound thereto. These agglutinated cells can then be captured on a capture field by an appropriate capture agent, e.g., a lectin that binds all cells. After a brief spin of the disc, e.g., 400 rpm to 4000 rpm, to remove unbound cells, the capture field is examined for the occurrence of agglutinated cells. The capture field can then be examined by the optical reader to determine whether cells being tested are agglutinated, and thereby determine that antibodies to an ABO/Rh blood group antigen were present in the individual's blood.

Figure 23:
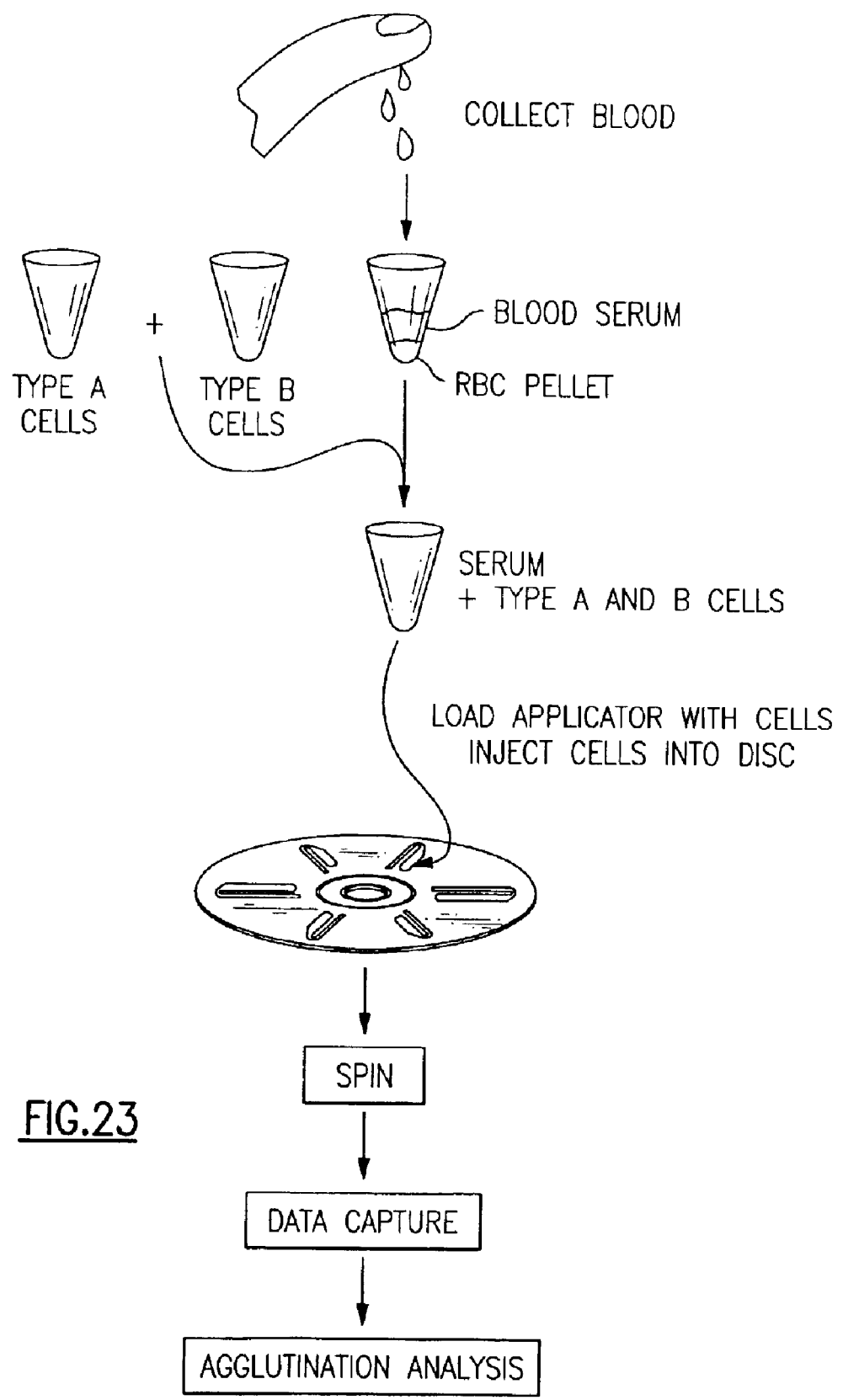
FIG. 23 is another pictorial flow diagram illustrating different methods of reverse typing for the ABO/Rh blood groups with sample preparation off-disc and sample analysis on disc.

In FIG. 23 there is shown a second embodiment of reverse typing, whole blood is first collected, e.g., by finger stick, and cells separated from serum prior to utilizing the serum in the bio-disc blood grouping assay. Whole blood can be separated into serum and cells by light centrifugation, for example. The Reagent Type A and Type B cells are mixed. Then the serum, which contains a patient's antibodies, is added to the cell mixture to thereby create a sample mixture. The sample mixture is then incubated for a period of time, e.g., about one to five minutes, at room temperature to allow the patient's antibodies to interact with these cells. After incubation the assay mixture is loaded into one chamber which has at least one anti-A capture zone and one anti-B capture zone. The capture of the agglutinated and non-agglutinated cells is illustrated and described below in conjunction with FIGS. 26A, 26B, and 26C.

If antibodies of the appropriate specificity are found in the patient's serum, the red blood cells will be agglutinated as a result of the antibodies bound thereto. If anti-A antibodies are present in the serum sample, for example, then agglutination of the Type A cells occurs. The agglutinated cells or un-reacted single cells are then captured on the specific capture zones. After a brief spin of the disc, e.g., 400 rpm to 4000 rpm, to remove unbound cells, the capture zones are examined for the presence of agglutinated cells and single cells. The capture zones can then be examined by the optical reader to determine whether cells being tested are agglutinated or single, and thereby determine that antibodies to an ABO/Rh blood group antigen were present in the individual's blood.

Figures 24A, 24B, 24C:
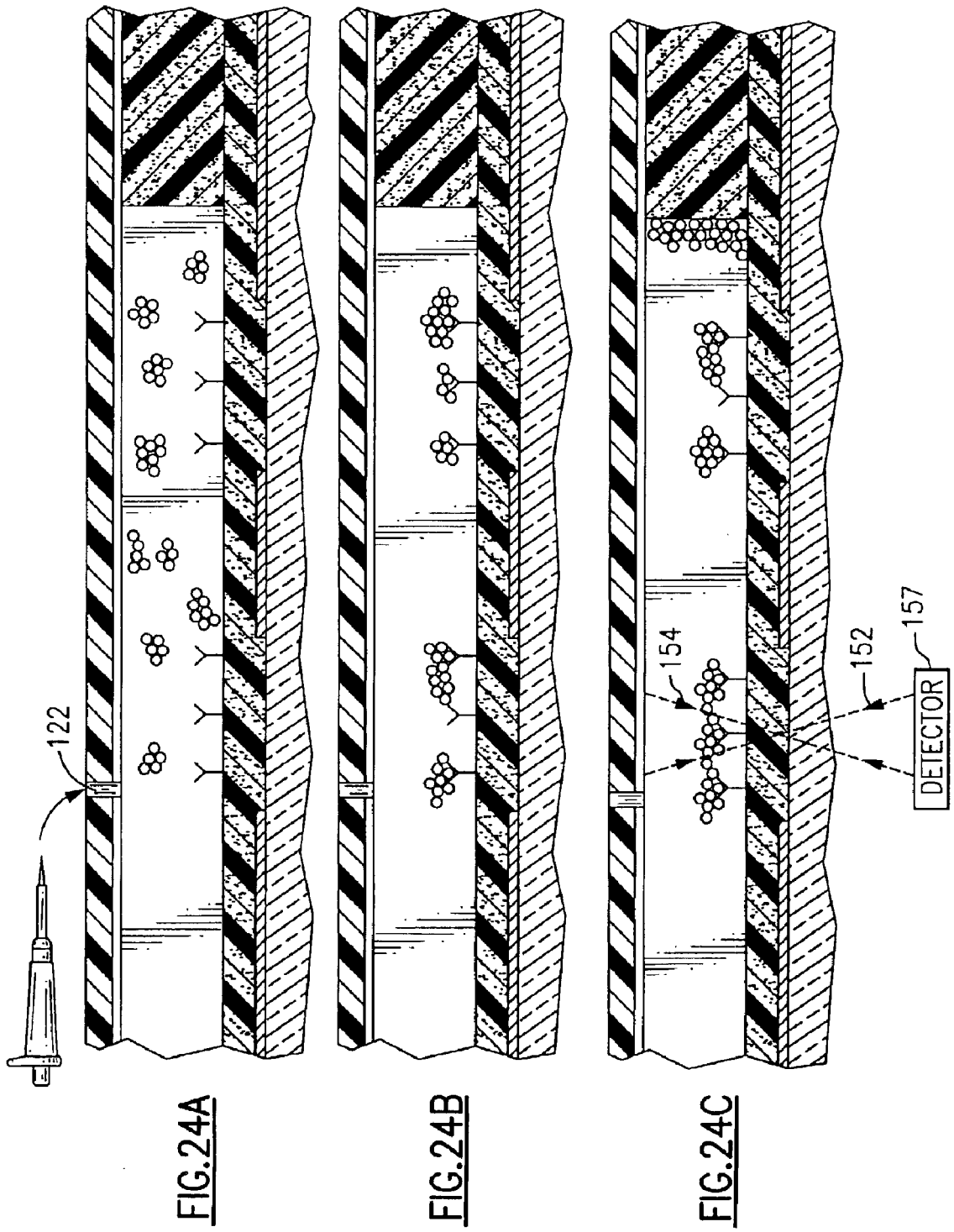
FIGS. 24A–24C are cross-sectional side views of an optical bio-disc showing the cell binding during the reverse typing test when antibodies to an ABO/Rh blood group antigen are present.

Referring now to FIG. 24A, there are shown test cells or typed reagent cells, previously mixed with a patients serum, agglutinated by the patient's antibody, loaded into the inlet port 122 of an optical bio-disc having specific capture fields. As can be seen in the figure, at this stage, cells are agglutinated but not bound to a capture agent of the capture field. In FIG. 24B, after a pre-determined incubation period, the agglutinated test cells are specifically recognized and captured by the capture agent immobilized on the capture field. After a sufficient time for capture to occur (incubation time), the optical bio-disc is spun and all cells not bound by the capture agent are removed from the capture field (FIG. 24C). Once unbound cells are removed, data detection is accomplished by focusing an incident beam of electromagnetic radiation 152 through the capture field to strike a reflective layer, thereby producing a return beam of electromagnetic radiation 154 that is delivered to a detector system 157. Analysis of the data provides information relating to whether the cells that bound to the capture agent were agglutinated or not agglutinated.

In contrast, test cells that are not reactive with a patient's serum will not be agglutinated. FIG. 25A depicts test cells not agglutinated by a patient's serum loaded into an inlet port 122 of an optical bio-disc having a capture field. After a sufficient period of incubation, these cells are captured by the capture agent bound to the capture field (FIG. 25B). Once unbound cells are removed by centrifugation (FIG. 25C), data collection and analysis are done as described for FIG. 24C. The analysis software of the invention can discriminate between single cells and agglutinated cells bound to the capture field.

Referring next to FIG. 26A, there is illustrated an assay solution containing agglutinated and single cells being added to the chamber. The assay solution may be prepared as described above in FIG. 23. After a sufficient period of incubation, the agglutinated and non-agglutinated reagent cells are captured by their respective capture agents bound to the capture zone, as depicted in FIG. 26B. Furthermore, FIG. 26B shows a capture zone with agglutinated cells and a separate capture zone with single cells. Once unbound cells are removed as shown in FIG. 26C, data collection and analysis are done as described for FIG. 24C. The analysis software of the invention can discriminate between single cells and agglutinated cells bound to the capture field.

In the third embodiment of reverse typing, whole blood, or a diluted sample thereof, is loaded directly onto the bio-disc into a microfluidic circuit, microfluidic channel, or flow channel as illustrated in FIG. 27. The present method provides for the separation of blood cells and serum by passage through a separation chamber 250 in the optical bio-disc. Separation of the fluid and cellular components of whole blood is effected by spinning the disc at a first speed, moving the sample through at least one microfilter designed to separate red blood cells, white blood cells and platelets from the serum. Serum is then moved to at least one mixing chamber 252 by spinning the disc at a second speed, which is higher than the first speed. Cells of a specific ABO group phenotype are then added through a separate entry port 256 into at least one mixing chamber 252. Mixing of the serum and cells is accomplished by spinning the disc at least once, one-half a rotation counter clockwise and then clockwise one-half a rotation. The samples are then allowed to incubate in the mixing chamber 252 for a sufficient time to allow antibody-antigen interaction. The cells are then moved to a capture chamber or analysis chamber 254 with a capture field by spinning the disc at a third speed, which is higher than the second speed. The cells are allowed to interact with the capture field which has bound to it anti-human immunoglobulin or another capture agent for a sufficient time to allow capture agent interaction with the cells. The disc is then spun again to remove unbound cells, e.g., 400 rpm to 4000 rpm. Data is then collected from the capture fields to determine if cells bound thereto are agglutinated. The occurrence of agglutinated cells in a capture field indicates that the individual's serum has antibodies directed to an antigen on the surface of the particular red blood cell blood type phenotype being tested. Alternatively, the capture chamber 254 may be packed with a bio-matrix that separates the agglutinated cells from the non-agglutinated cells. Details regarding this aspect of the invention are discussed below in conjunction with FIGS. 35, 36A, 36B, 37A, 37B, and 37C.

Direct Typing Assay

Figures 30A, 30B, 30C:
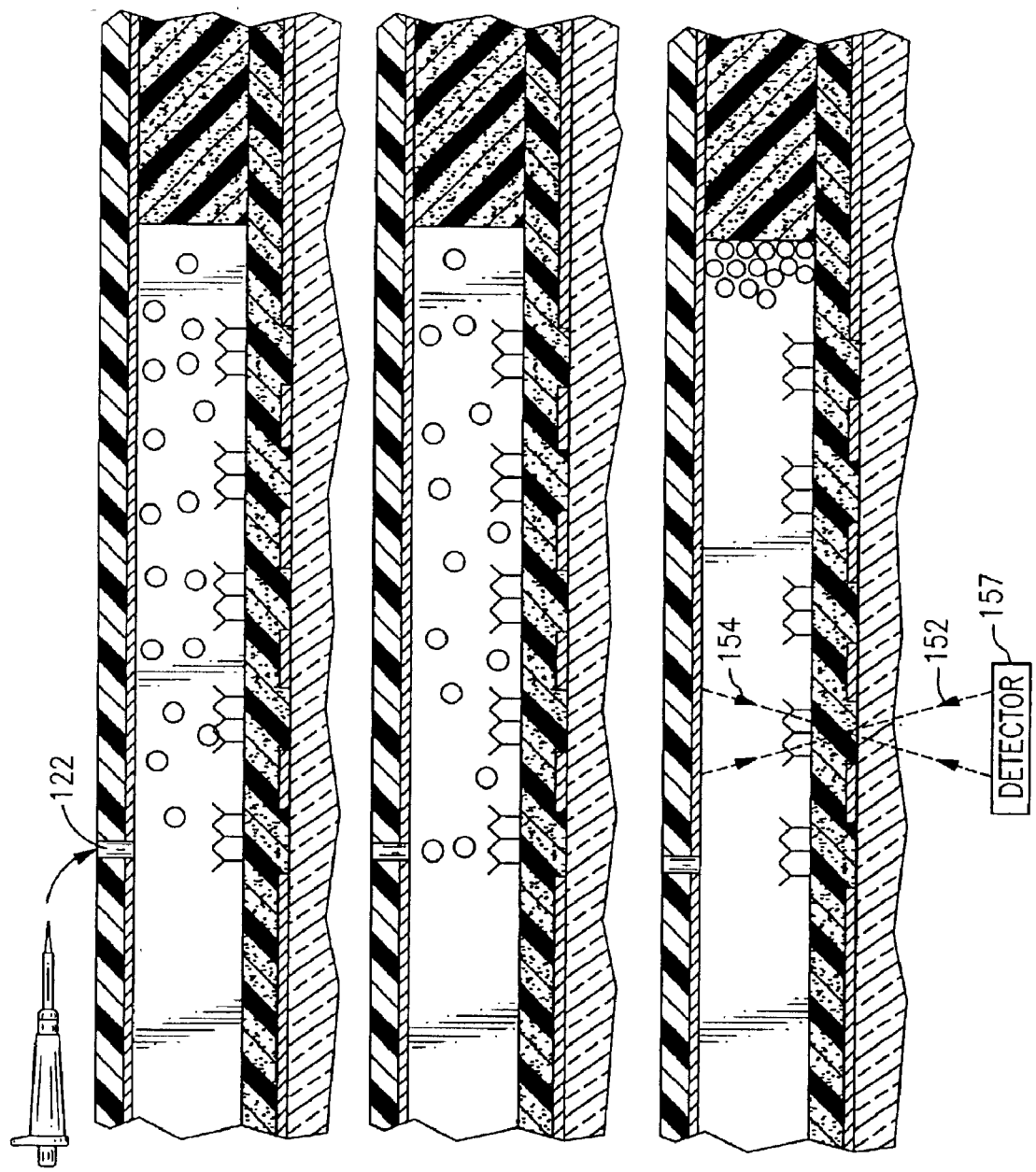
FIGS. 30A–30C are cross-sectional side views of an optical bio-disc including red blood cells not bound by antibodies coming into contact with, and not being captured by the capture field.
Figure 31:
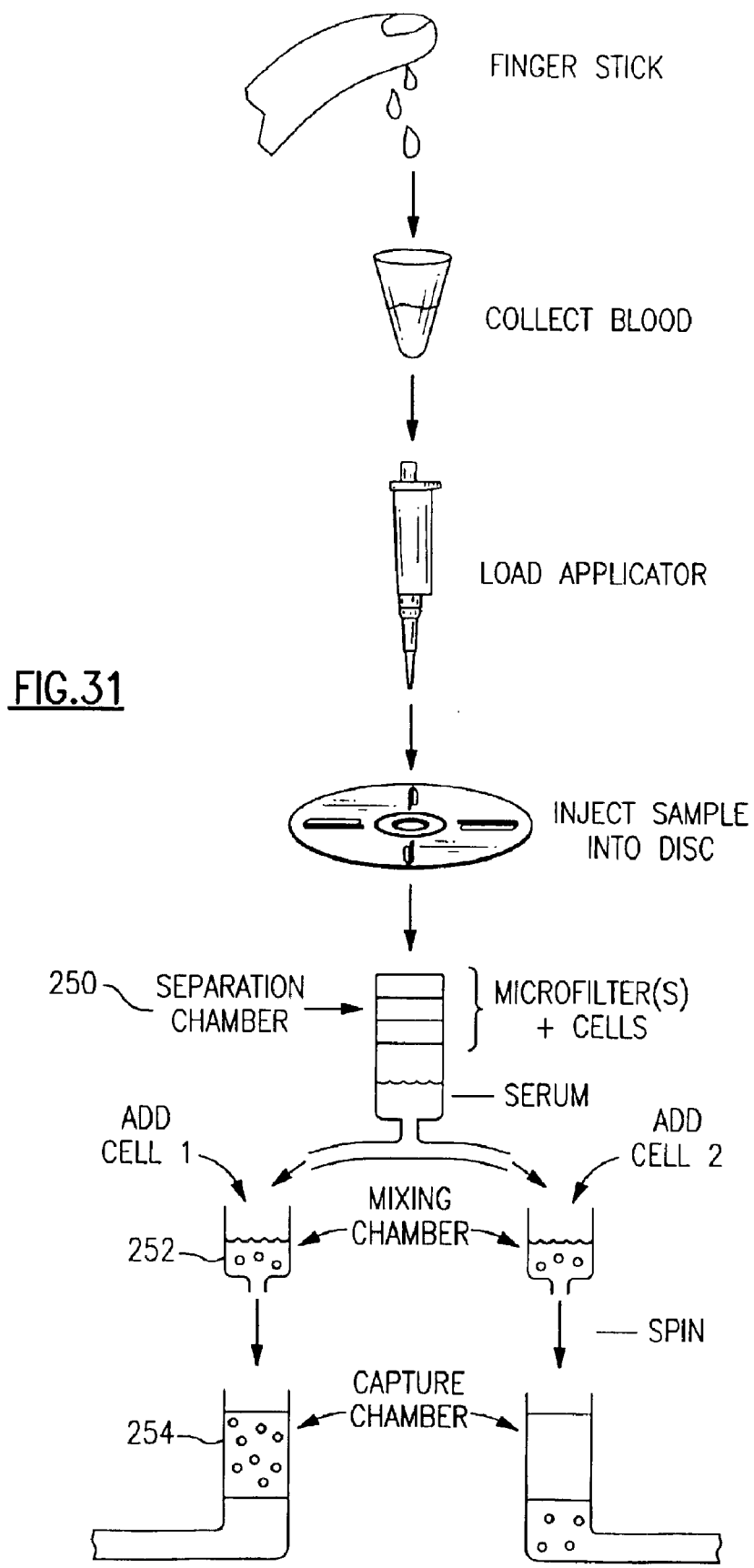
FIG. 31 is a pictorial flow diagram presenting the method of antibody typing wherein sample preparation and processing are all done on the optical bio-disc.

In another aspect, the invention provides methods for antibody typing (or direct typing) a blood sample, i.e., testing a patient's serum for the occurrence of antibodies directed to an antigen of a blood group other than that of the ABO system. In one embodiment of this aspect, the invention provides a method for antibody typing wherein the sample undergoes processing prior to being loaded onto a bio-disc (FIGS. 28, 29A, 29B, 29C, 30A, 30B, and 30C). In another embodiment of this aspect, the invention provides a method for antibody typing wherein the sample is loaded onto a bio-disc without significant processing (FIG. 31). Cells of a known blood group phenotype other than that of the ABO system, e.g., Kell, Duffy Kidd, etc., are available commercially for testing purposes (Immucor, Inc. Norcross, Ga., PANOSCREEN).

Figure 28:
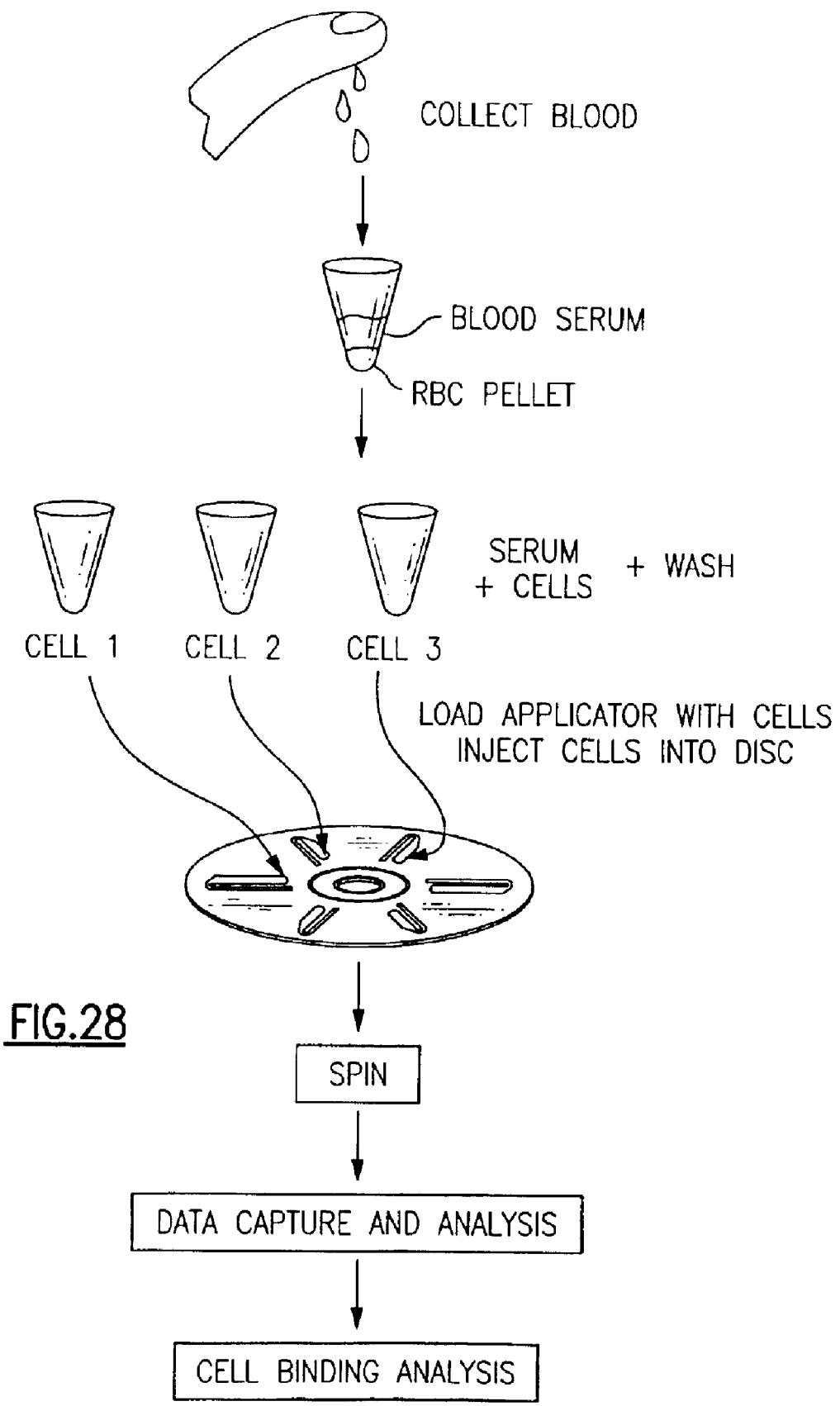
FIG. 28 is a pictorial flow diagram demonstrating the method of antibody typing for blood groups other than the ABO/Rh types with sample preparation off-disc and sample analysis on disc.

Referring to FIG. 28, in yet another embodiment of antibody typing, whole blood is first separated from serum prior to utilizing the serum in the bio-disc blood grouping assay. Whole blood can be separated into serum and cells by light centrifugation. The serum, which contains a patient's antibodies, is then mixed with one or more O type ABO test cells having a known phenotype for a blood group type other than that of ABO. The sample is incubated for a period of time, e.g., about fifteen to thirty minutes, at 37° C. to allow the patients antibodies to interact with these cells. After incubation, the cells are washed several times and loaded into one or more chambers in the bio-disc. If antibodies of the appropriate specificity are found in the patient's serum, the red blood cells will have the antibodies bound thereto. These antibody-bound cells can then be captured on a capture field by an appropriate capture agent, e.g., an anti-human IgG. After a brief spin of the disc (e.g., 400 rpm to 4000 rpm) to remove unbound cells, the capture field is examined for the occurrence of cells. The capture field can then be examined by the optical reader to determine whether cells being tested are present in the capture field, and thereby determine the antibody status of the individual.

Figures 29A, 29B, 29C:
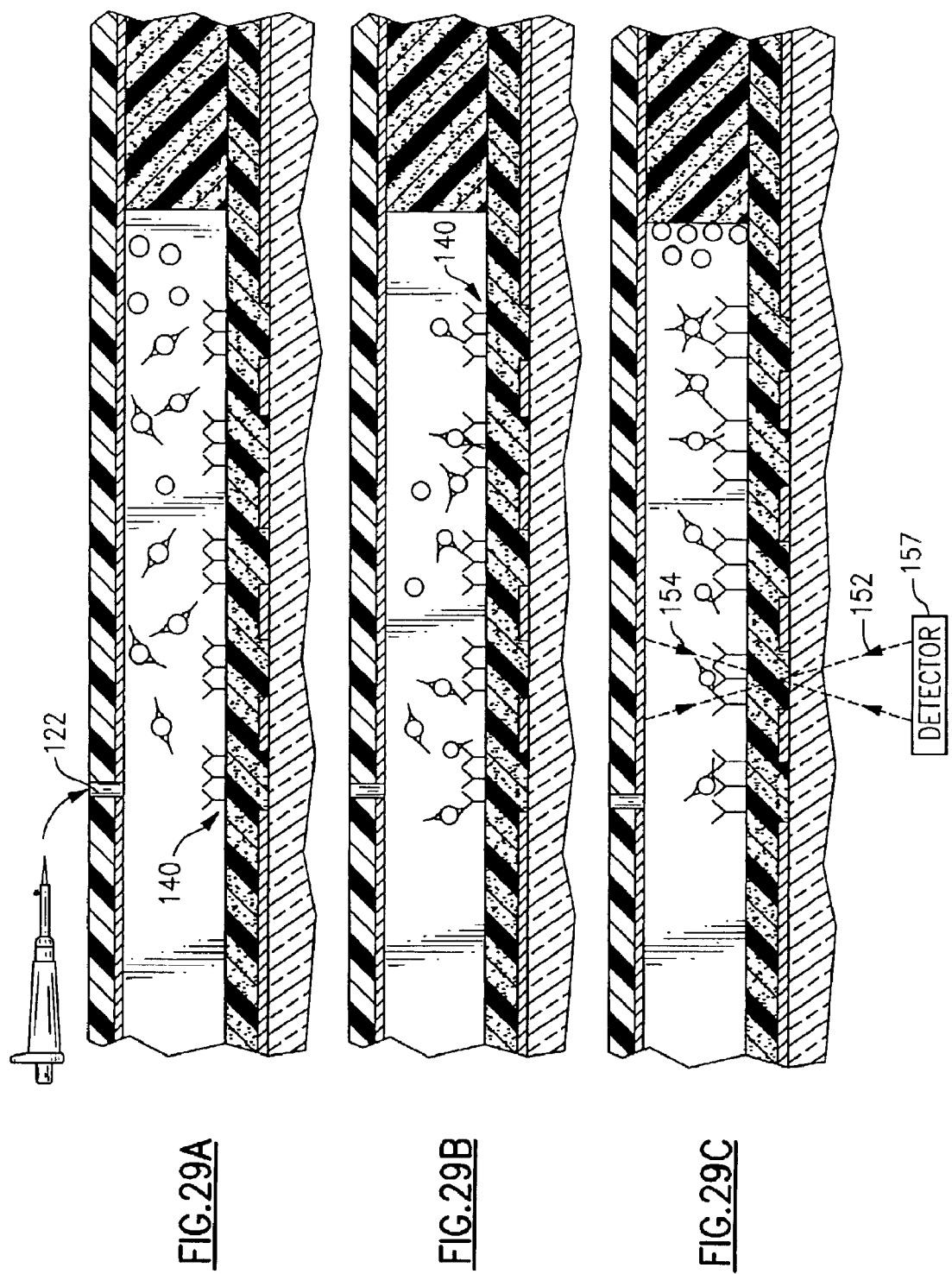
FIGS. 29A–29C are cross-sectional side views of an optical bio-disc including red blood cells bound by antibodies coming into contact with, and being captured by the capture field.

The molecular recognition events occurring during the assay are depicted in FIGS. 29 and 30. In FIG. 29A, test cells previously mixed with a patients serum and bound by antibodies contained therein are loaded into the inlet port 122 of an optical bio-disc having a capture field. In FIG. 29B, after the indicated incubation period, test cells bound by a patient's antibody are specifically recognized and captured by the anti-immunoglobulin antibody (i.e., capture agent) immobilized on the capture field 140. Following a sufficient capture time, the optical bio-disc is spun and all cells not captured by the capture agent are removed from the capture field (FIG. 29C). Once unbound cells are removed, data detection is accomplished by focusing an incident beam of electromagnetic radiation 152 through the capture field to strike a reflective layer, thereby producing a return beam of electromagnetic radiation 154, which is delivered to a detector system 157.

In contrast, test cells that are not reactive with a patient's serum will not be bound to a capture field. FIG. 30A depicts the loading of test cells not bound by antibodies of a patient's serum into inlet port 122 of an optical bio-disc. Even after a sufficient period of incubation, these cells are not captured by the capture agents bound to the capture field (FIG. 30B). The cells are removed from the capture field after a brief, low speed spin (FIG. 30C) and data detection is accomplished as above.

Another embodiment of the antibody typing method of the invention involves the use of an optical bio-disc having at least one microfluidic circuit. FIG. 31 is a pictorial flow diagram illustrating the steps involved in this method. As described in FIG. 28, blood is collected and appropriately diluted in preparation for the assay. The test sample is loaded into an applicator for loading into the inlet port of an optical bio-disc. Initially, the sample containing cells and serum enters a separation chamber 250 having microfilters which separate the cells from the serum. The serum is then moved into a mixing chamber by centrifugation and type reagent test cells are added thereto. After a sufficient period of time, the sample is then moved into a capture chamber and analysis subsequently occurs.

Figure 32:
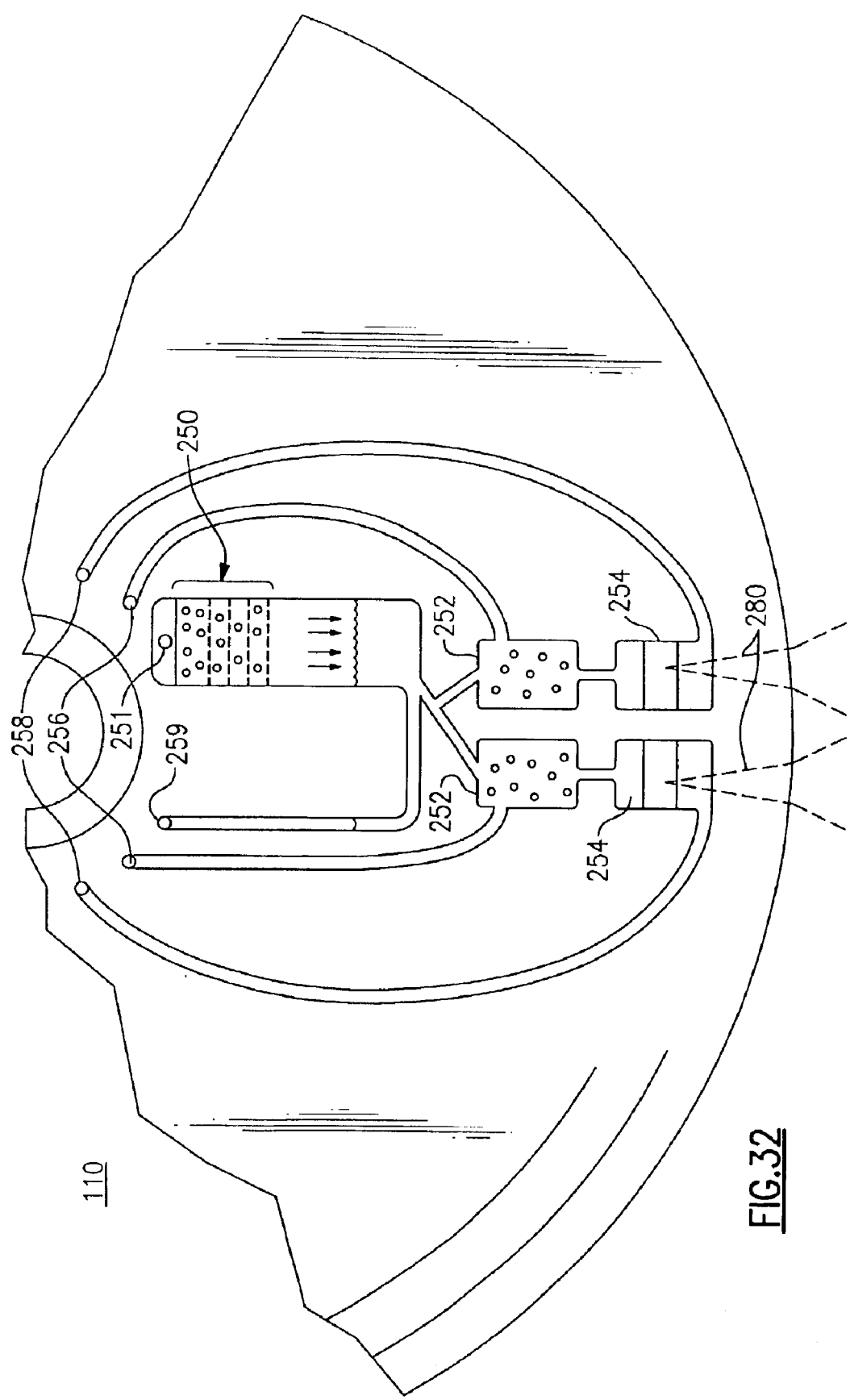
FIG. 32 is an enlarged plan view representing one example of a microfluidic channel containing inlet ports, a separation chamber, mixing chambers, capture or analysis chambers, and vent ports.

FIG. 32 presents embodiments of the microfluidic circuit described above, in more detail. The sample is first loaded into an inlet port 251 and enters a separation chamber 250 in the optical bio-disc. Spinning the disc at a first speed, thereby moving the sample through at least one microfilter designed to separate red blood cells, white blood cells, and platelets from the serum, effectively separating the fluidic and cellular components of whole blood. Serum is then moved to at least one mixing chamber 252 by spinning the disc at a second speed, which is higher than the first speed. Reagent cells of a known blood group phenotype are then added through a separate entry port 256 into at least one mixing chamber 252 of the bio-disc.

With various aspects and embodiments of the invention, the microfluidic circuit has one or more inlet ports 256 for the addition of cells of a known blood group phenotype (typed reagent cells) to the mixing chamber(s). In other various aspects and embodiments of the invention, the microfluidic circuit has a single mixing chamber feeding a single capture chamber 254. In yet other various aspects and embodiments of the invention, the inlet port(s) 256 are not necessary, since the mixing chamber has been preloaded with a microparticle coated with a specific antigen of a red blood cell blood type group, e.g., M antigen or N antigen. Such antigens may be conveniently prepared by purifying the red blood cell antigen, e.g., through recombinant gene expression, subsequent biochemical isolation, and absorbing it onto the particles. These particles may then be loaded into the mixing chamber during construction of the bio-disc, e.g., in freeze-dried form. A bio-disc of this construction would be particularly useful in countries and areas where access to red blood cells of a known blood type phenotype is difficult.

Mixing of the serum and cells is accomplished by spinning the disc at least once one-half of a rotation counter clockwise and then clockwise one-half of a rotation. The samples are then allowed to incubate in the mixing chamber 252 for a sufficient time (e.g., 15 to 30 minutes) to allow antibody-antigen interaction. The cells are then moved to a capture chamber 254 with a capture field by spinning the disc at a third speed, which is higher than the second speed. The cells are allowed to interact with the capture field, which has bound to it anti-human IgG, for a sufficient time (e.g., 30 seconds to 15 minutes) to allow antibody-antigen interaction. The disc is then spun (e.g., 400 rpm–4000 rpm) to remove unbound cells. Data is then collected from the capture fields to determine if cells are bound to the capture field. The occurrence of cells in a capture field indicates that the individual's serum has antibodies directed to an antigen on the surface of the particular red blood cell being tested. An alternative embodiment of the above discussed antibody typing using bio-matrix cell or particle separation is described below in conjunction with FIGS. 35, 36A, 36B, 37A, 37B, and 37C.

Software and Related Processing Methods

Computer-based analysis is performed in a determination of blood type. Results of executing a procedure involving an optical bio-disc are analyzed by software to determine a blood type and/or antibody types of a blood sample supplied on the bio-disc.

In one or more specific implementations, the procedure involving the bio-disc may be executed under software control. For example, software may prompt a user to prepare the bio-disc (e.g., by loading a blood sample into the bio-disc and inserting the bio-disc into a reader), and may subject the bio-disc to one or more spin sessions at one or more rotation speeds. In a specific implementation, the procedure may include washing and/or incubation.

In one or more implementations, the software may cause execution of the procedure to be responsive to input from the user or to intermediate results of executing the procedure, or to both. For example, the software may pause execution pending a signal (e.g., by keyboard or mouse) reporting that the user has added material to the bio-disc. In another example, the software may determine that a condition (e.g., the presence or absence of material in a particular location) on the bio-disc has been detected, and may cause the procedure to execute in a particular way based on the detection. In a specific implementation, the software may determine a confidence level (e.g., based on a margin of error) of a determination as to blood type, and based on the confidence level the software may cause the bio-disc to be spun at a rate and a duration that delivers all or a portion of a blood sample to a microfluidic circuit or assay zone for another blood type determination.

In one or more implementations, the bio-disc may have write-compatible properties (e.g., write properties of a CD-R or CD-RW) and the software may cause information (e.g., representing or derived from intermediate or final results of the procedure) to be written to the bio-disc and thereby made available for subsequent retrieval by the software or another program. The retrieval, which may occur one or more times, may occur during the same instance of execution of the procedure, and may thereby affect the execution of the remainder of the current instance, or may occur after or at the end of the current instance. For example, once the software has determined the blood type of the sample, information including an identification of the blood type and optionally underlying data as well may be recorded on the bio-disc. In such a case, in at least some circumstances, the bio-disc can be archived (e.g., for evidentiary or confirmation purposes in legal proceedings) so that the software's determination is available in a fixed form physically associated with the actual sample from which the blood type determination was made. The bio-disc can thus serve as an enhanced medical record of blood-typing, and can be retrieved later for additional analysis (e.g., DNA testing or direct year-to-year comparisons or cumulative or historical analysis under software control).

Accordingly, interactivity may be provided in one or more of at least two forms: interaction with the user and interaction with the bio-disc. Interaction between the software and the user may take the form of output to the user (e.g., on an electronic display, via voice or other audio, or via another mechanism that is detectable by a human sense such as smell or touch) and input from the user (e.g., via keyboard, mouse, joystick, microphone, light sensor, or another mechanism that allows a computer to detect a physical change).

In one or more specific implementations, the results of the procedure may be communicated in the form of one or more electronic signals that may be produced with the use of one or both of a moving laser head and a moving light detector applied to an optical bio-disc having one or more tracks, which achieves track by track generation of signal information. For example, analog signals representing reflected or transmitted light readings from an optical bio-disc may be received and may be converted to digital signals that are analyzed in the blood or antibody type determination. As described in more detail below, the software may analyze the electronic signals to identify, locate, and/or quantify transitions in light intensity that represent the boundaries of material (e.g., producing dark spots) resulting from execution of the procedure, and may draw a conclusion as to blood or antibody type based on the existence/absence, location, and/or quantity of the material.

The software and procedure may include or rely on an ABO technique or ABO cell counting technique, or an antibody typing process that may include wash and/or preparation steps in microfluidic circuits and the moving of material to a testing area and/or a waste area for detection, e.g., by a light intensity and/or optical density technique.

With reference again to FIG. 32, there is illustrated an example of a microfluidic circuit that may be used with the software and/or the procedure. The software may control the timing of the use of areas 250, 252, 254, may cause information such as intermediate results to be recorded on the circuit's bio-disc, and may cause execution of the procedure to be affected by results or conditions found pertaining to one or more of the areas 250, 252, 254. For example, the software may cause the bio-disc to have a behavior A if a condition X is found in area 250, and may cause the bio-disc to have a behavior B if a condition Y is found in area 250. Similar tests and actions may be executed with respect to other areas of the bio-disc in addition or instead. The software can implement a branching process or a flowchart that is responsive to intermediate results or conditions found. Accordingly, different variations of a blood typing test, or different blood typing tests, can be implemented using the same bio-disc arrangement with correspondingly different variations or configurations of software. Depending on the test variation or test that is in effect, the software can cause the bio-disc to spin faster or slower at different times and with breaks of different durations, and can direct the drive's laser to expose different areas to different amounts of light, to create the procedural environment that suits the test variation or test.

In general, the software can implement interactive, multi-route processing with the bio-disc. For example, a microfluidic circuit may have 5–6 stages and the software may take certain action depending on a result in the first stage, and then may take other action depending on a result in the second stage, and may continue similarly in the remaining stages. The functionality of the bio-disc and other hardware is thus directed by the software and the results.

Figure 34:
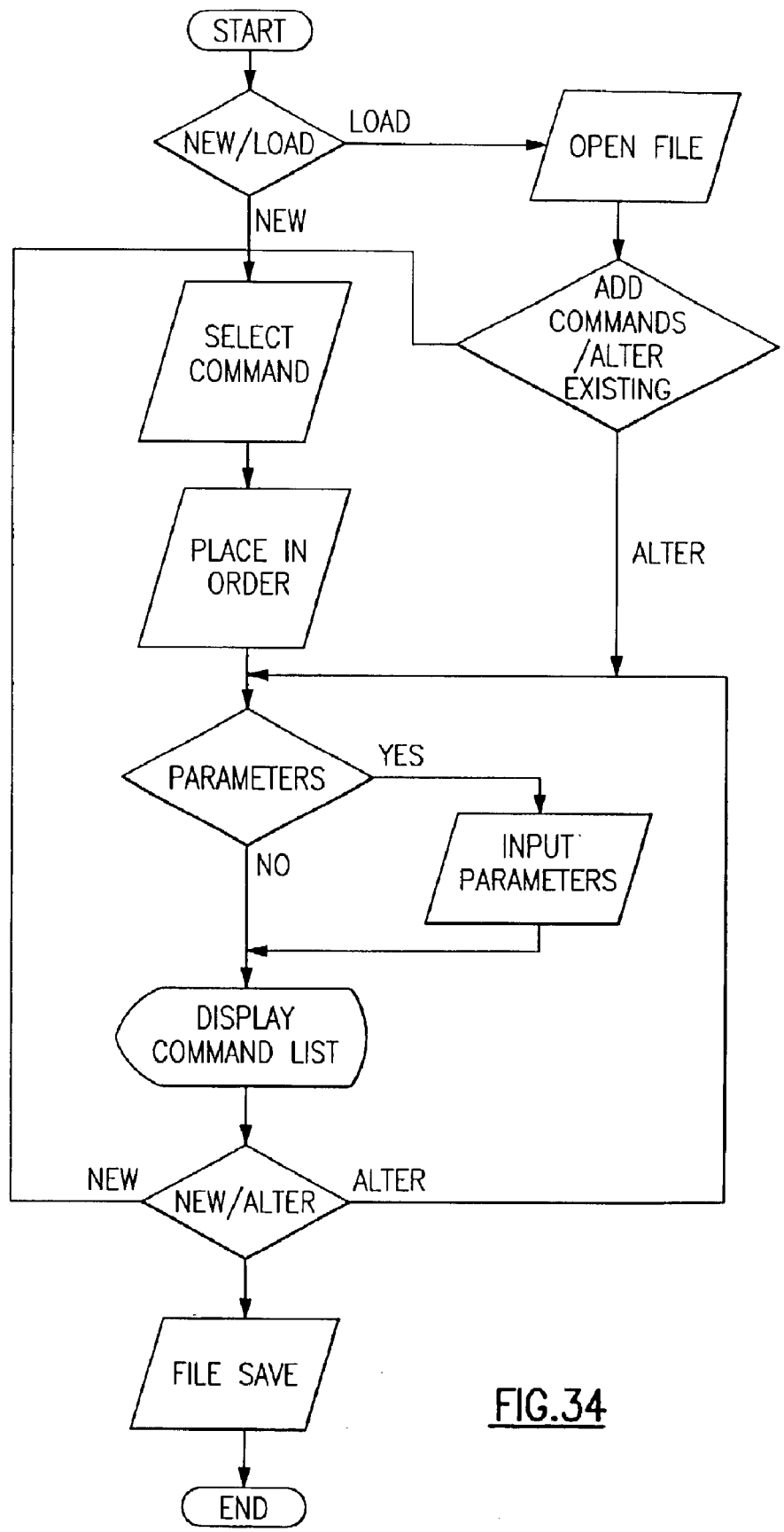
FIG. 34 illustrates a flow diagram of a procedure used in blood typing analysis.

The software may treat conditions found on the bio-disc as abstractions such as Event Capture types. For example, a glucose finding may be treated as Event Capture 1, and genetically modified organism (GMO) testing may be treated as Event Capture 3. One or more parameter tables may be used to which software code is directed and in which specific tests are implemented (optionally along with interactivity instructions). In development of tests, such tables accelerate time to market and reduce software code maintenance overhead. One parameter in such tables may relate to event counting as described below. As shown in FIG. 34, other parameters may implement decision blocks of flowcharts representing blood-typing tests, e.g., so that a decision made pertaining to zone A causes an action to be taken in zone B instead of in zone C.

As described below, the software and bio-disc system may produce quantitative as well as qualitative blood-typing results. For example, numeric results may be achieved that not only indicate a Type A blood, but also may differentiate between a strong Type A and a weak Type A blood (e.g., 85% versus 15% Type A). By supplying sensitivity, selectivity, and non-specific binding, quantitatively enhanced results are made possible.

Figure 33:
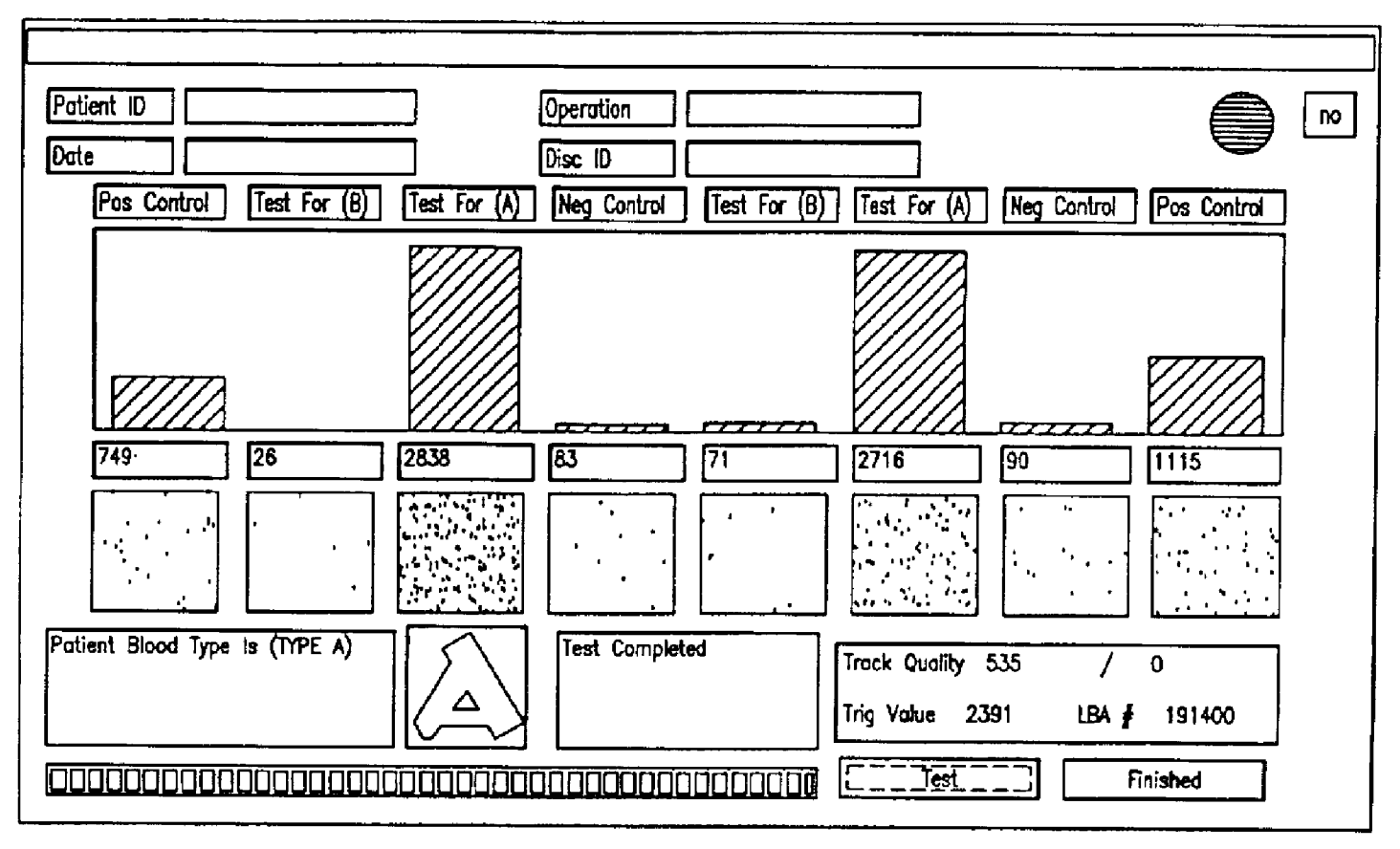

Referring next to FIG. 33, there is shown a sample display image showing the results of a blood typing assay performed using the methods and apparatus of the present invention. As indicated by the bar graph and corresponding actual physical counts of captured red blood cells, the blood sample is a strong Type A. Also shown are positive and negative control results for heightened confidence in assay reliability. In the case of a weak Type A, the corresponding bar may be much lower (e.g., just above a threshold value for Type A). Thus, the software can quantitatively detect the strength of a blood type determination, and in certain circumstances, can perform error checking and/or redundant checking functions. Such functions include, but are not limited to, retesting in the case of a weak determination, changing a threshold value for a Type determination, applying a different test, using a different sample size, and requesting action by the user. Therefore, the output of the software will be produced only after the software has determined a blood type result to a sufficient confidence level.

Under software control, the bio-disc can thus perform sophisticated interactive blood typing analysis on relatively small blood samples, without having to retrieve further blood from a patient, which may be difficult or impossible or have adverse health consequences.

Other information technology resources can be applied to the bio-disc in the blood typing techniques. For example, results of the software's analysis can be transmitted (e.g., in secure form) over a network such as the Internet for storage or further analysis. The software can be executed, updated, and/or maintained over a network such as the Internet. Reporting can be accomplished automatically by triggering a communication, e.g., to a health agency or a demography-related institution whenever a particular result is found during blood typing.

In a specific implementation, an event counting technique is used to detect and quantify material on the bio-disc and a blood typing result is produced based on an analysis of the results of executing the event counting technique. Effectively, a track-by-track scan is made of a portion of a bio-disc, spots of material are detected in the scan, and the blood type of a blood sample is determined and reported based on the quantity of detected spots.

In the technique, a sampling rate and optionally a bio-disc rotation speed is adjusted to correspond to the expected or detected size of the spots so that the spots can be reliably counted in real time using conventional and practical computing resources. For example, if red blood cells of seven micron size are being detected, a sampling rate of 667 kilohertz at a 4× rotation speed may be used to detect seven micron spots while filtering out spots of significantly different sizes.

Event counting can be performed per track or per set of tracks, optionally in real time. In a specific implementation, the read head of the optical drive mechanism is positioned at a designated track, and a set (e.g., a track's or a block's worth) of samples are read into memory. In the capture zone, an event is recorded when the readings match a predetermined profile, e.g., a transition such as a specified number of low intensity samples followed by a specified number of high intensity samples. Low intensity and high intensity may be treated as relative sample-to-sample. Events are recorded for all samples corresponding to the width of the capture zone along the track. The rest of the capture zone is scanned similarly on other tracks above and/or below the current track to locate spots that are not intersected by the current track. The event represents the spot, such that counting the events in the capture zone effectively produces a count of the spots in the capture zone.

In other embodiments, signal analysis such as digital signal processing may be performed (e.g., to implement low pass or band pass filtering) to expose features of interest such as the spots of specified size that are counted. The laser wavelength and/or laser spot size may be altered to facilitate exposure of the features.

The blood typing analysis performed by the software may depend on the number of spots (e.g., representing red blood cells) found in one or more capture zones such as target zones 140.

In a particular implementation, the event counting is performed in real time as the track data is being retrieved from the bio-disc, which allows the analysis to be performed with a small and inexpensive amount of memory, since all that is retained by the software is the event count itself, which requires little memory.

In a specific implementation, an alignment mark is predisposed on the bio-disc specifically to allow the software to determine a starting point on the track from which to determine an offset point for the capture zone of interest. The alignment symbol may include a solid black India ink dot positioned near the start of a capture zone.

The samples may represent voltage levels corresponding to light intensities measured by a detector at the bio-disc. For example, a particular 14-bit sample (or upper 8 bits of a 14-bit sample) may correspond to undisturbed reflected or transmitted light representing an absence of a feature of interest such as a red blood cell, and another sample may correspond to partially or entirely blocked light representing the presence of the feature.

In a case in which the drive mechanism is derived from a conventional CD-ROM drive, the software may use a logical block address (LBA) command to direct the mechanism to position the read head to read data from a particular track of the bio-disc. To specify a particular track, the track number is multiplied by 75 to produce a logical block number and the drive is commanded to go to the logical block number. The electronic signals from the samples that are taken may include one or more of conventional CD-ROM analog signals A–D, HF1–HF2, Focus, and Tracking. The samples may be derived from the analog signals by a Eultrad EDDA1280 A/D device from AlterView that can sample in a range from 400 kilohertz to 80 megahertz.

Other conventional CD-ROM commands that may be used by the software include initialize drive, set drive speed, track out to location, track out to location or LV positioning, test burn mode, and drive reset.

The software may attempt up to a predetermined number of times (e.g., 12) to find the alignment symbol before giving up. Multiple capture zones may be positioned along a particular track, with different offset points from the end of the alignment symbol. If the alignment symbol is found at the end of a block of data, the data may be discarded and another block may be read so that offsets may be calculated properly from the end of the alignment symbol at a point closer to the beginning of the block.

As shown in FIG. 33, the output includes a bar graph and number counts corresponding to the bars. Below the counts are boxes having spots, which are effectively images of portions of capture areas. The images are formed line by line as event counting is performed for tracks covering a capture area. A blood type is determined by calculating a ratio of counts in various capture areas.

The selection of a sample rate can be important: if the sampling rate is too low, the software may miss an object; if the sampling rate is too high, small objects of little or no interest may be improperly counted along with the objects of interest, and the data rate may become burdensome on the computing platform.

The computing platform may include a conventional personal computer including but not limited to a 433 megahertz Pentium-compatible microprocessor and running Microsoft Windows 98, and the software may be implemented in a high-level language such as Microsoft Visual C++ or Visual Basic with assembly language components where execution speed makes a significant difference (e.g., in real-time analysis of the samples).

Image analysis may be performed on the images of the capture areas to expose additional features beyond counts, such as positional arrangements of objects and local and global densities of objects.

At least some of the techniques described above can be applied to platforms other than that of microfluidic circuits on bio-discs.

FIG. 34 illustrates a high-level procedure that is executed by an implementation of the software. The procedure is used to allow parameters to be defined for use in a test such as a blood-typing test applied to a bio-disc.

Blood Analysis Using Bio-Matrix Separation

Figure 35:
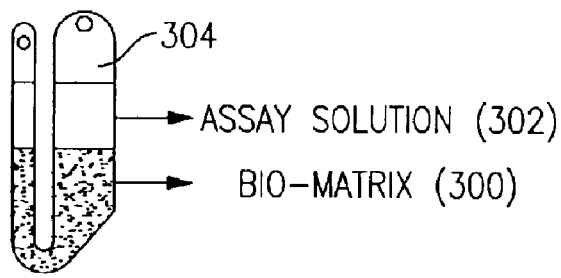
FIG. 35 illustrates a bio-matrix packed in a microfluidic channel or circuit containing an assay solution.

The hematology and immunohematology analyses methods and apparatus described above in conjunction with FIGS. 1 to 34 may be implemented using a bio-matrix method. The bio-matrix method is described above in detail in connection with the fourth aspect of the present invention. In this method, a bio-matrix is formed in a microfluidic channel or circuit in an optical bio-disc. The bio-matrix may be formed from cross-linked polymers or microparticles including polyacrylamide, agarose, and polstyrene or glass beads such as those used in liquid chromatography. FIG. 35 illustrates a micro-fluidic circuit 304 of an optical bio-disc containing a bio-matrix 300 formed therein. The fluidic circuit 304 may also contain an assay solution 302. The assay solution 302 may contain a buffer, reagent antibodies, or typed reagent cells.

Figure 36A:
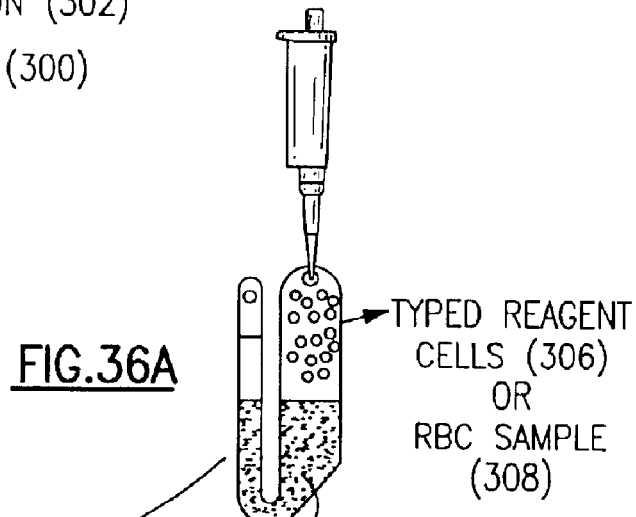
FIGS. 36A and 36B depict the addition of particles or cells and formation of agglutinates in a microfluidic channel containing a pre-formed bio-matrix.
Figure 36B:
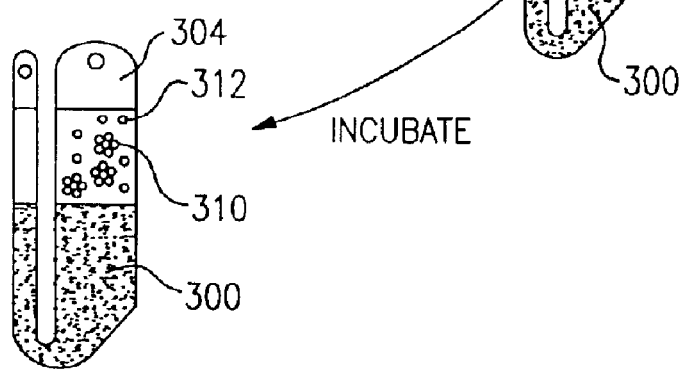

Referring to FIGS. 36A and 36B, there is illustrated the addition and reaction of particles or cells within a channel or microfluidic circuit. More specifically, FIG. 36A shows the addition of particles or cells into the bio-matrix microfluidic circuit. The cells may include typed reagent cells 306 or sample red blood cells 308. The particles then react with reagents in the assay solution to form agglutinates 310 shown in FIG. 36B. Once the agglutination reaction is completed, the disc is spun at a pre-determined speed and time to separate the agglutinated cells 310 from the non-agglutinated cells 312 using the bio-matrix 300. The result may be any one of the patterns shown in FIGS. 37A, 37B, or 37C. FIG. 37A depicts results from a strong agglutination reaction wherein all the particles or cells form agglutinates 310. The agglutinates 310 are unable to enter the bio-matrix since the pores of the matrix are too small to permit passage of these agglutinates 310. In some cases, the agglutination reaction is weak such that the agglutinates formed 310 are small enough that they may enter the matrix and are trapped within it as shown in FIG. 37B. If the analyte of interest is not present in the sample, agglutination does not occur and all the single, non-agglutinated particles or cells 312 pass through the matrix and form a pellet at the bottom or distal end of the microfluidic circuit as shown in FIG. 37C. The location and amount of the agglutinates 310 and/or non-agglutinated cells 312 may then be analyzed using an optical disc reader such as that described in the above referenced and incorporated U.S. patent application Ser. No. 10/043, 688. Data from these analyses may then be interpreted using accompanying computer software and an appropriate antigram incorporated into the disc and/or drive software to generate a blood type panel, and/or an antibody panel or profile. This method automates the blood typing and antibody screening process and decreases turn around time for hematology and immunohematology testing.

In one embodiment of the present invention, separate microfluidic channels are pre-loaded with reagent antibodies including anti-A, anti-B, or anti-AB antibodies. Diluted or washed patient or sample red blood cells are then added to each of the chambers to form an assay solution as shown in FIG. 36A. After a pre-determined incubation time, agglutination of the red blood cells, as shown in FIG. 36B, occurs in the channel containing the antibody that binds to the specific antigens (A, B, or AB antigens) on the red cells. For example, if the sample red blood cells are type A then agglutination occurs in the channel containing anti-A antibodies. Once the agglutination reaction is completed, the disc is spun at a pre-determined speed and time to separate the agglutinated cells from the non-agglutinated cells. The result may be any one of the patterns shown in FIGS. 37A, 37B, or 37C. The most common results using this embodiment are presented in FIGS. 37A and 37C which, respectively, show a strong reaction to the appropriate reagent antibody and no reaction to other antibodies. FIG. 37B illustrates the less common weak positive test result.

In another embodiment of the present invention, separate microfluidic channels are loaded with typed reagent cells including A, B, or O type reagent cells. An aliquot of patient serum or plasma is then added to the individual chambers to form an assay solution as shown in FIG. 36A. After a pre-determined incubation time, agglutination of the reagent cells, shown in FIG. 36B, occurs in the chamber containing the appropriate type of reagent cells. For example, if the serum sample contains antibodies for B type red blood cells (from a type A blood sample) agglutination will be observed in the channel containing B type reagent cells. Once the agglutination reaction is completed, the disc is spun at a pre-determined speed and time to separate the agglutinated cells from the non-agglutinated cells. The result may be any one of the patterns shown in FIGS. 37A, 37B, or 37C. Typical common results using this embodiment are shown in FIGS. 37A and 37C which, respectively, show a strong reaction of the serum antibodies to the appropriate reagent cell type and no reaction to other cell types. FIG. 37B illustrates the less common weak positive test result.

In yet another embodiment of the present invention, separate microfluidic channels are pre-loaded with Coomb's serum, or anti human globulin with or without complement. A serum sample is prepared and mixed individually with different type O reagent cells expressing different patterns of minor antigens including, but not limited to, the various types of Kell, MNSs, Duffy, Kidd, Lewis, and Lutheran antigens, to form different assay solutions. The different assay solutions may be loaded into different microfluidic channels in an optical disc as shown in FIG. 36A. Alternatively, an aliquot of the serum samples may be added to multiple chambers followed by the addition of the different type O reagent cells into different chambers containing the serum sample. Antibodies present in the sample will specifically bind to their respective antigens expressed on the reagent cell membranes. The anti-human globulin (AHG) or Coomb's serum facilitates agglutination of the antibody coated red blood cells by binding to the antibodies bound to the cells and cross linking antibodies bound to other cells in the assay solution. If there are no antibodies present in the sample which have specific affinity to the target antigens expressed on the surface of a reagent cell, then agglutination of cells does not occur since the AHG cannot cross link cells without antibodies attached to the cell surface. After a pre-determined incubation time, agglutination of the reagent cells, shown in FIG. 36B, occurs in the chamber containing the appropriate type of reagent cells. For example, if the serum sample contains antibodies for k type red blood cells, agglutination will be observed in the channel containing reagent cells expressing the k antigen. Once the agglutination reaction is completed, the disc is spun at a pre-determined speed and time to separate the agglutinated cells from the non-agglutinated cells. The result may be any one of the patterns shown in FIGS. 37A, 37B, or 37C. Expected common results using this embodiment are shown in FIGS. 37A and 37C which, respectively, show a strong reaction of the serum antibodies to the reagent cell types expressing the specific antigens of interest and no reaction to other cell types. FIG. 37B illustrates the less common weak positive test result. By incorporating the antigram for the reagent cells into a computer software analysis program, the patient's antibody expression pattern or antibodies present in the sample may be automatically determined based on the pattern of positive and negative reactions.

Referring to FIG. 38 there shown a top plan view of another embodiment of a transmissive optical bio-disc 110 showing semi-circular, equi-radial fluidic circuits 320 having inlet ports 122, vent ports 124, and trigger marks 126. The equi-radial fluidic circuits 320 include a semi-circular or arcuate analysis chamber that is substantially directed along an arc segment of an annular ring within the substrate 120 of the optical bio-disc 110. The capture zones 140 are placed within the semi-circular analysis chamber of the equi-radial fluidic circuit 320. Also shown in FIG. 38 are trigger markings 126. The disc essentially includes all the components of the transmissive optical bio-disc as described above in conjunction with FIGS. 5, 6, 7, 8, and 9.

Referring next to FIG. 39 there is illustrated an enlarged detailed view of a portion of the equi-radial fluidic circuit of the disc shown in FIG. 38. This particular fluidic circuit includes capture zones for the forward blood typing assay as described above in conjunction with FIGS. 21A to 21F. As shown in FIG. 39, the analysis chamber may have, for example, several capture zones including, but not limited to, anti-A, anti-B, anti-H, anti-C, anti-c, anti-D, anti-E, anti-e, and Rh control capture zones for testing or determining the major blood group of a blood sample. Other capture zones with capture agents specific for other antigens can be substituted for any of the above mentioned capture zones.

With reference now to FIG. 40 there is depicted an enlarged detailed view of yet another embodiment of the transmissive disc with a proximal equi-radial fluidic circuit 324 and a distal equi-radial fluidic circuit 322. The distal equi-radial fluidic circuit 322, in this embodiment, is used for forward blood typing as discussed in above FIG. 39 while the proximal equi-radial fluidic circuit 324 is used for reverse blood typing. The reverse blood typing test serves as a confirmatory test for the result generated from the forward blood typing. Details relating to sample preparation for reverse blood typing and assay procedures are discussed above in conjunction with FIGS. 23, 26A, 26B, and 26C, for example. In use, red blood cells are processed as described below in Example 2. The red blood cells are then loaded in to the distal equi-radial fluidic circuit 322 though the inlet port 122. Meanwhile, a blood sample is also prepared for reverse typing as described above in conjunction with FIG. 23 where the serum or plasma is mixed and incubated with Type A and Type B reagent cells. Then the suspension of cells and serum is loaded into the proximal equi-radial fluidic circuit 324 through the inlet port 122. The inlet and vent ports are then sealed and the disc is loaded into the optical disc drive 122 (FIG. 17) for analysis. During analysis, the disc may be rotated at a pre-determined speed and duration to remove cells or agglutinates that are not bound by the capture agents in the capture zones. The capture zones in the distal fluidic circuit 322 are then investigated to determine the zones with bound cells. The capture zones in the proximal fluidic circuit 324 are also investigated to determine which zone or zones have agglutinated cells or non-agglutinated cells bound thereto (FIG. 26C). The forward and reverse typing performed together is advantageous for accurately determining the blood type of an individual. In standard clinical blood typing, the reverse typing serves as confirmation of the correct forward typing for ABO blood grouping. The present invention permits both the forward and reverse typing to be run concurrently with reduced sample volume and minimal user intervention. In addition, the forward and reverse typing tests of the present invention may be analysed in approximately 2 minutes using appropriate hardware and software. Further details relating to optical disc drives, detection systems, and software that may be used in conjunction with the optical bio-discs of the present invention is disclosed in for example, commonly assigned and co-pending U.S. patent application Ser. No. 10/241,512 entitled "Methods for Differential Cell Counts Including Related Apparatus and Software Performing Same" filed Sep. 11, 2002; and U.S. patent application Ser. No. 10/279,677 entitled "Segmented Area Detector for Bio-drive and Methods Relating Thereto" filed Oct. 24, 2002; both of which are incorporated by reference in their entireties as if fully repeated herein.

EXPERIMENTAL EXAMPLES

While this invention has been described in detail with reference to the drawing figures, certain examples and further illustrations of the invention are presented below.

Example 1

Bio-Disc and Capture Layer Preparation

In one embodiment, the tracking of the bio-disc of the present invention is a forward Wobble Set FDL21:13707 or FDL21:1270 coating with 60 nm of gold. On this reflective disc, oval data windows of size 2×1 mm are etched out by Lithography. "U" shaped channels are used to create chambers that are 25 um in height. It takes about 7 uls of sample to fill the entire chamber including the inlet and outlet ports. A 8-window/4-channel format to be preferentially used. In the preferred embodiment of the invention a semi-reflective transmissive disc (FDL 20/21:00708) is used which allows the entire surface of a transmissive disc to be used for capture zones, without the use of lithography to form data windows. Fraylock "U" shaped adhesive DBL 201 Rev C 3M94661 or straight channels are used to create the chambers. The cover disc utilized is a gold disc, fully reflective with 48 sample inlets with a diameter of 0.040 inches location equidistant at radius 26 mm or a clear disc to allow use of a top detector.

Several chemical layers are applied sequentially to the solid substrate first layer. This first layer may be a polycarbonate layer or a metalized polycarbonate layer in a optical disc such as a CD, CD-ROM, DVD or DVD-ROM. Prior to subsequent treatment, the first layer is cleaned with isopropanol. The second layer consists of either polystyrene or polycarbonate. This layer may be formed by injection molding of bulk plastic or spin or spray coating of the plastic in a volatile solvent on a solid substrate.

The primary capture layer, the third layer, is formed by absorption of the protein streptavidin (Sigma, St. Louis, Mo., Catalogue No. S-4762) (or any variant thereof) on the second layer. The adsorption process is accomplished by exposure of the second layer to a first solution (1 mg/ml solution of streptavidin (or any variant thereof) at neutral pH (+/−0.5 pH) in either phosphate (sodium or potassium) or Tris buffer, ionic strength (varied by addition of NaCl, KCl or $MgCl_2$) between 50 and 200 mM). Exposure times may range between 30 seconds and 12 hours. After exposure of the second layer to the first solution, the excess streptavidin (or any variant thereof) is washed away with water.

The secondary capture layer, the fourth layer, consists of biotin-labeled antibody (the first capture antibody) that recognize and bond to other antibodies from a certain animal source (e.g., mouse or human) (e.g., biotinylated anti-mouse IgM (raised in sheep), Vector Laboratories, Catalog # BA-2020). A solution of the first capture antibody (the second solution) is exposed to the third layer for between 10 minutes and 3 hours. The second solution comprises a 0.5 mg/ml solution of the first capture antibody at neutral pH (+/−0.5 pH) in either phosphate (sodium or potassium) or Tris buffer, ionic strength (varied by addition of NaCl, KCl or $MgCl_2$) between 50 and 200 mM. The biotin moiety on the surface of the first capture antibody is bound by the streptavidin (or any variant thereof), which comprises the third layer. After exposure of this layer to the second solution, the excess first capture antibody is washed away with water.

The bioactive capture layer, the fifth layer, consists of the second capture antibody, which recognizes and binds to a specific type of biological cell based on some antigen on the surface of that cell. The animal source of the second capture antibody must match the specificity of the first capture antibody. A solution of the second capture antibody is exposed to the fourth layer for between 10 minutes and 3 hours. This third solution comprises a solution (possibly 1 mg/ml) of the second capture antibody at neutral pH (+/−0.5 pH) in either phosphate (sodium or potassium) or Tris buffer, ionic strength (varied by addition of NaCl, KCl or $MgCl_2$) between 50 and 200 mM. After exposure of the fourth layer to the third solution, excess second capture antibody is washed away with a buffer similar to that described above.

Since blood is analyzed, the discs of the invention are leak checked to make certain that none of the chambers leak during spinning of the disc with the sample in situ. Each channel is filled with a blocking agent. Blocking is done for least 1 hour. The discs are then spun at 5000 rpm for 5 minutes and examined. After checking for leaks and removing the blocking solution, the disc is placed in a vacuum chamber for 2–48 hours. After vacuum treatment, discs are placed in a vacuum pouch and stored at 2–8° C. until use.

Additionally, the disc can be heat or ultrasonically bonded to make certain no fluid escapes from the chamber.

Example 2

Forward Blood Typing Assay on Bio-Disc

In the example to follow, the forward blood typing assay is conducted on a bio-disc comprising: (1) gold reflective base disc, treated with photo-lithography to remove the gold in specific capture zones, with appropriate chemistry placed over the capture zones, (2) 25 um thick channel layer, and (3) gold reflective cover disc, assembled into a functional bio-disc.

10 ul of whole blood from a finger stick is diluted in 90 ul of phosphate buffered saline/anticoagulatant to make a 10% RBC solution. 14 ul of this is injected into the functional bio-disc and the inlet and vent ports are sealed. After a five-minute room temperature incubation, the disc is placed into the drive. The automated event counting software developed in-house centrifuges the disc, causing the non-specifically captured cells to be removed from the capture zones. The disc is scanned with the standard 780 nm laser of the optical drive using the bottom detector and the software registers the number of events in each capture zone. The program algorithm determines which capture zones had a positive capture and assigns an ABO and Rh phenotype to the blood sample. The entire process takes about 10 to 15 minutes from insertion of disc into the drive and receiving the forward blood typing. The diagnostic protocol is presented pictorially in FIG. 8.

Results are presented in FIG. 19, which is a representation of a graphical output for ABO blood typing.

Example 3

Reverse Typing Assay on Bio-Disc With Sample Preparation Off-Disc

In the example to follow, the reverse blood typing assay is conducted on a bio-disc comprising: (1) gold reflective base disc, treated with photo-lithography to remove the gold in specific capture zones, with appropriate chemistry placed over the capture zones, (2) 25 um thick channel layer, and (3) gold reflective cover disc, assembled into a functional bio-disc.

Whole blood is centrifuged at an appropriate speed and time to result in a pellet of cells and non-hemolyzed serum or plasma. The serum or plasma is separately mixed with Type $A_1$ and Type B Reagent Red Blood Cells (Ortho Clinical Diagnostics). The mixture of the cells and serum or plasma may take place in test tubes or directly on the disc in a mixing chamber. If the mixing occurs in a test tube, each mixture is then placed in separate channels of the disc. After a short, room temperature incubation (2 to 5 minutes) to allow the serum or plasma to interact with the reagent red blood cells, the disc is placed into the drive. The automated agglutination-detection software developed in-house centrifuges the disc, causing the agglutinated and/or non-agglutinated cells to travel over the capture zone and be non-specifically captured. Excess cells will be centrifuged to the outer edge of the flow channel. The disc is scanned with the standard 780 nm laser of the optical drive using the bottom detector and the software registers.

The program algorithm determines which reagent red blood cells were agglutinated and assigns an ABO phenotype, based on reverse typing to the plasma or serum sample. The entire process takes about 10 minutes from insertion of disc into the drive and receiving the reverse blood typing. The forward and reverse typings of an individual should be in agreement, signifying the correct typing of that individual.

Concluding Summary

While this invention has been described in detail with reference to a certain preferred embodiments, it should be appreciated that the present invention is not limited to those precise embodiments. Rather, in view of the present disclosure which describes the current best mode for practicing the invention, many modifications and variations would present themselves to those of skill in the art without departing from the scope and spirit of this invention. The scope of the invention is, therefore, indicated by the following claims rather than by the foregoing description. All changes, modifications, and variations coming within the meaning and range of equivalency of the claims are to be considered within their scope.

Furthermore, those skilled in the art will recognize, or be able to ascertain, using no more than routine experimentation, many equivalents to the specific embodiments of the invention described herein. Such equivalents are intended to be encompassed by the following claims.

What is claimed is:

1. A method for determining the presence of antibodies to an ABO blood group of an individual's blood sample by reverse-typing on an optical bio-disc comprising:

applying a blood sample to at least one microfluidic channel in the optical bio-disc including a separation chamber with at least one microfilter, at least one mixing chamber, and at least one capture chamber;

spinning the optical bio-disc for a first time at a first speed to effect separation of the blood sample into cells and serum in the separation chamber;

spinning the optical bio-disc for a second time at a second speed higher than the first, the second speed effecting movement of the serum through the microfluidic channel into a mixing chamber;

adding cells of a known ABO blood group cells into the mixing chamber containing serum;

spinning the optical bio-disc for a third time in one direction and alternately in another direction at least once to effect mixing of the serum and the cells;

incubating the cells in the serum for a sufficient period of time to allow antibody-antigen binding;

spinning the optical bio-disc for a fourth time at a third speed higher than the second, the third speed effecting movement of the cells into a capture chamber, the capture chamber including surface with a molecule that binds cells;

incubating the sample in the capture chamber to promote cell binding to the capture chamber surface;

spinning the disc for a fifth time to remove non-bound cells from the capture chamber;

scanning the capture chamber with an incident beam of electromagnetic radiation by rotating the disc about an axis substantially perpendicular to a first face of the disc and by moving the incident beam in a direction radial to the axis;

detecting a return beam of electromagnetic radiation formed by at least a part of the incident beam after interacting with the disc;

converting the return beam into an output signal;

analyzing the output signal to determine the presence of agglutinated cells; and determining the presence of antibodies in the sample.

2. A method for determining the presence of antibodies to a blood group type of an individual by antibody-typing on an optical bio-disc comprising:

applying a blood sample to at least one microfluidic channel in the optical bio-disc including a separation chamber with at least one microfilter, at least one mixing chamber, and at least one capture chamber;

spinning the optical bio-disc for a first time at a first speed to effect separation of the blood sample into cells and serum in the separation chamber;

spinning the optical bio-disc for a second time at a second speed higher than the first, the second speed effecting movement of the serum through the microfluidic channel into a mixing chamber;

adding cells of a known blood group phenotype into the mixing chamber containing serum;

spinning the optical bio-disc for a third time in one direction and alternately in another direction at least once to effect mixing of the serum and the cells of a known blood group phenotype;

incubating the cells of a known blood group phenotype in the serum for a sufficient period of time to allow antibody-antigen binding;

spinning the optical bio-disc for a fourth time at a third speed higher than the second, the third speed effecting movement of the cells of a known blood group phenotype into of a capture chamber, the capture chamber including a surface with an anti-human immunoglobulin molecule;

incubating the sample in the capture chamber to promote binding of the cells of a known blood group phenotype to the capture chamber surface;

spinning the optical bio-disc for a fifth time to remove non-bound cells of a known blood group phenotype;

scanning the capture chamber with an incident beam of electromagnetic radiation by rotating the disc about an axis substantially perpendicular to a first face of the disc and by moving the incident beam in a direction radial to the axis;

detecting a return beam of electromagnetic radiation formed by at least a part of the incident beam after interacting with the disc;

converting the return beam into an output signal;

analyzing the output signal to determine if the cells of a known blood group phenotype are captured; and determining the presence of blood group antibodies.

3. A method for determining the presence of antibodies to an ABO blood group of an individual's blood sample by reverse-typing on an optical bio-disc, said method comprising:

loading a blood sample into at least one microfluidic channel in the optical bio-disc including a preparation chamber with at least one microfilter, at least one mixing chamber, and at least one separation chamber, said separation chamber having a bio-matrix packed therein such that the packing density allows single cells to pass through and prevents agglutinated cells from entering;

spinning the disc for a first time at a first speed to effect separation of the blood sample into cells and serum in the preparation chamber;

spinning the disc for a second time at a second speed greater than the first, the second speed effecting movement of the serum through the microfluidic channel into the mixing chamber;

adding cells of a known ABO blood group into the mixing chamber containing the serum;

spinning the disc for a third time at a third speed in one direction and alternately in another direction at least once to effect mixing of the serum and the cells of a known ABO blood group;

incubating the cells of a known ABO blood group with the serum for a sufficient period of time to allow antibody-antigen binding and cell agglutination; and spinning the disc for a fourth time at a fourth speed greater than the second, the fourth speed effecting movement of the cells of a known ABO blood group into the separation chamber and into the bio-matrix so that agglutinated cells are separated from non-agglutinated cells.

4. The method according to claim 3 including the further step of scanning the chamber with an incident beam of electromagnetic radiation by rotating the disc about an axis substantially perpendicular to a substrate portion of the disc and by moving the incident beam in a direction radial to the axis.

5. The method according to claim 4 including the further step of detecting a return beam of electromagnetic radiation formed by at least a part of the incident beam after interacting with the disc.

6. The method according to claim 5 including the further step of converting the return beam into an output signal.

7. The method according to claim 6 including the further step of analyzing the output signal to determine the presence of agglutinated cells to thereby determine the presence of antibodies in the sample.

8. A method for determining the presence of antibodies of an ABO blood group of an individual's blood sample by reverse-typing on an optical bio-disc, said method comprising:

loading a blood sample to at least one microfluidic channel in the optical bio-disc including a separation chamber with at least one microfilter, at least one mixing chamber, and at least one capture chamber;

spinning the disc a first time at a first speed to effect separation of the blood sample into blood cells and serum in the separation chamber;

spinning the disc a second time at a second speed greater than the first, the second speed effecting movement of the serum through the microfluidic channel into a mixing chamber;

adding type A and type B reagent cells into the mixing chamber containing the serum;

spinning the disc a third time at a third speed in one direction and alternately in another direction at least once to effect mixing of the serum and the reagent cells;

incubating the reagent cells in the serum for a sufficient period of time to allow antibody-antigen binding and cell agglutination; and spinning the optical bio-disc for a fourth time at a fourth speed greater than the second, the fourth speed effecting movement of the reagent cells into said capture chamber, said capture chamber including a surface with a capture agent.

9. The method according to claim 8 wherein said capture agent is selected from the group comprising an antibody directed against type A reagent cells and an antibody directed against type B reagent cells.

10. The method according to claim 9 including the further step of incubating the sample in the capture chamber to promote cell binding to the capture agent.

11. The method according to claim 10 including the further step of spinning the disc for a fifth time to remove non-bound reagent cells from the capture field.

12. The method according to claim 11 including the further step of scanning the chamber with an incident beam of electromagnetic radiation by rotating the disc about an axis substantially perpendicular to said substrate and by moving the incident beam in a direction radial to the axis.

13. The method according to claim 12 including the further step of detecting a return beam of electromagnetic radiation formed by at least a part of the incident beam after interacting with the disc.

14. The method according to claim 13 including the further step of converting the return beam into an output signal.

15. The method according to claim 14 including the further step of analyzing the output signal to determine the presence and amount of agglutinated and non-agglutinated reagent cells to thereby determine the presence of antibodies in the sample.

* * * * *

UNITED STATES PATENT AND TRADEMARK OFFICE
CERTIFICATE OF CORRECTION

PATENT NO. : 7,026,131 B2
APPLICATION NO. : 10/298263
DATED : April 11, 2006
INVENTOR(S) : Hurt et al.

It is certified that error appears in the above-identified patent and that said Letters Patent is hereby corrected as shown below:

First Page Col. 2, Line 1, Delete "US 6,200755, 10/2000, Virtanen (withdrawn)".

First Page Col. 2, Line 2, Delete "et al." and insert -- et al.,-- therefor.

First Page Col. 2, Line 2, Delete "cappilarity" and insert -- capillarity --, therefor.

Page 2 Col. 2, line 1, Delete "et al." and insert -- et al., --, therefor.

Page 2 Col. 2, line 3, Delete "Chem," and insert -- Chem., --, therefor.

Page 2 Col. 2, Line 6, Below "6,176,962 B1  1/2001 Soane el al." insert -- US 6,200,755, 10/2000, Virtanen --.

Col. 4, Line 59, Delete ""A'" and insert --"A"--, therefor.

Col. 5, Line 64, Delete "anaylsis" and insert --analysis--, therefor.

Col. 7, Line 56, Delete "antibody-typing" and insert --antibody typing--, therefor.

Col. 11, Line 55, Delete "an" and insert --a--, therefor.

Col. 20, Lines 39-53, Delete "FIG. 15 is a view similar to FIG. 11 showing.......... semi-reflective layer 143." And insert the same as a new paragraph.

Col. 21, Line 7, Delete "e.g." and insert --e.g.,--, therefor.

Col. 21, Line 59, Delete "Ltd," and insert --Ltd.,--, therefor.

Col. 21, Line 63, After "Systems)" insert --.--.

Col. 22, Line 36, Delete "entirely" and insert --entirety--, therefor.

UNITED STATES PATENT AND TRADEMARK OFFICE
CERTIFICATE OF CORRECTION

| | |
|---|---|
| PATENT NO. | : 7,026,131 B2 |
| APPLICATION NO. | : 10/298263 |
| DATED | : April 11, 2006 |
| INVENTOR(S) | : Hurt et al. |

It is certified that error appears in the above-identified patent and that said Letters Patent is hereby corrected as shown below:

Col. 23 (Table 2), Line 22, Below "Capture Layer Assembly and Variations" delete "Window".

Col. 23 Row 3 (Table), Line 23, Before "1" insert --Window--.

Col. 24, Line 50, Delete "i.e." and insert --i.e.,--, therefor.

Col. 25, Lines 53-62, Delete "Various embodiments of this method of the invention may........tested on a single bio-disc." And insert the same as a new paragraph.

Col. 25, Line 63, Delete "Antigentic" and insert --Antigenic--, therefor.

Col. 26, Line 22, Delete "Co;" and insert --Co.;--, therefor.

Col. 27, Line 57, Delete "steptavidin" and insert --streptavidin --, therefor.

Col. 31, Line 55, Delete "patients" and insert -- Patient's --, therefor.

Col. 37, Line 51, Delete "polstyrene" and insert -- polystyrene --, therefor.

Col. 41, Line 15, Before "optical" delete "a" and insert --an--, therefor.

Col. 41, Line 31, Delete "MgCl2)" and insert -- $MgCl_2$) --, therefor.

Col. 41, Line 46, Delete "MgCl2)" and insert -- $MgCl_2$) --, therefor.

Col. 41, Line 62, Delete "MgCl2)" and insert -- $MgCl_2$) --, therefor.

Col. 42, Line 56, Delete "$A_1$" and insert -- A1 --, therefor.

UNITED STATES PATENT AND TRADEMARK OFFICE
CERTIFICATE OF CORRECTION

PATENT NO. : 7,026,131 B2
APPLICATION NO. : 10/298263
DATED : April 11, 2006
INVENTOR(S) : Hurt et al.

It is certified that error appears in the above-identified patent and that said Letters Patent is hereby corrected as shown below:

Col. 44, Line 44, delete "antibody-typing" and insert -- antibody typing --, therefor.

Signed and Sealed this

Twentieth Day of March, 2007

JON W. DUDAS
*Director of the United States Patent and Trademark Office*